(12) United States Patent
Wang et al.

(10) Patent No.: US 7,365,241 B2
(45) Date of Patent: Apr. 29, 2008

(54) SEED SPECIFIC USP PROMOTERS FOR EXPRESSING GENES IN PLANTS

(75) Inventors: Qi Wang, St. Louis, MO (US); Tanya Fagaly, St. Louis, MO (US); Ronald Bassuner, Calgary (CA); Jihong Liang, Chesterfield, MO (US); Tim N. Oulmassov, Chesterfield, MO (US); John Dabrowski, Rock Hill, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 11/436,903

(22) Filed: May 18, 2006

(65) Prior Publication Data

US 2006/0282922 A1 Dec. 14, 2006

Related U.S. Application Data

(62) Division of application No. 10/429,516, filed on May 5, 2003, now Pat. No. 7,078,588.

(60) Provisional application No. 60/377,236, filed on May 3, 2002.

(51) Int. Cl.
C12N 15/09 (2006.01)
C12N 15/82 (2006.01)
A01H 5/00 (2006.01)

(52) U.S. Cl. .................. 800/287; 800/298; 800/295; 800/286; 800/312; 800/322; 800/306; 800/320.1; 800/320.2; 800/320.3; 435/468; 536/24.1

(58) Field of Classification Search .............. 800/287
See application file for complete search history.

(56) References Cited

U.S. PATENT DOCUMENTS 5,850,016 A 12/1998 Jung et al. ............ 800/205
6,566,585 B1 5/2003 Quanz ..................... 800/284
7,078,588 B2 7/2006 Wang et al. ............. 800/287

OTHER PUBLICATIONS

Kim et al. Plant Molecular Biology, 1994 vol. 24, pp. 105-117.*
Benfey et al. Science, 1990, vol. 250, pp. 959-966.*
Baäumlein et al.; "A novel seed protein gene from *Vicia faba* is developmentally regulated in transgenic tobacco and arabidopsis plants," *Mol. Gen Genet*, 225:459-467, 1991.
Bassüner et al.; "Abundant embryonic mRNA in Field Bean (*Vicia faba* L.) codes for a new class of seed proteins: cDNA cloning and characterization of the primary translation product," *Plant Molecular Biology*, 11:321-3348, 1988.
Bassüner et al.; "Analysis of in vivo and in vitro globulin formation during cotyledon development of field beans (*Vicia faba* L. var. minor)," *Biochem. Physiol. Pflanzen*, 178:665-684, 1983.
Fiedler et al.; "A complex ensemble of cis-regulatory elements controls the expression of a *Vicia faba* non-storage seed protein gene," *Plant Molecular Biology*, 22:669-679, 1993.
Il'ichev et al.; "Effect of promoter duplication in the synthetic interferon gene on the level of its expression," Database accession No. NLM3030886.

\* cited by examiner

*Primary Examiner*—Medina A. Ibrahim
(74) *Attorney, Agent, or Firm*—Sonnenschein Nath & Rosenthal LLP

(57) ABSTRACT

The present invention relates to the field of plant genetic engineering. More specifically, the present invention relates to seed specific gene expression. The present invention provides promoters capable of transcribing heterologous nucleic acid sequences in seeds, and methods of modifying, producing, and using the same.

24 Claims, 21 Drawing Sheets

SEED SPECIFIC USP PROMOTERS FOR EXPRESSING GENES IN PLANTS

This application is a divisional application of currently application Ser. No. 10/429,516, filed May 5, 2003 now U.S. Pat. No. 7,078,588, which claims the benefit of the filing date of the provisional Application U.S. Ser. No. 60/377,236, filed May 3, 2002. The entire disclosure of each of the foregoing applications is specifically incorporated herein by reference.

The present invention relates to the field of plant genetic engineering. More specifically, the present invention relates to seed specific gene expression. The present invention provides promoters capable of transcribing heterologous nucleic acid sequences in seeds, and methods of modifying, producing, and using the same.

Seeds provide an important source of dietary protein for humans and livestock. However, the protein content of seeds is often incomplete. For example, many seed proteins are deficient in one or more essential amino acids. This deficiency may be overcome by genetically modifying the native or non-native proteins to have a more nutritionally complete composition of amino acids (or some other desirable feature) and to overexpress the modified proteins in the transgenic plants. Alternatively, one or more genes could be introduced into a crop plant to manipulate the metabolic pathways and modify the free amino acid content. These approaches are useful in producing crops exhibiting important agricultural (e.g., yield), nutritional, and pharmaceutical properties.

Despite the availability of many molecular tools, the genetic modification of seeds is often constrained by an insufficient accumulation of the engineered protein. Many intracellular processes may impact the overall protein accumulation, including transcription, translation, protein assembly and folding, transport, and proteolysis. Intervention in one or more of these processes can increase the amount of protein produced in genetically engineered seeds.

Introduction of a gene can cause deleterious effects on plant growth and development. Under such circumstances, the expression of the gene may need to be limited to the desired target tissue. For example, it might be necessary to express an amino acid deregulation gene in a seed-specific or seed-enhanced fashion to avoid an undesired phenotype that may affect yield or other agronomic traits.

The promoter portion of a gene plays a central role in controlling gene expression. Along the promoter region, the transcription machinery is assembled and transcription is initiated. This early step is often a key regulatory step relative to subsequent stages of gene expression. Transcription initiation at the promoter may be regulated in several ways. For example, a promoter may be induced by the presence of a particular compound, express a gene only in a specific tissue, or constitutively express a coding sequence. Thus, transcription of a coding sequence may be modified by operably linking the coding sequence to promoters with different regulatory characteristics.

SUMMARY OF THE INVENTION

The present invention includes and provides a transformed plant containing a nucleic acid molecule that comprises a promoter comprising a nucleic acid sequence that hybridizes under stringent conditions with a nucleic acid sequence selected from the group consisting of SEQ ID NOs: 1, 2, 3, 4, 9, 10, and 11, and complements thereof. The present invention includes and provides a transformed plant containing a nucleic acid molecule that comprises a promoter comprising a nucleic acid sequence selected from the group consisting of SEQ ID NOs: 1, 2, 3, 4, 9, 10, and 11, and complements thereof operably linked to a structural nucleic acid sequence.

The present invention includes and provides a transformed plant containing a nucleic acid molecule that comprises a promoter comprising a nucleic acid sequence selected from the group consisting of: a nucleic acid sequence having greater than about 85.5% identity to SEQ ID NO: 1 or its complement, a nucleic acid sequence having greater than about 85.5% identity to SEQ ID NO: 2 or its complement, a nucleic acid sequence having greater than about 97.1% identity to SEQ ID NO: 3 or its complement, and a nucleic acid sequence having greater than about 96.4% identity to SEQ ID NO: 4 or its complement.

The present invention includes and provides a method of producing a transformed plant comprising: providing a nucleic acid molecule that comprises a promoter comprising a nucleic acid sequence selected from the group consisting of SEQ ID NOs: 1, 2, 3, 4, 9, 10, and 11, and complements thereof, operably linked to a structural nucleic acid sequence; and transforming a plant with said nucleic acid molecule.

The present invention includes and provides a method of expressing a structural nucleic acid molecule in a seed comprising: growing a transformed plant containing a nucleic acid molecule that comprises a promoter comprising a nucleic acid sequence selected from the group consisting of SEQ ID NOs: 1, 2, 3, 4, 9, 10, and 11, and complements thereof, operably linked to said structural nucleic acid molecule, wherein said transformed plant produces said seed and said structural nucleic acid molecule is transcribed in said seed; and isolating said seed.

The present invention includes and provides a method of obtaining a seed enhanced in a product of a structural nucleic acid molecule comprising: growing a transformed plant containing a nucleic acid molecule that comprises a promoter comprising a nucleic acid sequence selected from the group consisting of SEQ ID NOs: 1, 2, 3, 4, 9, 10, and 11, and complements thereof, operably linked to said structural nucleic acid molecule, wherein said transformed plant produces said seed and said structural nucleic acid molecule is transcribed in said seed; and isolating said seed from said transformed plant.

The present invention includes and provides a method of obtaining meal enhanced in a product of a structural nucleic acid molecule comprising: growing a transformed plant containing a nucleic acid molecule that comprises a promoter comprising a nucleic acid sequence selected from the group consisting of SEQ ID NOs: 1, 2, 3, 4, 9, 10, and 11, and complements thereof, operably linked to said structural nucleic acid molecule, wherein said transformed plant produces a seed and said structural nucleic acid molecule is transcribed in said seed; and preparing said meal comprising said transformed plant or part thereof.

The present invention includes and provides a method of obtaining feedstock enhanced in a product of a structural nucleic acid molecule comprising: growing a transformed plant containing a nucleic acid molecule that comprises a promoter comprising a nucleic acid sequence selected from the group consisting of SEQ ID NOs: 1, 2, 3, 4, 9, 10, and 11, and complements thereof, operably linked to said structural nucleic acid molecule, wherein said transformed plant produces a seed and said structural nucleic acid molecule is transcribed in said seed; and preparing said feedstock comprising said transformed plant or part thereof.

The present invention includes and provides a method of obtaining oil enhanced in a product of a structural nucleic acid molecule comprising: growing a transformed plant containing a nucleic acid molecule that comprises a promoter comprising a nucleic acid sequence that hybridizes under stringent conditions with a nucleic acid sequence selected from the group consisting of SEQ ID NOs: 1, 2, 3, 4, 9, 10, and 11, and complements thereof, operably linked to said structural nucleic acid molecule, wherein said transformed plant produces a seed and said structural nucleic acid molecule is transcribed in said seed; and isolating said oil.

The present invention includes and provides a cell containing a vector comprising a nucleic acid sequence selected from the group consisting of SEQ ID NOs: 1, 2, 3, 4, 9, 10, and 11, and complements thereof.

The present invention includes and provides oil produced from one or more seeds of a transformed plant containing a nucleic acid molecule that comprises a promoter comprising a nucleic acid sequence selected from the group consisting of SEQ ID NOs: 1, 2, 3, 4, 9, 10, and 11, and complements thereof.

The present invention includes and provides oil produced from one or more seeds of a transformed plant containing a nucleic acid molecule that comprises a promoter comprising a nucleic acid sequence selected from the group consisting of SEQ ID NOs: 1, 2, 3, 4, 9, 10, and 11, and complements thereof, operably linked to a structural nucleic acid sequence, wherein the promoter is heterologous with respect to the structural nucleic acid sequence.

The present invention includes and provides a seed generated by a transformed plant containing a nucleic acid molecule that comprises: a promoter comprising a nucleic acid sequence selected from the group consisting of SEQ ID NOs: 1, 2, 3, 4, 9, 10, and 11, and complements thereof.

The present invention includes and provides feedstock comprising a transformed plant or part thereof containing a nucleic acid molecule that comprises a promoter comprising a nucleic acid sequence selected from the group consisting of SEQ ID NOs: 1, 2, 3, 4, 9, 10, and 11, and complements thereof.

The present invention includes and provides meal comprising plant material from a transformed plant containing a nucleic acid molecule that comprises a promoter comprising a nucleic acid sequence selected from the group consisting of SEQ ID NOs: 1, 2, 3, 4, 9, 10, and 11, and complements thereof.

The present invention includes and provides a container of seeds, wherein at least about 25% of said seeds comprise a promoter comprising a nucleic acid sequence selected from the group consisting of SEQ ID NOs: 1, 2, 3, 4, 9, 10, and 11, and complements thereof, operably linked to a structural nucleic acid sequence, wherein said promoter is heterologous with respect to the structural nucleic acid sequence.

The present invention includes and provides a substantially purified nucleic acid molecule comprising a nucleic acid sequence selected from the group consisting of SEQ ID NOs: 1, 2, 3, 4, 9, 10, and 11, and complements thereof.

The present invention includes and provides a substantially purified nucleic acid molecule having a nucleic acid sequence selected from the group consisting of: a nucleic acid sequence having greater than about 85.5% identity to SEQ ID NO: 1 or its complement, a nucleic acid sequence having greater than about 85.5% identity to SEQ ID NO: 2 or its complement, a nucleic acid sequence having greater than about 97.1% identity to SEQ ID NO: 3 or its complement, and a nucleic acid sequence having greater than about 96.4% identity to SEQ ID NO: 4 or its complement.

The present invention includes and provides a transformed soybean plant containing a nucleic acid molecule that comprises a promoter comprising a nucleic acid sequence that hybridizes under stringent conditions with a nucleic acid sequence selected from the group consisting of SEQ ID NOs: 1, 2, 3, 4, 5, 9, 10, and 11, and complements thereof.

The present invention includes and provides a transformed soybean plant containing a nucleic acid molecule that comprises a promoter comprising a nucleic acid sequence selected from the group consisting of SEQ ID NOs: 1, 2, 3, 4, 5, 9, 10, and 11, and complements thereof operably linked to a structural nucleic acid sequence.

BRIEF DESCRIPTION OF THE SEQUENCES

Figure 1:
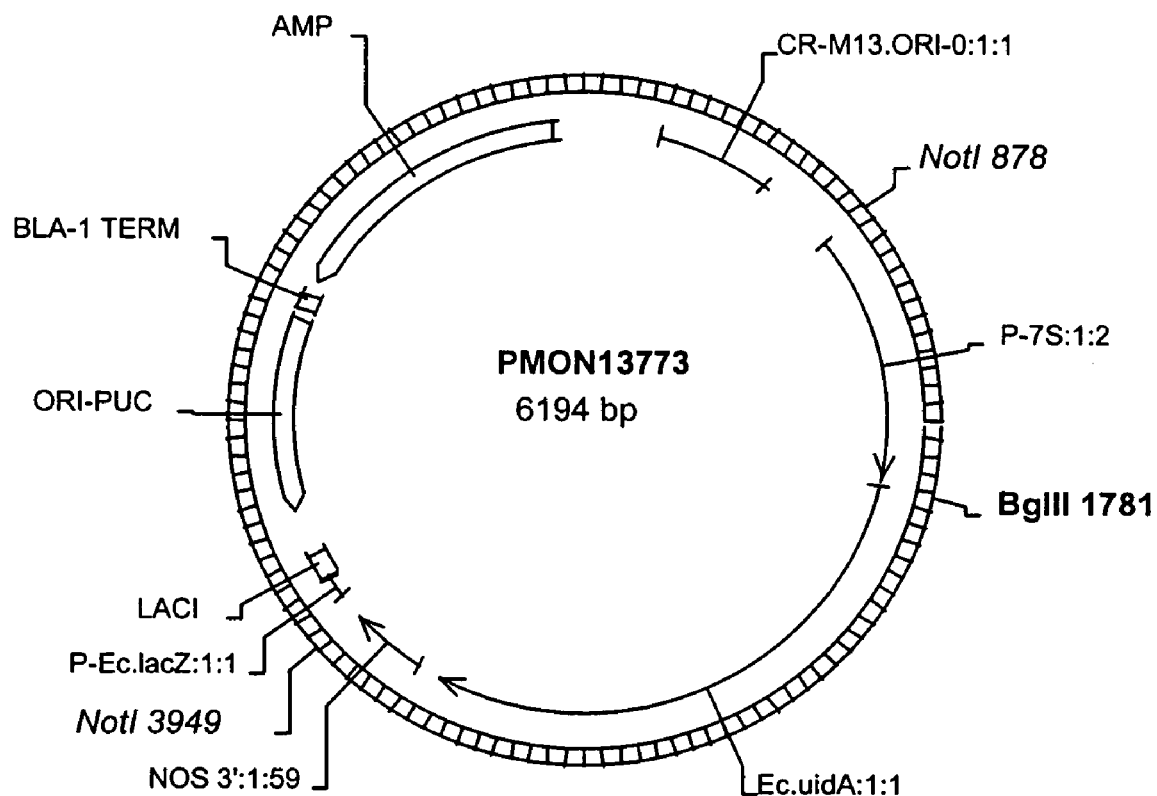
FIG. 1 is a schematic of vector pMON13773.

SEQ ID NO: 1 is a USP88 promoter sequence from *Vicia faba*.
SEQ ID NO: 2 is an eUSP88 promoter sequence from *Vicia faba*.
SEQ ID NO: 3 is a USP99 promoter sequence from *Vicia faba*.
SEQ ID NO: 4 is a USP91 promoter sequence from *Vicia faba*.
SEQ ID NO: 5 is a USP promoter sequence from *Vicia faba*.
SEQ ID NO: 6 is a primer sequence for amplifying the USP promoter from *Vicia faba*.
SEQ ID NO: 7 is a primer sequence for amplifying the USP promoter from *Vicia faba*.
SEQ ID NO: 8 is a primer sequence for amplifying the USP promoter from *Vicia faba*.
SEQ ID NO: 9 is a USP99.5 promoter sequence from *Vicia faba*.
SEQ ID NO: 10 is a USP95 promoter sequence from *Vicia faba*.
SEQ ID NO: 11 is a USP68 promoter sequence from *Vicia faba*.

SEQ ID NO: 12 is a primer sequence for amplifying a USP promoter from *Vicia faba*.

SEQ ID NO: 13 is a primer sequence for amplifying a USP promoter from *Vicia faba*.

SEQ ID NO: 14 is a primer sequence for amplifying a USP promoter from *Vicia faba*.

SEQ ID NO: 15 is a primer sequence for amplifying a USP promoter from *Vicia faba*.

SEQ ID NO: 16 is a primer sequence for amplifying a USP promoter from *Vicia faba*.

DEFINITIONS

The following definitions are provided as an aid to understanding the detailed description of the present invention.

The phrases "coding sequence," "structural sequence," and "structural nucleic acid sequence" refer to a physical structure comprising an orderly arrangement of nucleotides. The nucleotides are arranged in a series of triplets that each form a codon. Each codon encodes a specific amino acid. Thus, the coding sequence, structural sequence, and structural nucleic acid sequence encode a series of amino acids forming a protein, polypeptide, or peptide sequence. The coding sequence, structural sequence, and structural nucleic acid sequence may be contained within a larger nucleic acid molecule, vector, or the like. In addition, the orderly arrangement of nucleotides in these sequences may be depicted in the form of a sequence listing, figure, table, electronic medium, or the like.

The phrases "DNA sequence," "nucleic acid sequence," and "nucleic acid molecule" refer to a physical structure comprising an orderly arrangement of nucleotides. The DNA sequence or nucleotide sequence may be contained within a larger nucleotide molecule, vector, or the like. In addition, the orderly arrangement of nucleic acids in these sequences may be depicted in the form of a sequence listing, figure, table, electronic medium, or the like.

The term "expression" refers to the transcription of a gene to produce the corresponding mRNA and translation of this mRNA to produce the corresponding gene product (i.e., a peptide, polypeptide, or protein).

The phrase "expression of antisense RNA" refers to the transcription of a DNA to produce a first RNA molecule capable of hybridizing to a second RNA molecule.

The term "homology" refers to the level of similarity between two or more nucleic acid or amino acid sequences in terms of percent of positional identity (i.e., sequence similarity or identity). Homology also refers to the concept of similar functional properties among different nucleic acids or proteins.

The term "heterologous" refers to the relationship between two or more nucleic acid or protein sequences that are derived from different sources. For example, a promoter is heterologous with respect to a coding sequence if such a combination is not normally found in nature. In addition, a particular sequence may be "heterologous" with respect to a cell or organism into which it is inserted (i.e., does not naturally occur in that particular cell or organism).

The term "hybridization" refers to the ability of a first strand of nucleic acid to join with a second strand via hydrogen bond base pairing when the two nucleic acid strands have sufficient sequence identity. Hybridization occurs when the two nucleic acid molecules anneal to one another under appropriate conditions.

The phrase "operably linked" refers to the functional spatial arrangement of two or more nucleic acid regions or nucleic acid sequences. For example, a promoter region may be positioned relative to a nucleic acid sequence such that transcription of a nucleic acid sequence is directed by the promoter region. Thus, a promoter region is "operably linked" to the nucleic acid sequence.

The term or phrase "promoter" or "promoter region" refers to a nucleic acid sequence, usually found upstream (5') to a coding sequence, that is capable of directing transcription of a nucleic acid sequence into mRNA. The promoter or promoter region typically provides a recognition site for RNA polymerase and the other factors necessary for proper initiation of transcription. As contemplated herein, a promoter or promoter region includes variations of promoters derived by inserting or deleting regulatory regions, subjecting the promoter to random or site-directed mutagenesis, etc. The activity or strength of a promoter may be measured in terms of the amounts of RNA it produces, or the amount of protein accumulation in a cell or tissue, relative to a promoter whose transcriptional activity has been previously assessed.

The phrase "5' UTR" refers to the untranslated region of DNA upstream, or 5' of the coding region of a gene.

The phrase "3' UTR" refers to the untranslated region of DNA downstream, or 3' of the coding region of a gene.

The phrase "recombinant vector" refers to any agent such as a plasmid, cosmid, virus, autonomously replicating sequence, phage, or linear single-stranded, circular single-stranded, linear double-stranded, or circular double-stranded DNA or RNA nucleotide sequence. The recombinant vector may be derived from any source and is capable of genomic integration or autonomous replication.

The phrase "regulatory sequence" refers to a nucleotide sequence located upstream (5'), within, or downstream (3') to a coding sequence. Transcription and expression of the coding sequence is typically impacted by the presence or absence of the regulatory sequence.

The phrase "substantially homologous" refers to two sequences which are at least about 90% identical in sequence, as measured by the BestFit program described herein (Version 10; Genetics Computer Group, Inc., University of Wisconsin Biotechnology Center, Madison, Wis.), using default parameters.

The term "transformation" refers to the introduction of nucleic acid into a recipient host. The term "host" refers to bacteria cells, fungi, animals or animal cells, plants or seeds, or any plant parts or tissues including plant cells, protoplasts, calli, roots, tubers, seeds, stems, leaves, seedlings, embryos,.and pollen.

As used herein, the phrase "transgenic plant" refers to a plant having an introduced nucleic acid stably introduced into a genome of the plant, for example, the nuclear or plastid genomes.

As used herein, the phrase "substantially purified" refers to a molecule separated from substantially all other molecules normally associated with it in its native state. More preferably a substantially purified molecule is the predominant species present in a preparation. A substantially purified molecule may be greater than about 60% free, preferably about 75% free, more preferably about 90% free, and most preferably about 95% free from the other molecules (exclusive of solvent) present in the natural mixture. The phrase "substantially purified" is not intended to encompass molecules present in their-native state.

DETAILED DESCRIPTION OF THE PREFERRED EMBODIMENTS

The present invention provides promoters capable of transcribing a heterologous structural nucleic acid sequence in a seed, and methods of modifying, producing, and using the same. The present invention also provides compositions, transformed host cells, and plants containing seed specific promoters, and methods for preparing and using the same.

Nucleic Acid Molecules

The present invention provides nucleic acid molecules comprising a sequence selected from the group consisting of SEQ ID NOs: 1, 2, 3, 4, 9, 10, and 11, and complements thereof. SEQ ID NO: 5 represents a reported USP promoter.

Nucleic acid hybridization is a technique well known to those of skill in the art of DNA manipulation. The hybridization property of a given pair of nucleic acids is an indication of their similarity or identity.

Low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C.

High stringency conditions may be used to select for nucleic acid sequences with higher degrees of identity to the disclosed nucleic acid sequences (Sambrook et al., 1989).

The high stringency conditions typically involve nucleic acid hybridization in about 2× to about 10×SSC (diluted from a 20×SSC stock solution containing 3 M sodium chloride and 0.3 M sodium citrate, pH 7.0 in distilled water), about 2.5× to about 5× Denhardt's solution (diluted from a 50× stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70° C. for several hours to overnight. The high stringency conditions are preferably provided by 6×SSC, 5× Denhardt's solution, 100 mg/mL fish sperm DNA, and 0.1% (w/v) SDS, with an incubation at 55° C. for several hours.

The hybridization is generally followed by several wash steps. The wash compositions generally comprise 0.5× to about 10×SSC, and 0.01% (w/v) to about 0.5% (w/v) SDS with a 15 minute incubation at about 20° C. to about 70° C. Preferably, the nucleic acid segments remain hybridized after washing at least one time in 0.1×SSC at 65° C.

The nucleic acid molecules of the present invention preferably hybridize, under high stringency conditions, with a nucleic acid molecule having the sequence selected from the group consisting of SEQ ID NOs: 1, 2, 3, 4, 9, 10, and 11, and complements thereof. In a preferred embodiment, a nucleic acid molecule of the present invention hybridizes, under high stringency conditions, with a nucleic acid molecule comprising SEQ ID NO: 1. In a preferred embodiment, a nucleic acid molecule of the present invention hybridizes, under high stringency conditions, with a nucleic acid molecule comprising SEQ ID NO: 2. In a preferred embodiment, a nucleic acid molecule of the present invention hybridizes, under high stringency conditions, with a nucleic acid molecule comprising SEQ ID NO: 3. In a preferred embodiment, a nucleic acid molecule of the present invention hybridizes, under high stringency conditions, with a nucleic acid molecule comprising SEQ ID NO: 4. In a preferred embodiment, a nucleic acid molecule of the present invention hybridizes, under high stringency conditions, with a nucleic acid molecule comprising SEQ ID NO: 9. In a preferred embodiment, a nucleic acid molecule of the present invention hybridizes, under high stringency conditions, with a nucleic acid molecule comprising SEQ ID NO: 10. In a preferred embodiment, a nucleic acid molecule of the present invention hybridizes, under high stringency conditions, with a nucleic acid molecule comprising SEQ ID NO: 11.

In a preferred embodiment, a nucleic acid molecule of the present invention comprises a nucleic acid sequence that has a sequence identity to SEQ ID NO: 1 of greater than about 85.5%, or greater than about 87, 88, 89, 90, 91, 92, 93, 94, 95, 96, 97, 98, or about 99%.

In a preferred embodiment, a nucleic acid molecule of the present invention comprises a nucleic acid sequence that has a sequence identity to SEQ ID NO: 2 of greater than about 85.5%, or greater than about 87, 88, 89, 90, 91, 92, 93, 94, 95, 96, 97, 98, or about 99%.

In a preferred embodiment, a nucleic acid molecule of the present invention comprises a nucleic acid sequence that has a sequence identity to SEQ ID NO: 3 of greater than about 97.1%, 98, 98.5, or greater than about 99%.

In a preferred embodiment, a nucleic acid molecule of the present invention comprises a nucleic acid sequence that has a sequence identity to SEQ ID NO: 4 of greater than about 96.4%, 97, 98, or about 99%.

The percent of sequence identity is preferably determined using the following method. A sequence is converted to EditSeq DNA sequence files using EditSeq application program in the Dnastar software package (DNASTAR, Inc., Madison, Wis.). Converted files are imported into the Megalign application program of the Dnastar software package. The imported sequences are aligned using the Clustal method at the default setting with weighted residue weight table. This method is used to determine the percent identity of the promoter sequences of the present invention to other sequences and to each other.

An alternative method for determining percent identity uses the "Best Fit" or "Gap" program of the Sequence Analysis Software Package™ (Version 10; Genetics Computer Group, Inc., University of Wisconsin Biotechnology Center, Madison, Wis.). "Gap" utilizes the algorithm of Needleman and Wunsch (1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, 1981; Smith et al., 1983). The percent identity is most preferably determined using the "Best Fit" program using default parameters.

The present invention also provides nucleic acid molecule fragments that exhibit a percent identity to any of SEQ ID NOs: 1, 2, 3, 4, 9, 10, and 11, and complements thereof that is greater than the percent identity the fragments show to SEQ ID NO: 5. In a preferred embodiment, the percent identity of a fragment to any of SEQ ID NOs: 1 through 4 is at least about 1% greater than the percent identity of that fragment to SEQ ID NO: 5, and preferably is at least about 2, 3, 4, 5, 10, 15, 20, or about 30% greater.

In an embodiment, the fragments are between about 50 and about 600 consecutive nucleotides, about 50 and about 550 consecutive nucleotides, about 50 and about 500 consecutive nucleotides, about 50 and about 450 consecutive nucleotides, about 50 and about 400 consecutive nucleotides, about 50 and about 350 consecutive nucleotides, about 50 and about 300 consecutive nucleotides, about 50 and about 250 consecutive nucleotides, about 50 and about 200 consecutive nucleotides, about 50 and about 150 consecutive nucleotides, about 50 and about 100, about 15 to about 100, about 15 to about 50, or about 15 to about 25 consecutive nucleotides of a nucleic molecule of the present invention.

In another embodiment, the fragment comprises at least about 15, 20, 30, 40, 50, 60, 70, 80, 90, 100, 150, 200, 250, 300, 350, 400, 450, 500, 550, 600, or about 650 consecutive nucleotides of a nucleic acid sequence of the present invention.

The present invention contemplates nucleic acid sequences encoding polypeptides having the enzyme activity of the steroid pathway enzymes squalene epoxidase, sterol methyl transferase I, sterol C4 demethylase, obtusifoliol C14 α demethylase, sterol C5 desaturase, and sterol methyl transferase II.

Squalene epoxidase (also called squalene monooxygenase) catalyzes the conversion of squalene to squalene epoxide (2,3-oxidosqualene), a precursor to the initial sterol molecule in phytosterol biosynthetic pathway, cycloartenol. This is the first reported step in the pathway where oxygen is required for activity. The formation of squalene epoxide is also the last common reported step in sterol biosynthesis of animals, fungi, and plants. Recently, several homologues of *Arabidopsis* and *Brassica* squalene epoxidase genes were reported (Schafer, U. A., Reed, D. W., Hunter, D. G., Yao, K., Weninger, A. M., Tsang, E. W., Reaney, M. J., MacKenzie, S. L., and Covello, P. S. (1999), *Plant Mol. Biol.*, 39(4):721-728). The same authors also have PCT application disclosing the use of antisense technology with squalene epoxidase to elevate squalene levels in plants (WO 97/34003).

Squalene Epoxidase, also known as squalene monooxygenase is enzyme reference number 1.14.99.7, *Enzyme Nomenclature*, 1992, p. 146.

Several squalene epoxidase enzymes are known to the art. These include *Arabidopsis* squalene epoxidase protein sequence Accession No. AC004786 *Arabidopsis* squalene epoxidase Accession No. N64916, and *Arabidopsis* squalene epoxidase Accession No. T44667. Japanese Patent Application No. 07194381 A, discloses a DNA encoding a mammalian squalene epoxidase.

An additional aspect of the present invention is the recombinant constructs and vectors comprising nucleic acid sequences encoding squalene epoxidase, as well as a method of producing the novel squalene epoxidase, comprising culturing a host cell transformed with the novel constructs or vectors for a time and under conditions conductive to the production of the squalene epoxidase, and recovering the squalene epoxidase produced thereby.

S-adenosyl L-methionine:sterol C24 methyl transferases (SMT1 and SMT2) catalyze the transfer of a methyl group from a cofactor, S-adenosyl-L-methionine, to the C24 center of the sterol side chain (Bach, T. J. and Benveniste, P. (1997), *Prog. Lipid Res.*, 36:197-226). SMT in higher plant cells are responsible for their capability to produce a mixture of 24-methyl and 24-ethyl sterols (Schaffer, A., Bouvier-Navé, Benveniste, P., Schaller, H. (2000) *Lipids*, 35:263-269). Functional characterization of the SMT using a yeast erg6 expression system demonstrated unambiguously that an SMT1 sequence encodes a cycloartenol-C24-methyltransferase and a SMT2 sequence encodes a C24-methylene lophenol-C24-methyltransferase in a given plant species (Bouvier-Navé, P., Husselstein, T., and Benveniste, P. (1998), *Eur. J. Biochem.*, 246:518-529). Several plant genes coding for SMT1 and SMT2 have been reported and reviewed (Schaffer, A., Bouvier-Navé, Benveniste, P., Schaller, H. (2000) *Lipids*, 35:263-269). Transgenic plants expressing homologues of either SMT1 or SMT2 have been studied (Schaffer, A., Bouvier-Navé, Benveniste, P., Schaller, H. (2000) *Lipids*, 35:263-269). The use of these genes to modify plant sterol composition are also covered by two patent applications (WO 98/45457 and WO 00/61771).

Sterol methyl transferase I enzymes known in the art are useful in the present invention. Exemplary sequences include the known Arabidopsis sterol methyl transferase I protein sequence Accession No. U71400 (disclosure SEQ ID NO: 19), the known tobacco sterol methyl transferase I protein sequence Accession No. U81312 (disclosure SEQ ID NO: 20) and *Ricinus communis* sterol C methyltransferase, *Eur. J. Biochem.*, 246(2):518-529 (1997). (Complete cds, Accession No. g2246457).

S-Adenosyl L-Methionine Sterol C24 Methyltransferase—A nucleic acid sequence encoding an *Arabidopsis thaliana* S-adenosyl-L-methionine sterol C24 methyltransferase has been published by Husselstein et al., (1996) *FEBS Letters* 381:87-92. $\Delta^{24}$ sterol methyltransferase is enzyme number 2.1.1.41, *Enzyme Nomenclature*, 1992, p. 160.

Sterol C4 demethylase catalyses the first of several demethylation reactions, which results in the removal of the two methyl groups at C4. While in animals and fungi the removal of the two C4 methyl groups occurs consecutively, in plants it has been reported that there are other steps between the first and second C4 demethylations (Bach, T. J. and Benveniste, P. (1997), *Prog. Lipid Res.*, 36:197-226). The C4 demethylation is catalyzed by a complex of microsomal enzymes consisting of a monooxygenase, an $NAD^+$-dependent sterol 4-decarboxylase and an NADPH-dependent 3-ketosteroid reductase.

Sterol C14 demethylase catalyzes demethylation at C14 which removes the methyl group at C14 and creates a double bond at that position. In both fungi and animals, this is the first step in the sterol synthesis pathway. However, in higher plants, the 14α-methyl is removed after one C4 methyl has disappeared. Thus, while lanosterol is the substrate for C14 demethylase in animal and fungal cells, the plants enzyme uses obtusifoliol as substrate. Sterol C14 demethylation is mediated by a cytochrome P-450 complex. The mechanism of 14-methyl removal involves two oxidation steps leading to an alcohol, then an aldehyde at C29 and a further oxidative step involving a deformylation leading to formic acid and the sterol product with a typical 8, 14-diene (Aoyama, Y., Yoshida, Y., Sonoda, Y., and Sato, Y. (1989) *J. Biol. Chem.*, 264:18502-18505). Obtusifoliol C14 α-demethylase from *Sorghum bicolor* (L) Moench has been cloned using a gene-specific probe generated using PCR primers designed from an internal 14 amino acid sequence and was functionally expressed in *E. coli* (Bak, S., Kahn, R. A., Olsen, C. E., and Halkier, B. A. (1997) *The Plant Journal*, 11(2):191-201). Also, *Saccharomyces cerevisiae* CYP51A1 encoding lanosterol 14-demethylase was functionally expressed in tobacco (Grausem, B., Chaubet, N., Gigot, C., Loper, J. C., and Benveniste, P. (1995) *The Plant Journal*, 7(5):761-770).

Sterol C14 demethylase enzymes and sequences are known in the art. For example *Sorghum bicolor* obtusifoliol C14 α-demethylase CYP51 mRNA, described in *Plant J.*, 11(2): 191-201 (1997) (complete cds Acession No. U74319).

An additional aspect of the present invention is the recombinant constructs and vectors comprising nucleic acid sequences encoding the novel obtusifoliol C14 α-demethylase, as well as a method of producing the novel obtusifoliol C14 α-demethylase, comprising culturing a host cell transformed with the novel constructs or vectors for a time and under conditions conductive to the production of the obtusifoliol C14 α-demethylase, and recovering the obtusifoliol C14 α-demethylase produced thereby.

Sterol C5 desaturase catalyzes the insertion of the $\Delta^5$-double bond that normally occurs at the $\Delta^7$-sterol level, thereby forming a $\Delta^{5,7}$-sterol (Parks et al., Lipids, 30:227-230 (1995)). The reaction has been reported to involve the stereospecific removal of the 5α and 6α hydrogen atoms, biosynthetically derived from the 4 pro-R and 5 pro-S hydrogens of the (+) and (−) R-mevalonic acid, respectively (Goodwin, T. W. (1979) Annu. Rev. Plant Physiol., 30:369-404). The reaction is obligatorily aerobic and requires NADPH or NADH. The desaturase has been reported to be a multienzyme complex present in microsomes. It consists of the desaturase itself, cytochrome $b_5$ and a pyridine nucleotide-dependent flavoprotein. The $\Delta^5$-desaturase is reported to be a mono-oxygenase that utilizes electrons derived from a reduced pyridine nucleotide via cytochrome$^b$ (Taton, M., and Rahier, A. (1996) Arch. Biochem. Biophys., 325:279-288). An Arabidopsis thaliana cDNA encoding a sterol-C5 desaturase was cloned by functional complementation of a yeast mutant, erg3 defective in ERG3, the gene encoding the sterol C5 desaturase required for ergosterol biosynthesis (Gachotte D., Husselstein, T., Bard, M., Lacroute F., and Benveniste, P. (1996) The Plant Journal, 9(3):391-398). Known sterol C5 desaturase enzymes are useful in the present invention, including Arabidopsis sterol C5 desaturase protein sequence Accession No. X90454, disclosure SEQ ID NO: 22, and the Arabidopsis thaliana mRNA for sterol C5 desaturase described in The Plant J. 9(3):391-398 (1996) (complete cds Accession No. g1061037).

The NCBI (National Center for Biotechnology Information) database shows 37 sequences for sterol desaturase that are useful in the present invention. The following are exemplary of such sequences. From yeast: C5 sterol desaturase NP_013157 (Saccharomyces cerevisiae); hypothetical C5 sterol desaturase-fission T40027 (Schizosaccharomyces pombe); C5 sterol desaturase-fission T37759 (Schizosaccharomyces pombe); C5 sterol desaturase JQ1146 (Saccharomyces cerevisiae); C5 sterol desaturase BAA21457 (schizosaccharomyces pombe); C5 sterol desaturase CAA22610 (Schizosaccharomyces pombe); putative C5 sterol desaturase CAA16898 (Schizosaccharomyces pombe); probable C5 sterol desaturase O13666 (erg3_schpo); C5 sterol desaturase P50860 (Erg3_canga); C5 sterol desaturase P32353 (erg3_yeast); C5,6 desaturase AAC99343 (Candida albicans); C5 sterol desaturase BAA20292 (Saccharomyces cerevisiae); C5 sterol desaturase AAB39844 (Saccharomyces cerevisiae); C5 sterol desaturase AAB29844 (Saccharomyces cerevisiae); C5 sterol desaturase CAA64303 (Saccharomyces cerevisiae); C5 sterol desaturase AAA34595 (Saccharomyces cerevisiae); C5 sterol desaturase AAA34594 (Saccharomyces cerevisiae). From plants: C5 sterol desaturase S71251 (Arabidopsis thaliana); putative sterol C5 desaturase AAF32466 (Arabidopsis thaliana); sterol C5 desaturase AAF32465 (Arabidopsis thaliana); putatuve sterol desaturase AAF22921 (Arabidopsis thaliana); $\Delta^7$-sterol C5 desaturase (Arabidopsis thaliana); sterol C5,6 desaturase homolog AAD20458 (Nicotiana tabacum); sterol C5 desaturase AAD12944 (Arabidopsis thaliana); sterol C5,6 desaturase AAD04034 (Nicotiana tabacum); sterol C5 desaturase CAA62079 (Arabidopsis thaliana). From mammals: sterol C5 desaturase (Mus musculus) BAA33730; sterol C5 desaturase BAA33729 (Homo sapiens); lathosterol oxidase CAB65928 (Leishmania major); lathosterol oxidase (lathosterol C5 desaturase) O88822 (Mus musculus); lathosterol C5 desaturase O75845 (Homo sapiens); $\Delta^7$-sterol C5 desaturase AAF00544 (Homo sapiens). Others: fungal sterol C5 desaturase homolog BAA18970 (Homo sapiens).

For DNA sequences encoding a sterol-C5 desaturase useful in the present invention, the NCBI_nucleotide search for "sterol desaturase" came up with 110 sequences. The following are exemplary of such sequences. NC_001139 (Saccharomyces cerevisiae); NC_001145 (Saccharomyces cerevisiae); NC_001144 (Saccharomyces cerevisiae); AW700015 (Physcomitrella patens); AB004539 (Schizosaccharomyces pombe); and AW596303 (Glycine max); AC012188 (Arabidopsis thaliana).

The combination of introduction of an HMG-CoA reductase gene along with a sterol methyl transferase II gene into a cell serves to reduce steroid pathway intermediate compound accumulation in addition to reducing the accumulation of 24-methyl sterols such as campesterol.

Known sterol methyl transferase II enzymes are useful in the present invention, including Arabidopsis sterol methyl transferase II protein sequence (complete mRNA cds from FEBS Lett. 381(12):87-92 (1996) Accession No. X89867), disclosure SEQ ID NO: 21.

Recombinant constructs encoding any of the forgoing enzymes affecting the steroid biosynthetic pathway can be incorporated into recombinant vectors comprising the recombinant constructs comprising the isolated DNA molecules. Such vectors can be bacterial or plant expression vectors.

In a preferred embodiment, any of the plants or organisms of the present invention are transformed with a nucleic acid of the present invention and a gene encoding a member selected from the group consisting of squalene epoxidase, sterol methyl transferase I, sterol C4 demethylase, obtusifoliol C14 α-demethylase, sterol C5 desaturase, and sterol methyl transferase II. In a preferred embodiment, a plant or organism of the present invention is transformed with one or more of SEQ ID NOs: 1-5 and a gene encoding a member selected from the group consisting of squalene epoxidase, sterol methyl transferase I, sterol C4 demethylase, obtusifoliol C14 α-demethylase, sterol C5 desaturase, and sterol methyl transferase II. In a further preferred embodiment, a plant or organism of the present invention is transformed with one or more of SEQ ID NOs: 1-5, a gene encoding a member selected from the group consisting of squalene epoxidase, sterol methyl transferase I, sterol C4 demethylase, obtusifoliol C14 α-demethylase, sterol C5 desaturase, and sterol methyl transferase II, and one or more genes encoding a tocopherol pathway enzyme as disclosed elsewhere herein. In a further preferred embodiment, a plant or organism of the present invention is transformed with one or more of SEQ ID NOs: 1-5, two genes encoding a member selected from the group consisting of squalene epoxidase, sterol methyl transferase I, sterol C4 demethylase, obtusifoliol C14 α-demethylase, sterol C5 desaturase, and sterol methyl transferase II, and two genes encoding a tocopherol pathway enzyme as disclosed elsewhere herein. Any of the above combinations of tocopherol and sterol biosynthesis genes can be introduced into a plant on one or more constructs or vectors, as is known in the art and described herein.

Promoters

In one embodiment any of the disclosed nucleic acid molecules may be promoters. In a preferred embodiment, the promoter is tissue or organ specific, and preferably seed specific. In a particularly preferred embodiment the promoter preferentially expresses associated structural genes in the endosperm or embryo. In a preferred embodiment, the promoter is a USP promoter. In a particularly preferred embodiment, the promoter is a *Vicia faba* USP promoter.

In one aspect, a promoter is considered tissue or organ specific if the level of an mRNA in that tissue or organ is expressed at a level that is at least 10 fold higher, preferably at least 100 fold higher or at least 1,000 fold higher than another tissue or organ. The level of mRNA can be measured either at a single time point or at multiple time points and as such the fold increase can be average fold increase or an extrapolated value derived from experimentally measured values. As it is a comparison of levels, any method that measures mRNA levels can be used. In a preferred aspect, the tissue or organs compared are a seed or seed tissue with a leaf or leaf tissue. In another preferred aspect, multiple tissues or organs are compared. A preferred multiple comparison is a seed or seed tissue compared with 2, 3, 4, or more tissues or organs selected from the group consisting of floral tissue, floral apex, pollen, leaf, embryo, shoot, leaf primordia, shoot apex, root, root tip, vascular tissue and cotyledon. As used herein, examples of plant organs are seed, leaf, root, etc. and example of tissues are leaf primordia, shoot apex, vascular tissue, etc.

The activity or strength of a promoter may be measured in terms of the amount of mRNA or protein accumulation it specifically produces, relative to the total amount of mRNA or protein. The promoter preferably expresses an operably linked nucleic acid sequence at a level greater than about 2.5%; more preferably greater than about 5, 6, 7, 8, or about 9%; even more preferably greater than about 10, 11, 12, 13, 14, 15, 16, 17, 18, or about 19%, and most preferably greater than about 20% of the total mRNA.

Alternatively, the activity or strength of a promoter may be expressed relative to a well-characterized promoter (for which transcriptional activity was previously assessed). For example, a promoter of interest may be operably linked to a reporter sequence (e.g. GUS) and introduced into a specific cell type. A known promoter may be similarly prepared and introduced into the same cellular context. Transcriptional activity of the promoter of interest is then determined by comparing the amount of reporter expression, relative to the known promoter. The cellular context is preferably soybean.

Structural Nucleic Acid Sequences

The promoters of the present invention may be operably linked to a structural nucleic acid sequence that is heterologous with respect to the promoter. The structural nucleic acid sequence may generally be any nucleic acid sequence for which an increased level of transcription is desired. The structural nucleic acid sequence preferably encodes a polypeptide that is suitable for incorporation into the diet of a human or an animal or provides some other agriculturally important feature.

Suitable structural nucleic acid sequences include, without limitation, those encoding seed storage proteins, fatty acid pathway enzymes, tocopherol biosynthetic enzymes, amino acid biosynthetic enzymes, steroid pathway enzymes, and starch branching enzymes.

Preferred seed storage proteins include zeins (U.S. Pat. Nos. 4,886,878; 4,885,357; 5,215,912; 5,589,616; 5,508,468; 5,939,599; 5,633,436; and 5,990,384; Patent Applications: WO 90/01869, WO 91/13993, WO 92/14822, WO 93/08682, WO 94/20628, WO 97/28247, WO 98/26064, and WO 99/40209), 7S proteins (U.S. Pat. Nos. 5,003,045 and 5,576,203), brazil nut protein (U.S. Pat. No. 5,850,024), phenylalanine free proteins (Patent Application: WO 96/17064), albumin (Patent Application: WO 97/35023), β-conglycinin (Patent Application: WO 00/19839), 11S (U.S. Pat. No. 6,107,051), α-hordothionin (U.S. Pat. Nos. 5,885,802 and 5,885,801), arcelin seed storage proteins (U.S. Pat. No. 5,270,200), lectins (U.S. Pat. No. 6,110,891), and glutenin (U.S. Pat. Nos. 5,990,389 and 5,914,450).

Preferred fatty acid pathway enzymes include thioesterases (U.S. Pat. Nos. 5,512,482; 5,530,186; 5,945,585; 5,639,790; 5,807,893; 5,955,650; 5,955,329; 5,759,829; 5,147,792; 5,304,481; 5,298,421; 5,344,771; and 5,760,206), and desaturases (U.S. Pat. Nos. 5,689,050; 5,663,068; 5,614,393; 5,856,157; 6,117,677; 6,043,411; 6,194,167; 5,705,391; 5,663,068; 5,552,306; 6,075,183; 6,051,754; 5,689,050; 5,789,220; 5,057,419; 5,654,402; 5,659,645; 6,100,091; 5,760,206; 6,172,106; 5,952,544; 5,866,789; 5,443,974; and 5,093,249). Preferred tocopherol biosynthetic enzymes include tyrA, slr1736, ATPT2, dxs, dxr, GGPPS, HPPD, GMT, MT1, tMT2, AANT1, slr1737, and an antisense construct for homogentisic acid dioxygenase (Kridl et al., Seed Sci. Res., 1:209:219 (1991); Keegstra, Cell, 56(2):247-53 (1989); Nawrath, et al., Proc. Natl. Acad. Sci. (U.S.A.), 91:12760-12764 (1994); Xia et al., J. Gen. Microbiol., 138:1309-1316 (1992); Cyanobase www.kazusa.orjp/cyanobase; Lois et al., Proc. Natl. Acad. Sci. (U.S.A.), 95(5):2105-2110 (1998); Takahashi et al., Proc. Natl. Acad. Sci. (U.S.A.), 95(17), 9879-9884 (1998); Noffis et al., Plant Physiol., 117:1317-1323 (1998); Bartley and Scolnik, Plant Physiol., 104:1469-1470 (1994); Smith et al., Plant J., 11:83-92 (1997); WO 00/32757; WO 00/10380; Saint Guily, et al., Plant Physiol., 100(2):1069-1071 (1992); Sato et al., J. DNA Res., 7(1):31-63 (2000)).

Various genes and their encoded proteins that are involved in tocopherol biosynthesis are listed in Table 1 below.

TABLE 1

Genes and Encoded Proteins Involved in Tocopherol Biosynthesis

| Gene ID | Enzyme name |
| --- | --- |
| tyrA | Prephanate dehydrogenase |
| slr1736 | Phytylprenyl transferase from *Synechocystis* |
| ATPT2 | Phytylprenyl transferase from *Arabidopsis thaliana* |
| DXS | 1-Deoxyxylulose-5- phosphate synthase |
| DXR | 1-Deoxyxylulose-5- phosphate reductoisomerase |
| GGPPS | Geranylgeranyl pyrophosphate synthase |
| HPPD | p-Hydroxyphenylpyruvate dioxygenase |
| AANT1 | Adenylate transporter |
| slr1737 | Tocopherol cyclase |
| IDI | Isopentenyl diphosphate isomerase |
| GGH | Geranylgeranyl reductase |
| GMT | Gamma Methyl Transferase |

The "Gene IDs" given in Table 1 above identify the gene associated with the listed enzyme. Any of the Gene IDs listed in Table 1 appearing herein in the present disclosure refer to the gene encoding the enzyme with which the Gene ID is associated in Table 1.

Preferred amino acid biosynthetic enzymes include anthranilate synthase (U.S. Pat. No. 5,965,727; Patent Applications: WO 97/26366, WO 99/11800, and WO 99/49058), tryptophan decarboxylase (Patent Application: WO 99/06581), threonine decarboxylase (U.S. Pat. Nos. 5,534,421 and 5,942,660, Patent Application: WO 95/19442), threonine deaminase (Patent Applications: WO 99/02656, and WO 98/55601), and aspartate kinase (U.S. Pat. Nos. 5,367,110; 5,858,749; and 6,040,160).

Preferred starch branching enzymes include those set forth in U.S. Pat. Nos. 6,232,122 and 6,147, 279; and Patent Application WO 97/22703.

Alternatively, a promoter and structural nucleic acid sequence may be designed to down-regulate a specific nucleic acid sequence. This is typically accomplished by linking the promoter to a structural nucleic acid sequence that is oriented in the antisense direction. One of ordinary skill in the art is familiar with such antisense technology. Any nucleic acid sequence may be negatively regulated in this manner.

Targets of such regulation may include polypeptides that have a low content of essential amino acids, yet are expressed at a relatively high level in a particular tissue. For example, β-conglycinin and glycinin are expressed abundantly in seeds, but are nutritionally deficient with respect to essential amino acids. This antisense approach may also be used to effectively remove other undesirable proteins, such as antifeedants (e.g., lectins), albumin, and allergens, from plant-derived feed or to down-regulate catabolic enzymes involved in degradation of desired compounds such as essential amino acids.

Modified Structural Nucleic Acid Sequences

The promoters of the present invention may also be operably linked to a modified structural nucleic acid sequence that is heterologous with respect to the promoter. The structural nucleic acid sequence may be modified to provide various desirable features. For example, a structural nucleic acid sequence may be modified to increase the content of essential amino acids, enhance translation of the amino acid sequence, alter post-translational modifications (e.g., phosphorylation sites), transport a translated product to a compartment inside or outside of the cell, improve protein stability, insert or delete cell signaling motifs, etc.

In a preferred embodiment, the structural nucleic acid sequence is enhanced to encode a polypeptide having an increased content of at least one, and more preferably 2, 3, or 4 of the essential amino acids selected from the group consisting of histidine, lysine, methionine, and phenylalanine. Non-essential amino acids may also be added, as needed, for structural and nutritive enhancement of the polypeptide. Structural nucleic acid sequences particularly suited to such enhancements include those encoding native polypeptides that are expressed at relatively high levels, have a particularly low content of essential amino acids, or both. An example of such are the seed storage proteins, such as glycinin and β-conglycinin. Other suitable targets include arcelin, phaseolin, lectin, zeins, and albumin.

Codon Usage in Structural Nucleic Acid Sequences

Due to the degeneracy of the genetic code, different nucleotide codons may be used to code for a particular amino acid. A host cell often displays a preferred pattern of codon usage. Structural nucleic acid sequences are preferably constructed to utilize the codon usage pattern of the particular host cell. This generally enhances the expression of the structural nucleic acid sequence in a transformed host cell. Any of the above described nucleic acid and amino acid sequences may be modified to reflect the preferred codon usage of a host cell or organism in which they are contained. Modification of a structural nucleic acid sequence for optimal codon usage in plants is described in U.S. Pat. No. 5,689,052.

Other Modifications of Structural Nucleic Acid Sequences

Additional variations in the structural nucleic acid sequences described above may encode proteins having equivalent or superior characteristics when compared to the proteins from which they are engineered. Mutations may include deletions, insertions, truncations, substitutions, fusions, shuffling of motif sequences, and the like.

Mutations to a structural nucleic acid sequence may be introduced in either a specific or random manner, both of which are well known to those of skill in the art of molecular biology. A myriad of site-directed mutagenesis techniques exist, typically using oligonucleotides to introduce mutations at specific locations in a structural nucleic acid sequence. Examples include single strand rescue (Kunkel et al., 1985), unique site elimination (Deng and Nickloff, 1992), nick protection (Vandeyar et al., 1988), and PCR (Costa et al., 1996). Random or non-specific mutations may be generated by chemical agents (for a general review, see Singer and Kusmierek, 1982) such as nitrosoguanidine (Cerda-Olmedo et al., 1968; Guerola et al., 1971), and 2-aminopurine (Rogan and Bessman, 1970); or by biological methods such as passage through mutator strains (Greener et al., 1997). Additional methods of making the alterations described above are described by Ausubel et al. (1995); Bauer et al. (1985); Craik (1985); Frits Eckstein et al. (1982); Sambrook et al. (1989); Smith et al. (1981); and Osuna et al. (1994).

The modifications may result in either conservative or non-conservative changes in the amino acid sequence. Conservative changes are changes which do not alter the final amino acid sequence of the protein. In a preferred embodiment, the protein has between 5 and 500 conservative changes, more preferably between 10 and 300 conservative changes, even more preferably between 25 and 150 conservative changes, and most preferably between 5 and 25 conservative changes or between 1 and 5 conservative changes.

Non-conservative changes include additions, deletions, and substitutions which result in an altered amino acid sequence. In a preferred embodiment, the protein has between about 5 and about 500 non-conservative amino acid changes, more preferably between about 10 and about 300 non-conservative amino acid changes, even more preferably between about 25 and about 150 non-conservative amino acid changes, and most preferably between about 5 and about 25 non-conservative amino acid changes or between about 1 and about 5 non-conservative changes.

Modifications may be made to the protein sequences described herein and the nucleic acid sequences that encode them that maintain the desired properties of the molecule. The following is a discussion based upon changing the amino acid sequence of a protein to create an equivalent, or possibly an improved, second-generation molecule. The amino acid changes may be achieved by changing the codons of the structural nucleic acid sequence, according to the codons given in Table 2.

TABLE 2

| Codon degeneracy of amino acids | | | | | |
|---|---|---|---|---|---|
| Amino Acid | One letter | Three letter | Condons | | |
| Alanine | A | Ala | GCA | GCC | GCG GCT |
| Cysteine | C | Cys | TGC | TGT | |
| Aspartic acid | D | Asp | GAC | GAT | |
| Glutamic acid | E | Glu | GAA | GAG | |
| Phenylalanine | F | Phe | TTC | TTT | |

TABLE 2-continued

Codon degeneracy of amino acids

| Amino Acid | One letter | Three letter | Condons | | | |
|---|---|---|---|---|---|---|
| Glycine | G | Gly | GGA | GGC | GGG | GGT |
| Histidine | H | His | CAC | CAT | | |
| Isoleucine | I | Ile | ATA | ATC | ATT | |
| Lysine | K | Lys | AAA | AAG | | |
| Leucine | L | Leu | TTA | TTG | CTA CTC | CTG CTT |
| Methionine | M | Met | ATG | | | |
| Asparagine | N | Asn | AAC | AAT | | |
| Proline | P | Pro | CCA | CCC | CCG CCT | |
| Glutamine | Q | Gln | CAA | CAG | | |
| Arginine | R | Arg | AGA | AGG | CGA CGC | CGG CGT |
| Serine | S | Ser | AGC | AGT | TCA TCC | TCG TCT |
| Threonine | T | Thr | ACA | ACC | ACG ACT | |
| Valine | V | Val | GTA | GTC | GTG GTT | |
| Tryptophan | W | Trp | TGG | | | |
| Tyrosine | Y | Tyr | TAC | TAT | | |

Certain amino acids may be substituted for other amino acids in a protein sequence without appreciable loss of the desired activity. It is thus contemplated that various changes may be made in peptide sequences or protein sequences, or their corresponding nucleic acid sequences without appreciable loss of the biological activity.

In making such changes, the hydropathic index of amino acids may be considered. The importance of the hydropathic amino acid index in conferring interactive biological function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics. These are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

It is also understood in the art that the substitution of like amino acids may be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4).

It is understood that an amino acid may be substituted by another amino acid having a similar hydrophilicity score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

As outlined above, amino acid substitutions are therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine, and isoleucine. Changes which are not expected to be advantageous may also be used if these resulted proteins have improved rumen resistance, increased resistance to proteolytic degradation, or both improved rumen resistance and increased resistance to proteolytic degradation, relative to the unmodified polypeptide from which they are engineered. Alternatively, changes could be made to improve kinetics of metabolic enzymes.

In a preferred aspect, the protein modified is selected from seed storage proteins, fatty acid pathway enzymes, tocopherol biosynthetic enzymes, amino acid biosynthetic enzymes and starch branching enzymes.

Recombinant Vectors

Any of the promoters and structural nucleic acid sequences described above may be provided in a recombinant vector. A recombinant vector typically comprises, in a 5' to 3' orientation: a promoter to direct the transcription of a structural nucleic acid sequence and a structural nucleic acid sequence. Suitable promoters and structural nucleic acid sequences include those described herein. The recombinant vector may further comprise a 3' transcriptional terminator, a 3' polyadenylation signal, other untranslated nucleic acid sequences, transit and targeting nucleic acid sequences, selectable markers, enhancers, and operators, as desired.

Means for preparing recombinant vectors are well known in the art. Methods for making recombinant vectors particularly suited to plant transformation are described in U.S. Pat. Nos. 4,971,908; 4,940,835; 4,769,061; and 4,757,011. These types of vectors have also been reviewed (Rodriguez et al., 1988; Glick et al., 1993).

Typical vectors useful for expression of nucleic acids in higher plants are well known in the art and include vectors derived from the tumor-inducing (Ti) plasmid of *Agrobacterium tumefaciens* (Rogers et al., 1987). Other recombinant vectors useful for plant transformation, including the pCaM-VCN transfer control vector, have also been described (Fromm et al., 1985).

In one embodiment, multiple USP promoters are operably linked in a single construct to any combination of structural genes. In a preferred embodiment, any combination of 1, 2, 3, 4, 5, or 6 or more of nucleic acid molecules comprising SEQ ID NOs: 1, 2, 3, 4, 9, 10, and 11 can be operatively linked in a single construct to any combination of structural genes. In another aspect of the preferred embodiment, the nucleic acid molecules may be modified. Such modifications can include, for example, removal or addition of one or more structural or functional elements.

Additional Promoters in the Recombinant Vector

One or more additional promoters may also be provided in the recombinant vector. These promoters may be operably linked, for example, without limitation, to any of the structural nucleic acid sequences described above. Alternatively, the promoters may be operably linked to other nucleic acid sequences, such as those encoding transit peptides, selectable marker proteins, or antisense sequences.

These additional promoters may be selected on the basis of the cell type into which the vector will be inserted. Also, promoters which function in bacteria, yeast, and plants are all well taught in the art. The additional promoters may also be selected on the basis of their regulatory features. Examples of such features include enhancement of transcriptional activity, inducibility, tissue specificity, and developmental stage-specificity. In plants, promoters that are inducible, of viral or synthetic origin, constitutively active, temporally regulated, and spatially regulated have been described (Poszkowski et al., 1989; Odell et al., 1985; Chau et al., 1989).

Often-used constitutive promoters include the CaMV 35S promoter (Odell et al., 1985), the enhanced CAMV 35S promoter, the Figwort Mosaic Virus (FMV) promoter (Richins et al., 1987), the mannopine synthase (mas) promoter, the nopaline synthase (nos) promoter, and the octopine synthase (ocs) promoter.

Useful inducible promoters include promoters induced by salicylic acid or polyacrylic acids (PR-1; Williams et al, 1992), induced by application of safeners (substituted benzenesulfonamide herbicides; Hershey and Stoner, 1991), heat-shock promoters (Ou-Lee et al., 1986; Ainley et al., 1990), a nitrate-inducible promoter derived from the spinach nitrite reductase structural nucleic acid sequence (Back et al., 1991), hormone-inducible promoters (Yamaguchi-Shinozaki et al., 1990; Kares et al., 1990), and light-inducible promoters associated with the small subunit of RuBP carboxylase and LHCP families (Kuhlemeier et al., 1989; Feinbaum et al., 1991; Weisshaar et al., 1991; Lam and Chua, 1990; Castresana et al., 1988; Schulze-Lefert et al., 1989).

Examples of useful tissue or organ specific promoters include β-conglycinin, (Doyle et al., 1986; Slighton and Beachy, 1987), and other seed specific promoters (Knutzon et al., 1992; Bustos et al., 1991; Lam and Chua, 1991). Plant functional promoters useful for preferential expression in seed include those from plant storage proteins and from proteins involved in fatty acid biosynthesis in oilseeds. Examples of such promoters include the 5' regulatory regions from such structural nucleic acid sequences as napin (Kridl et al., 1991), phaseolin, zein, soybean trypsin inhibitor, ACP, stearoyl-ACP desaturase, and oleosin. Seed-specific regulation is further discussed in EP 0 255 378.

Another exemplary seed specific promoter is a lectin promoter. The lectin protein in soybean seeds is encoded by a single structural nucleic acid sequence (Le1) that is only expressed during seed development. A lectin structural nucleic acid sequence and seed-specific promoter have been characterized and used to direct seed specific expression in transgenic tobacco plants (Vodkin et al., 1983; Lindstrom et al., 1990).

Particularly preferred additional promoters in the recombinant vector include the nopaline synthase (nos), mannopine synthase (mas), and octopine synthase (ocs) promoters, which are carried on tumor-inducing plasmids of Agrobacterium tumefaciens; the cauliflower mosaic virus (CaMV) 19S and 35S promoters; the enhanced CaMV 35S promoter; the Figwort Mosaic Virus (FMV) 35S promoter; the light-inducible promoter from the small subunit of ribulose-1,5-bisphosphate carboxylase (ssRUBISCO); the EIF-4A promoter from tobacco (Mandel et al., 1995); corn sucrose synthetase 1 (Yang and Russell, 1990); corn alcohol dehydrogenase 1 (Vogel et al., 1989); corn light harvesting complex (Simpson, 1986); corn heat shock protein (Odell et al., 1985); the chitinase promoter from Arabidopsis (Samac et al., 1991); the LTP (Lipid Transfer Protein) promoters from broccoli (Pyee et al., 1995); petunia chalcone isomerase (Van Tunen et al., 1988); bean glycine rich protein 1 (Keller et al., 1989); potato patatin (Wenzler et al., 1989); the ubiquitin promoter from maize (Christensen et al., 1992); and the actin promoter from rice (McElroy et al., 1990).

An additional promoter is preferably seed selective, tissue selective, constitutive, or inducible. The promoter is most preferably the nopaline synthase (nos), octopine synthase (ocs), mannopine synthase (mas), cauliflower mosaic virus 19S and 35S (CaMV19S, CaMV35S), enhanced CaMV (eCaMV), ribulose 1,5-bisphosphate carboxylase (ss-RUBISCO), figwort mosaic virus (FMV), CaMV derived AS4, tobacco RB7, wheat POX1, tobacco EIF-4, lectin protein (Lel), or rice RC2 promoter.

Recombinant Vectors Having Additional Structural Nucleic Acid Sequences

The recombinant vector may also contain one or more additional structural nucleic acid sequences. These additional structural nucleic acid sequences may generally be any sequences suitable for use in a recombinant vector. Such structural nucleic acid sequences include, without limitation, any of the structural nucleic acid sequences, and modified forms thereof, described above. The additional structural nucleic acid sequences may also be operably linked to any of the above described promoters. The one or more structural nucleic acid sequences may each be operably linked to separate promoters. Alternatively, the structural nucleic acid sequences may be operably linked to a single promoter (i.e., a single operon).

The additional structural nucleic acid sequences include, without limitation, those encoding seed storage proteins, fatty acid pathway enzymes, tocopherol biosynthetic enzymes, amino acid biosynthetic enzymes, and starch branching enzymes.

Preferred seed storage proteins include zeins (U.S. Pat. Nos. 4,886,878; 4,885,357; 5,215,912; 5,589,616; 5,508, 468; 5,939,599; 5,633,436; and 5,990,384; Patent Applications: WO 90/01869, WO 91/13993, WO 92/14822, WO 93/08682, WO 94/20628, WO 97/28247, WO 98/26064, and WO 99/40209), 7S proteins (U.S. Pat. Nos. 5,003,045 and 5,576,203), brazil nut protein (U.S. Pat. No. 5,850,024), phenylalanine free proteins (Patent Application: WO 96/17064), albumin (Patent Application: WO 97/35023), β-conglycinin (Patent Application: WO 00/19839), 11S (U.S. Pat. No. 6,107,051), α-hordothionin (U.S. Pat. Nos. 5,885,802 and 5,885,801) arcelin seed storage proteins (U.S.

Pat. No. 5,270,200) lectins (U.S. Pat. No. 6,110,891) and glutenin (U.S. Pat. Nos. 5,990,389 and 5,914,450).

Preferred fatty acid pathway enzymes include thioesterases (U.S. Pat. Nos. 5,512,482; 5,530,186; 5,945,585; 5,639,790; 5,807,893; 5,955,650; 5,955,329; 5,759,829; 5,147,792; 5,304,481; 5,298,421; 5,344,771; and 5,760,206), and desaturases (U.S. Pat. Nos. 5,689,050; 5,663,068; 5,614,393; 5,856,157; 6,117,677; 6,043,411; 6,194,167; 5,705,391; 5,663,068; 5,552,306; 6,075,183; 6,051,754; 5,689,050; 5,789,220; 5,057,419; 5,654,402; 5,659,645; 6,100,091; 5,760,206; 6,172,106; 5,952,544; 5,866,789; 5,443,974; and 5,093,249).

Preferred tocopherol biosynthetic enzymes include tyrA, slr1736, ATPT2, dxs, dxr, GGPPS, HPPD, GMT, MT1, tMT2, AANT1, slr1737, and an antisense construct for homogentisic acid dioxygenase (Kridl et al., Seed Sci. Res., 1:209:219 (1991); Keegstra, Cell, 56(2):247-53 (1989); Nawrath, et al., Proc. Natl. Acad. Sci. (U.S.A.), 91:12760-12764 (1994); Xia et al., J. Gen. Microbiol., 138:1309-1316 (1992); Cyanobase www.kazusa.or.jp/cyanobase; Lois et al., Proc. Natl. Acad. Sci. (U.S.A.), 95(5):2105-2110 (1998); Takahashi et al. Proc. Natl. Acad. Sci. (U.S.A.), 95(17): 9879-9884 (1998); Noffis et al., Plant Physiol., 117:1317-1323 (1998); Bartley and Scolnik, Plant Physiol., 104:1469-1470 (1994); Smith et al., Plant J., 11:83-92 (1997); WO 00/32757; WO 00/10380; Saint Guily, et al., Plant Physiol, 100(2):1069-1071 (1992); Sato et al., J. DNA Res., 7(1):31-63.(2000)).

Preferred amino acid biosynthetic enzymes include anthranilate synthase (U.S. Pat. No. 5,965,727, Patent Applications: WO 97/26366, WO 99/11800, and WO 99/49058), tryptophan decarboxylase (Patent Application: WO 99/06581), threonine decarboxylase (U.S. Pat. Nos. 5,534,421 and 5,942,660; Patent Application: WO 95/19442), threonine deaminase (Patent Applications WO 99/02656 and WO 98/55601), and aspartate kinase (U.S. Pat. Nos. 5,367,110; 5,858,749; and 6,040,160).

Preferred starch branching enzymes include those set forth in U.S. Pat. Nos. 6,232,122 and 6,147,279; and Patent Application WO 97/22703.

Alternatively, the second structural nucleic acid sequence may be designed to down-regulate a specific nucleic acid sequence. This is typically accomplished by operably linking the second structural amino acid, in an antisense orientation, with a promoter. One of ordinary skill in the art is familiar with such antisense technology. Any nucleic acid sequence may be negatively regulated in this manner. Preferable target nucleic acid sequences contain a low content of essential amino acids, yet are expressed at relatively high levels in particular tissues. For example, β-conglycinin and glycinin are expressed abundantly in seeds, but are nutritionally deficient with respect to essential amino acids. This antisense approach may also be used to effectively remove other undesirable proteins, such as antifeedants (e.g., lectins), albumin, and allergens, from plant-derived foodstuffs, or to down-regulate catabolic enzymes involved in degradation of desired compounds such as essential amino acids.

Selectable Markers

A vector or construct may also include a selectable marker. Selectable markers may also be used to select for plants or plant cells that contain the exogenous genetic material. Examples of such include, but are not limited to: a neo gene (Potrykus et al., 1985), which codes for kanamycin resistance and can be selected for using kanamycin, RptII, G418, hpt, etc.; a bar gene which codes for bialaphos resistance; a mutant EPSP synthase gene (Hinchee et al., 1988; Reynaerts et al., 1988); aadA (Jones et al., 1987) which encodes glyphosate resistance; a nitrilase gene which confers resistance to bromoxynil (Stalker et al., 1988); a mutant acetolactate synthase gene (ALS) which confers imidazolinone or sulphonylurea resistance (European Patent Application 154,204 (1985)), ALS (D'Halluin et al., 1992), and a methotrexate resistant DHFR gene (Thillet et al., 1988). The selectable marker is preferably GUS, green fluorescent protein (GFP), neomycin phosphotransferase II (nptII), luciferase (LUX), an antibiotic resistance coding sequence, or an herbicide (e.g., glyphosate) resistance coding sequence. The selectable marker is most preferably a kanamycin, hygromycin, or herbicide resistance marker.

A vector or construct may also include a screenable marker. Screenable markers may be used to monitor expression. Exemplary screenable markers include: a β-glucuronidase or uidA gene (GUS) which encodes an enzyme for which various chromogenic substrates are known (Jefferson, 1987); an R-locus gene, which encodes a product that regulates the production of anthocyanin pigments (red color) in plant tissues (Dellaporta et al., 1988); a β-lactamase gene (Sutcliffe et al., 1978), a gene which encodes an enzyme for which various chromogenic substrates are known (e.g., PADAC, a chromogenic cephalosporin); a luciferase gene (Ow et al., 1986); a xylE gene (Zukowsky et al., 1983) which encodes a catechol dioxygenase that can convert chromogenic catechols; an α-amylase gene (Ikatu et al., 1990); a tyrosinase gene (Katz et al., 1983) which encodes an enzyme capable of oxidizing tyrosine to DOPA and dopaquinone which in turn condenses to melanin; an α-galactosidase, which will turn a chromogenic α-galactose substrate.

Included within the term or phrase "selectable or screenable marker genes" are also genes which encode a secretable marker whose secretion can be detected as a means of identifying or selecting for transformed cells. Examples include markers which encode a secretable antigen that can be identified by antibody interaction, or even secretable enzymes which can be detected catalytically. Secretable proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

Other Elements in the Recombinant Vector

Various cis-acting untranslated 5' and 3' regulatory sequences may be included in the recombinant nucleic acid vector. Any such regulatory sequences may be provided in a recombinant vector with other regulatory sequences. Such combinations can be designed or modified to produce desirable regulatory features.

A 3' non-translated region typically provides a transcriptional termination signal, and a polyadenylation signal which functions in plants to cause the addition of adenylate nucleotides to the 3' end of the mRNA. These may be obtained from the 3' regions of the nopaline synthase (nos) coding sequence, a soybean 7Sα' storage protein coding sequence, the arcelin-5 coding sequence, the albumin coding sequence, and the pea ssRUBISCO E9 coding sequence. Typically, nucleic acid sequences located a few hundred base pairs downstream of the polyadenylation site serve to terminate transcription. These regions are required for efficient polyadenylation of transcribed mRNA.

Translational enhancers may also be incorporated as part of the recombinant vector. Thus the recombinant vector may preferably contain one or more 5' non-translated leader sequences which serve to enhance expression of the nucleic acid sequence. Such enhancer sequences may be desirable to increase or alter the translational efficiency of the resultant mRNA. Preferred 5' nucleic acid sequences include dSSU 5', PetHSP70 5', and GmHSP17.9 5' (U.S. Pat. No. 5,362,865).

The recombinant vector may further comprise a nucleic acid sequence encoding a transit peptide. This peptide may be useful for directing a protein to the extracellular space, a plastid, or to some other compartment inside or outside of the cell. (see, e.g., EP 0 218 571, U.S. Pat. Nos. 4,940,835; 5,88,624; 5,610,041; 5,618,988; and 6,107,060).

The structural nucleic acid sequence in the recombinant vector may comprise introns. The introns may be heterologous with respect to the structural nucleic acid sequence. Preferred introns include the rice actin intron and the corn HSP70 intron.

Fusion Proteins

Any of the above described structural nucleic acid sequences, and modified forms thereof, may be linked with additional nucleic acid sequences to encode fusion proteins. The additional nucleic acid sequence preferably encodes at least 1 amino acid, peptide, or protein. Many possible fusion combinations exist.

For instance, the fusion protein may provide a "tagged" epitope to facilitate detection of the fusion protein, such as GST, GFP, FLAG, or polyHIS. Such fusions preferably encode between 1 and 50 amino acids, more preferably between 5 and 30 additional amino acids, and even more preferably between 5 and 20 amino acids.

Alternatively, the fusion may provide regulatory, enzymatic, cell signaling, or intercellular transport functions. For example, a sequence encoding a plastid transit peptide may be added to direct a fusion protein to the chloroplasts within seeds. Such fusion partners preferably encode between 1 and 1000 additional amino acids, more preferably between 5 and 500 additional amino acids, and even more preferably between 10 and 250 amino acids.

Sequence Analysis

In the present invention, sequence similarity or identity is preferably determined using the "Best Fit" or "Gap" programs of the Sequence Analysis Software Package™ (Version 10; Genetics Computer Group, Inc., University of Wisconsin Biotechnology Center, Madison, Wis.). "Gap" utilizes the algorithm of Needleman and Wunsch (1970) to find the alignment of 2 sequences that maximizes the number of matches and minimizes the number of gaps. "BestFit" performs an optimal alignment of the best segment of similarity between two sequences. Optimal alignments are found by inserting gaps to maximize the number of matches using the local homology algorithm of Smith and Waterman (Smith and Waterman, 1981; Smith et al., 1983).

The Sequence Analysis Software Package described above contains a number of other useful sequence analysis tools for identifying homologues of the presently disclosed nucleotide and amino acid sequences. For example, the "BLAST" program searches for sequences similar to a query sequence (either peptide or nucleic acid) in a specified database (e.g., sequence databases maintained at the National Center for Biotechnology Information (NCBI) in Bethesda, Md.); "FastA" (Lipman and Pearson, 1985; see, also, Pearson and Lipman, 1988; Pearson, 1990) performs a Pearson and Lipman search for similarity between a query sequence and a group of sequences of the same type (nucleic acid or protein); "TfastA" performs a Pearson and Lipman search for similarity between a protein query sequence and any group of nucleotide sequences (it translates the nucleotide sequences in all 6 reading frames before performing the comparison); "FastX" performs a Pearson and Lipman search for similarity between a nucleotide query sequence and a group of protein sequences, taking frameshifts into account. "TfastX" performs a Pearson and Lipman search for similarity between a protein query sequence and any group of nucleotide sequences, taking frameshifts into account (it translates both strands of the nucleic acid sequence before performing the comparison).

Probes and Primers

Short nucleic acid sequences having the ability to specifically hybridize to complementary nucleic acid sequences may be produced and utilized in the present invention. Such short nucleic acid molecules may be used as probes to identify the presence of a complementary nucleic acid sequence in a given sample. Thus, by constructing a nucleic acid probe that is complementary to a small portion of a particular nucleic acid sequence, the presence of that nucleic acid sequence may be detected and assessed.

Alternatively, the short nucleic acid sequences may be used as oligonucleotide primers to amplify or mutate a complementary nucleic acid sequence using PCR technology. These primers may also facilitate the amplification of related complementary nucleic acid sequences (e.g., related nucleic acid sequences from other species).

Short nucleic acid sequences may be used as primers and specifically as PCR primers. A PCR probe is a nucleic acid molecule capable of initiating a polymerase activity while in a double-stranded structure with another nucleic acid. Various methods for determining the structure of PCR primers and PCR techniques exist in the art. Computer generated searches using programs such as Primer3 (www.genome.wi.mit.edu/cgi-bin/primer/primer3.cgi), STSPipeline (www-genome.wi.mit.edu/cgi-bin/www.STS_Pipeline), or GeneUp (Pesole et al., 1998), for example, can be used to identify potential PCR primers.

Any of the nucleic acid sequences disclosed herein may be used as a primer or probe. Use of these probes or primers may greatly facilitate the identification of transgenic plants which contain the presently disclosed promoters and structural nucleic acid sequences. Such probes or primers may also be used to screen cDNA or genomic libraries for additional nucleic acid sequences related to or sharing homology with the presently disclosed promoters and structural nucleic acid sequences.

A primer or probe is generally complementary to a portion of a nucleic acid sequence that is to be identified, amplified, or mutated and of sufficient length to form a stable and sequence-specific duplex molecule with its complement. The primer or probe preferably is about 10 to about 200 nucleotides long, more preferably is about 10 to about 100 nucleotides long, even more preferably is about 10 to about 50 nucleotides long, and most preferably is about 14 to about 30 nucleotides long.

The primer or probe may, for example without limitation, be prepared by direct chemical synthesis, by PCR (U.S. Pat. Nos. 4,683,195 and 4,683,202), or by excising the nucleic acid specific fragment from a larger nucleic acid molecule.

Transgenic Plants and Transformed Plant Host Cells

The present invention is also directed to transgenic plants and transformed host cells which comprise a promoter operably linked to a heterologous structural nucleic acid sequence. Other nucleic acid sequences may also be introduced into the plant or host cell along with the promoter and structural nucleic acid sequence. These other sequences may include 3' transcriptional terminators, 3' polyadenylation signals, other untranslated nucleic acid sequences, transit or targeting sequences, selectable markers, enhancers, and operators. Preferred nucleic acid sequences of the present invention, including recombinant vectors, structural nucleic acid sequences, promoters, and other regulatory elements, are described above.

In a preferred embodiment, the transgenic plants and transformed host cells comprise a USP promoter from *Vicia faba*. In a most preferred embodiment, the transgenic plants and transformed host cells comprise any nucleic acid molecule of the present invention as described herein, including a nucleic acid sequence selected from the group consisting of SEQ ID NOs: 1, 2, 3, 4, 9, 10, and 11, and complements thereof.

In a particularly preferred embodiment, the transgenic plant of the present invention is a soybean plant. In a preferred embodiment, a soybean plant of the present invention comprises one or more introduced nucleic acid molecules of the present invention. In a preferred embodiment, a transformed soybean plant of the present invention comprises a nucleic acid molecule selected from the group consisting of SEQ ID NOs: 1, 2, 3, 4, 5, 9, 10, and 11. In a preferred embodiment a transformed soybean plant of the present invention comprises a nucleic acid molecule comprising SEQ ID NO: 4. In a preferred embodiment a transformed soybean plant of the present invention comprises a nucleic acid molecule comprising SEQ ID NO: 5.

In some embodiments of the present invention, one or more components of a plant, cell, or organism are compared to a plant, cell, or organism having a "similar genetic background." In a preferred aspect, a "similar genetic background" is a background where the organisms being compared share about 50% or greater of their nuclear genetic material. In a more preferred aspect a similar genetic background is a background where the organisms being compared share about 75% or greater, even more preferably about 90% or greater of their nuclear genetic material. In another even more preferable aspect, a similar genetic background is a background where the organisms being compared are plants, and the plants are isogenic except for any genetic material originally introduced using plant transformation techniques.

Means for preparing such recombinant vectors are well known in the art. For example, methods for making recombinant vectors particularly suited to plant transformation are described in U.S. Pat. Nos. 4,971,908; 4,940,835; 4,769,061; and 4,757,011. These vectors have also been reviewed (Rodriguez et al., 1988; Glick et al., 1993).

Typical vectors useful for expression of nucleic acids in cells and higher plants are well known in the art and include vectors derived from the tumor-inducing (Ti) plasmid of *Agrobacterium tumefaciens* (Rogers et al., 1987). Other recombinant vectors useful for plant transformation have also been described (Fromm et al., 1985). Elements of such recombinant vectors include, without limitation, those discussed above.

A transformed host cell may generally be any cell that is compatible with the present invention. A transformed host plant or cell can be or derived from a monocotyledonous plant or a dicotyledonous plant including, but not limited to canola, crambe, maize, mustard, castor bean, sesame, cottonseed, linseed, soybean, *Arabidopsis* phaseolus, peanut, alfalfa, wheat, rice, oat, sorghum, rapeseed, rye, tritordeum, millet, fescue, perennial ryegrass, sugarcane, cranberry, papaya, banana, safflower, oil palms, flax, muskmelon, apple, cucumber, dendrobium, gladiolus, chrysanthemum, liliacea, cotton, eucalyptus, sunflower, *Brassica campestris, Brassica napus*, turfgrass, sugarbeet, coffee, and dioscorea (Christou, In: *Particle Bombardment for Genetic Engineering of Plants*, Biotechnology Intelligence Unit, Academic Press, San Diego, Calif. (1996)), with canola, maize, *Brassica campestris, Brassica napus*, rapeseed, soybean, safflower, wheat, rice, and sunflower preferred, and canola, rapeseed, maize, *Brassica campestris, Brassica napus*, soybean, sunflower, safflower, oil palms, and peanut more preferred. In a particularly preferred embodiment, the plant or cell is or derived from canola. In another particularly preferred embodiment, the plant or cell is or derived from *Brassica napus*. In another particularly preferred embodiment, the plant or cell is or derived from soybean.

The soybean cell or plant is preferably an elite soybean cell line. An "elite line" is any line that has resulted from breeding and selection for superior agronomic performance. Examples of elite lines are lines that are commercially available to farmers or soybean breeders such as HARTZ™ variety H4994, HARTZ™ variety H5218, HARTZ™ variety H5350, HARTZ™ variety H5545, HARTZ™ variety H5050, HARTZ™ variety H5454, HARTZ™ variety H5233, HARTZ™ variety H5488, HARTZ™ variety HLA572, HARTZ™ variety H6200, HARTZ™ variety H6104, HARTZ™ variety H6255, HARTZ™ variety H6586, HARTZ™ variety H6191, HARTZ™ variety H7440, HARTZ™ variety H4452 Roundup Ready™, HARTZ™ variety H4994 Roundup Ready™, HARTZ™ variety H4988 Roundup Ready™, HARTZ™ variety H5000 Roundup Ready™, HARTZ™ variety H5147 Roundup Ready™, HARTZ™ variety H5247 Roundup Ready™, HARTZ™ variety H5350 Roundup Ready™, HARTZ™ variety H5545 Roundup Ready™, HARTZ™ variety H5855 Roundup Ready™, HARTZ™ variety H5088 Roundup Ready™, HARTZ™ variety H5164 Roundup Ready™, HARTZ™ variety H5361 Roundup Ready™, HARTZ™ variety H5566 Roundup Ready™, HARTZ™ variety H5181 Roundup Ready™, HARTZ™ variety H5889 Roundup Ready™, HARTZ™ variety H5999 Roundup Ready™, HARTZ™ variety H6013 Roundup Ready™, HARTZ™ variety H6255 Roundup Ready™, HARTZ™ variety H6454 Roundup Ready™, HARTZ™ variety H6686 Roundup Ready™, HARTZ™ variety H7152 Roundup Ready™, HARTZ™ variety H7550 Roundup Ready™, HARTZ™ variety H8001 Roundup Ready™ (HARTZ SEED, Stuttgart, Ariz.); A0868, AG0901, A1553, A1900, AG1901, A1923, A2069, AG2101, AG2201, A2247, AG2301, A2304, A2396, AG2401, AG2501, A2506, A2553, AG2701, AG2702, A2704, A2833, A2869, AG2901, AG2902, AG3001, AG3002, A3204, A3237, A3244, AG3301, AG3302, A3404, A3469, AG3502, A3559, AG3601, AG3701, AG3704, AG3750, A3834, AG3901, A3904, A4045 AG4301, A4341, AG4401, AG4501, AG4601, AG4602, A4604, AG4702, AG4901, A4922, AG5401, A5547, AG5602, A5704, AG5801, AG5901, A5944, A5959, AG6101, QR4459, and QP4544 (Asgrow Seeds, Des Moines, Iowa); DeKalb variety CX445 (DeKalb, Ill.).

The present invention is also directed to a method of producing transformed plants which comprise, in a 5' to 3' orientation, a promoter operably linked to a heterologous structural nucleic acid sequence. Other sequences may also be introduced into plants along with the promoter and structural nucleic acid sequence. These other sequences may include 3' transcriptional terminators, 3' polyadenylation signals, other untranslated sequences, transit or targeting sequences, selectable markers, enhancers, and operators. Preferred recombinant vectors, structural nucleic acid sequences, promoters, and other regulatory elements including, without limitation, those described herein.

The method generally comprises the steps of selecting a suitable plant, transforming the plant with a recombinant vector, and obtaining the transformed host cell.

There are many methods for introducing nucleic acids into plants. Suitable methods include bacterial infection (e.g., *Agrobacterium*), binary bacterial artificial chromosome vectors, direct delivery of nucleic acids (e.g., via PEG-mediated transformation, desiccation/inhibition-mediated nucleic acid uptake, electroporation, agitation with silicon carbide fibers, and acceleration of nucleic acid coated particles, etc. (reviewed in Potrykus et al., 1991)).

Technology for introduction of nucleic acids into cells is well known to those of skill in the art. Methods can generally be classified into four categories: (1) chemical methods (Graham and van der Eb, 1973; Zatloukal et al., 1992); (2) physical methods such as microinjection (Capecchi, 1980), electroporation (Wong and Neumann, 1982; Fromm et al., 1985; U.S. Pat. No. 5,384,253), and particle acceleration (Johnston and Tang, 1994; Fynan et al., 1993); (3) viral vectors (Clapp, 1993; Lu et al., 1993; Eglitis and Anderson, 1988); and (4) receptor-mediated mechanisms (Curiel et al., 1992; Wagner et al., 1992). Alternatively, nucleic acids can be directly introduced into pollen by directly injecting a plant's reproductive organs (Zhou et al., 1983; Hess, 1987; Luo et al., 1988; Pena et al., 1987). In another aspect nucleic acids may also be injected into immature embryos (Neuhaus et al., 1987).

Regeneration, development, and cultivation of plants from transformed plant protoplast or explants is taught in the art (Weissbach and Weissbach, 1988; Horsch et al., 1985). Transformants are generally cultured in the presence of a selective media which selects for the successfully transformed cells and induces the regeneration of plant shoots (Fraley et al., 1983). Such shoots are typically obtained within 2 to 4 months.

Shoots are then transferred to an appropriate root-inducing medium containing the selective agent and an antibiotic to prevent bacterial growth. Many of the shoots will develop roots. These are then transplanted to soil or other media to allow the continued development of roots. The method, as outlined, will generally vary depending on the particular plant employed.

Preferably, the regenerated transgenic plants are self-pollinated to provide homozygous transgenic plants. Alternatively, pollen obtained from the regenerated transgenic plants may be crossed with non-transgenic plants, preferably inbred lines of agronomically important species. Conversely, pollen from non-transgenic plants may be used to pollinate the regenerated transgenic plants.

A transgenic plant may pass along the nucleic acid sequence encoding the enhanced gene expression to its progeny. The transgenic plant is preferably homozygous for the nucleic acid encoding the enhanced gene expression and transmits that sequence to all of its offspring upon as a result of sexual reproduction. Progeny may be grown from seeds produced by the transgenic plant. These additional plants may then be self-pollinated to generate a true breeding line of plants.

The progeny from these plants are evaluated, among other things, for gene expression. The gene expression may be detected by several common methods such as western blotting, northern blotting, immunoprecipitation, and ELISA.

Plants or agents of the present invention can be utilized in methods, for example without limitation, to obtain a seed that expresses a structural nucleic acid molecule in that seed, to obtain a seed enhanced in a product of a structural gene, to obtain meal enhanced in a product of a structural gene, to obtain feedstock enhanced in a product of a structural gene, and to obtain oil enhanced in a product of a structural gene Plants utilized in such methods may be processed. A plant or plant part may be separated or isolated from other plant parts. A preferred plant part for this purpose is a seed. It is understood that even after separation or isolation from other plant parts, the isolated or separated plant part may be contaminated with other plant parts. In a preferred aspect, the separated plant part is greater than about 50% (w/w) of the separated material, more preferably, greater than about 75% (w/w) of the separated material, and even more preferably greater than about 90% (w/w) of the separated material. Plants or plant parts of the present invention generated by such methods may be processed into products using known techniques. Preferred products are meal, feedstock, and oil.

Feed, Meal, Protein, and Oil Preparations

Any of the plants or parts thereof of the present invention may be processed to produce a feed, meal, protein, or oil preparation. A particularly preferred plant part for this purpose is a seed. In a preferred embodiment the feed, meal, protein, or oil preparation is designed for ruminant animals. Methods to produce feed, meal, protein, and oil preparations are known in the art. See, for example, U.S. Pat. Nos. 4,957,748; 5,100,679; 5,219,596; 5,936,069; 6,005,076; 6,146,669; and 6,156,227. In a preferred embodiment, the protein preparation is a high protein preparation. Such a high protein preparation preferably has a protein content of greater than about 5% w/v, more preferably about 10% w/v, and even more preferably about 15% w/v. In a preferred oil preparation, the oil preparation is a high oil preparation with an oil content derived from a plant or part thereof of the present invention of greater than about 5% w/v, more preferably greater than about 10% w/v, and even more preferably greater than about 15% w/v. In a preferred embodiment the oil preparation is a liquid and of a volume greater than 1, 5, 10, or 50 liters. The present invention provides for oil produced from plants of the present invention or generated by a method of the present invention. Such oil may be a minor or major component of any resultant product. Moreover, such oil maybe blended with other oils. In a preferred embodiment, the oil produced from plants of the present invention or generated by a method of the present invention constitutes greater than about 0.5%, 1%, 5%, 10%, 25%, 50%, 75%, or about 90% by volume or weight of the oil component of any product. In another embodiment, the oil preparation may be blended and can constitute greater than about 10%, 25%, 35%, 50%, or about 75% of the blend by volume. Oil produced from a plant of the present invention can be admixed with one or more organic solvents or petroleum distillates.

In a further embodiment, meal of the present invention may be blended with other meals. In a preferred embodiment, the meal produced from plants of the present invention or generated by a method of the present invention constitutes greater than about 0.5%, 1%, 5%, 10%, 25%, 50%, 75%, or about 90% by volume or weight of the meal component of any product. In another embodiment, the meal preparation maybe blended and can constitute greater than about 10%, 25%, 35%, 50%, or about 75% of the blend by volume.

Seed Containers

Seeds of the plants may be placed in a container. As used herein, a container is any object capable of holding such seeds. A container preferably contains greater than about 500, 1,000, 5,000, or about 25,000 seeds where at least about 10%, 25%, 50%, 75%, or about 100% of the seeds are derived from a plant of the present invention.

Breeding Programs

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc.). Selected, non-limiting approaches, for breeding the plants of the present invention are set forth below. A breeding program can be enhanced using marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability, etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates for new commercial cultivars; those still deficient in traits may be used as parents to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated selfing and selection, producing many new genetic combinations.

The development of new cultivars requires the development and selection of varieties, the crossing of these varieties and the selection of superior hybrid crosses. The hybrid seed can be produced by manual crosses between selected male-fertile parents or by using male sterility systems. Hybrids are selected for certain single gene traits such as pod color, flower color, seed yield, pubescence color, or herbicide resistance, which indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Pedigree breeding is used commonly for the improvement of self-pollinating crops. Two parents who possess favorable, complementary traits are crossed to produce an $F_1$. An $F_2$ population is produced by selfing one or several $F_1$'s. Selection of the best individuals from the best families is carried out. Replicated testing of families can begin in the $F_4$ generation to improve the effectiveness of selection for traits with low heritability. At an advanced stage of inbreeding (i;e., $F_6$ and $F_7$), the best lines or mixtures of phenotypically similar lines are tested for potential release as new cultivars.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding.

Descriptions of other breeding methods that are commonly used for different traits and crops can be found in one of several reference books (e.g., Fehr, *Principles of Cultivar Development*, Vol. 1, pp. 2-3 (1987)).

A transgenic plant of the present invention may also be reproduced using apomixis. Apomixis is a genetically controlled method of reproduction in plants where the embryo is formed without union of an egg and a sperm. There are three basic types of apomictic reproduction: 1) apospory where the embryo develops from a chromosomally unreduced egg in an embryo sac derived from the nucleus, 2) diplospory where the embryo develops from an unreduced egg in an embryo sac derived from the megaspore mother cell, and 3) adventitious embryony where the embryo develops directly from a somatic cell. In most forms of apomixis, pseudogamy, or fertilization of the polar nuclei to produce endosperm is necessary for seed viability. In apospory, a nurse cultivar can be used as a pollen source for endosperm formation in seeds. The nurse cultivar does not affect the genetics of the aposporous apomictic cultivar since the unreduced egg of the cultivar develops parthenogenetically, but makes possible endosperm production. Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic plants are known in the art. See, U.S. Pat. No. 5,811,636.

Other Organisms

A nucleic acid of the present invention may be introduced into any cell or organism such as a mammalian cell, mammal, fish cell, fish, bird cell, bird, algae cell, algae, fungal cell, fungi, or bacterial cell. Preferred host and transformants include: fugal cells such as *Aspergillus*, yeasts, mammals, particularly bovine and porcine, insects, bacteria, and algae. Preferred bacteria are *E. coli* and *Agrobacterium tumefaciens*.

Methods to transform such cells or organisms are known in the art (EP 0 238 023; Yelton et al., 1984; Malardier et al., 1989; Becker and Guarente; Ito et al., 1983; Hinnen et al., 1978; and Bennett and LaSure, 1991). Methods to produce proteins from such organisms are also known (Kudla et al., 1990; Jarai and Buxton, 1994; Verdier, 1990; MacKenzie et al., 1993; Hartl et al., 1994; Bergeron et al., 1994; Demolder et al., 1994; Craig, 1993; Gething and Sambrook, 1992; Puig and Gilbert, 1994; Wang and Tsou, 1993; Robinson et al., 1994; Enderlin and Ogrydziak, 1994; Fuller et al., 1989; Julius et al., 1984; and Julius et al., 1983).

EXAMPLES

The following examples are provided and should not be interpreted in any way to limit the scope of the present invention.

Example 1

Generation of Clones of USP Promoters from *Vicia Faba*

USP promoters are obtained from *Vicia faba* genomic DNA via PCR amplification (Expand High Fidelity PRC System, Cat# 1 732 641, Roche Molecular Biochemicals, Indianapolis, Ind.) using primers designed according to the published sequence (GenBank Accession X56240). Primers used for amplification of the USP promoters are:

```
5'-AAACTGCAGCAAATTTACACATTG-3';    (SEQ ID NO:6)
and

5'-AAACCATGGTTGACTGGCTATG-3'.      (SEQ ID NO:7)
```

Figure 2:
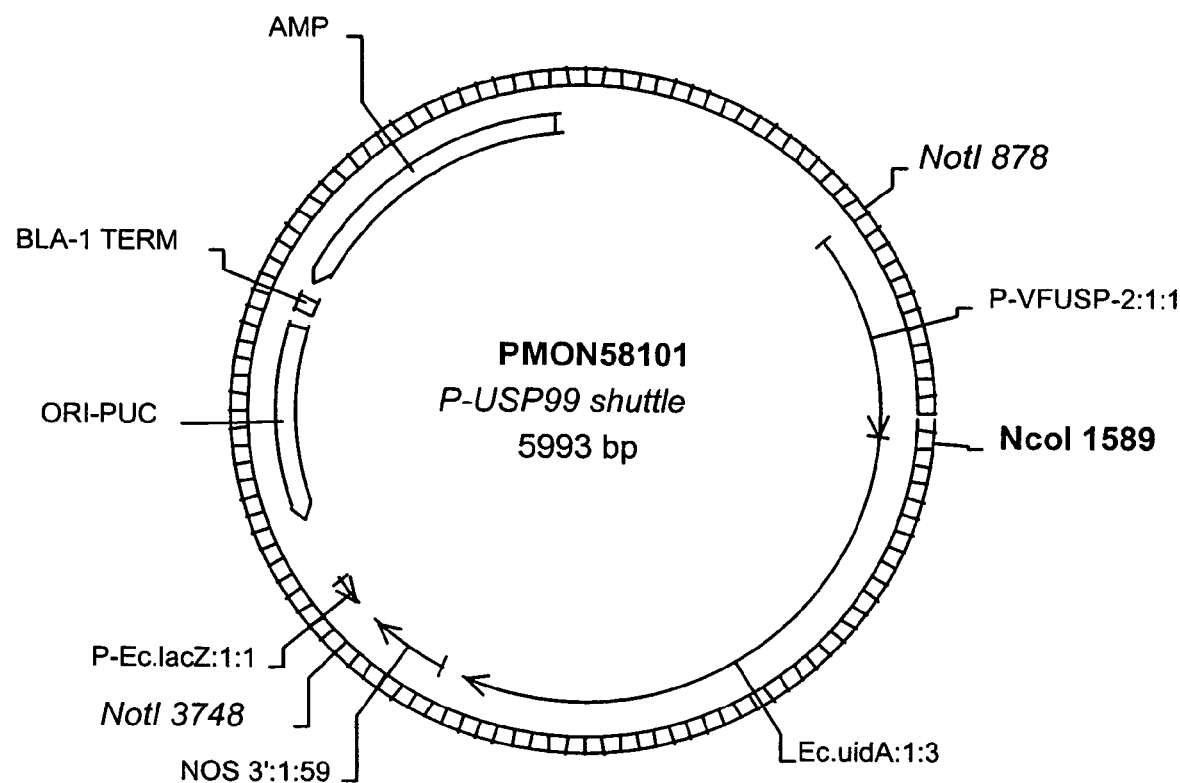
FIG. 2 is a schematic of vector pMON58101.
Figure 3:
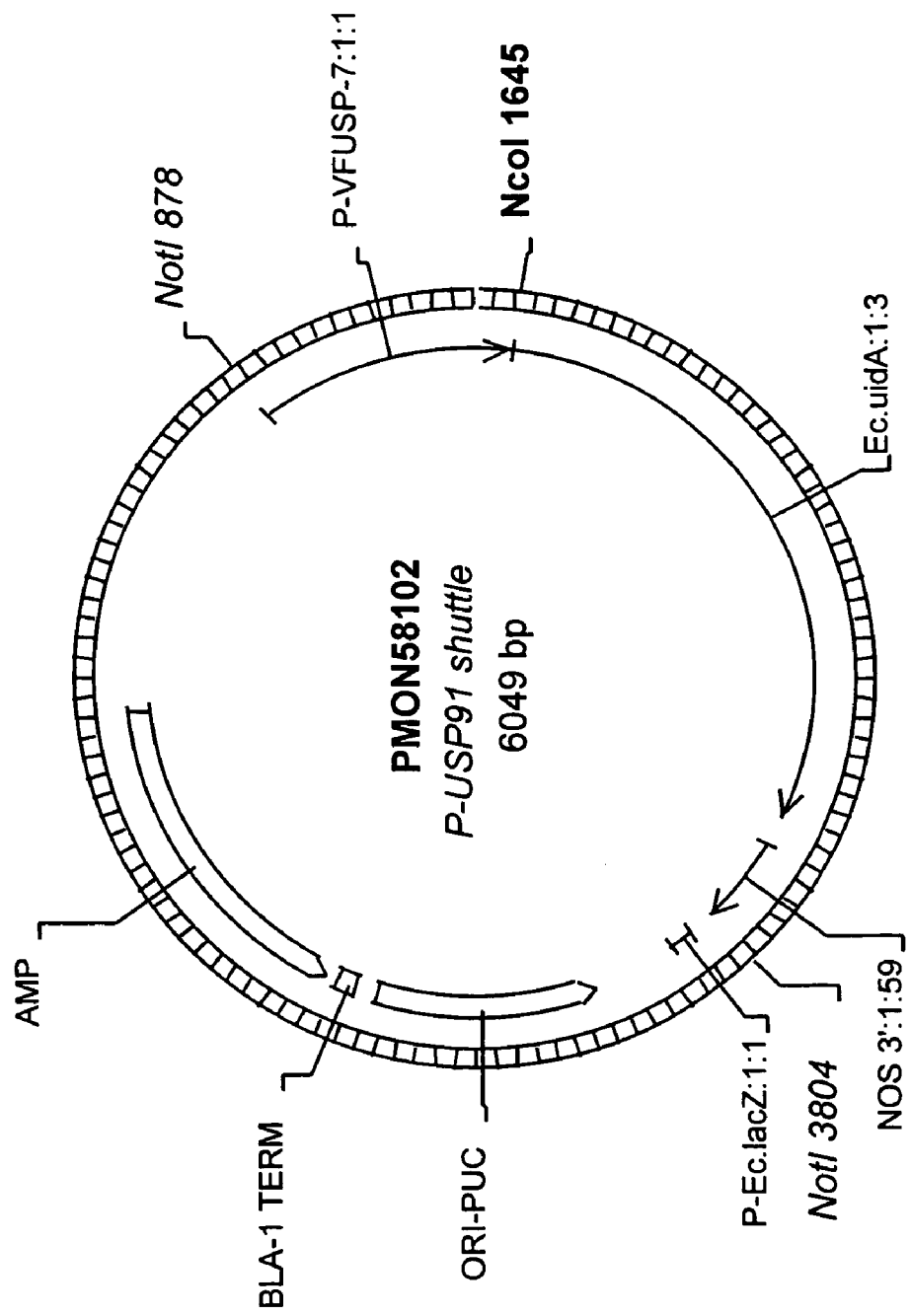
FIG. 3 is a schematic of vector pMON58102.
Figure 4:
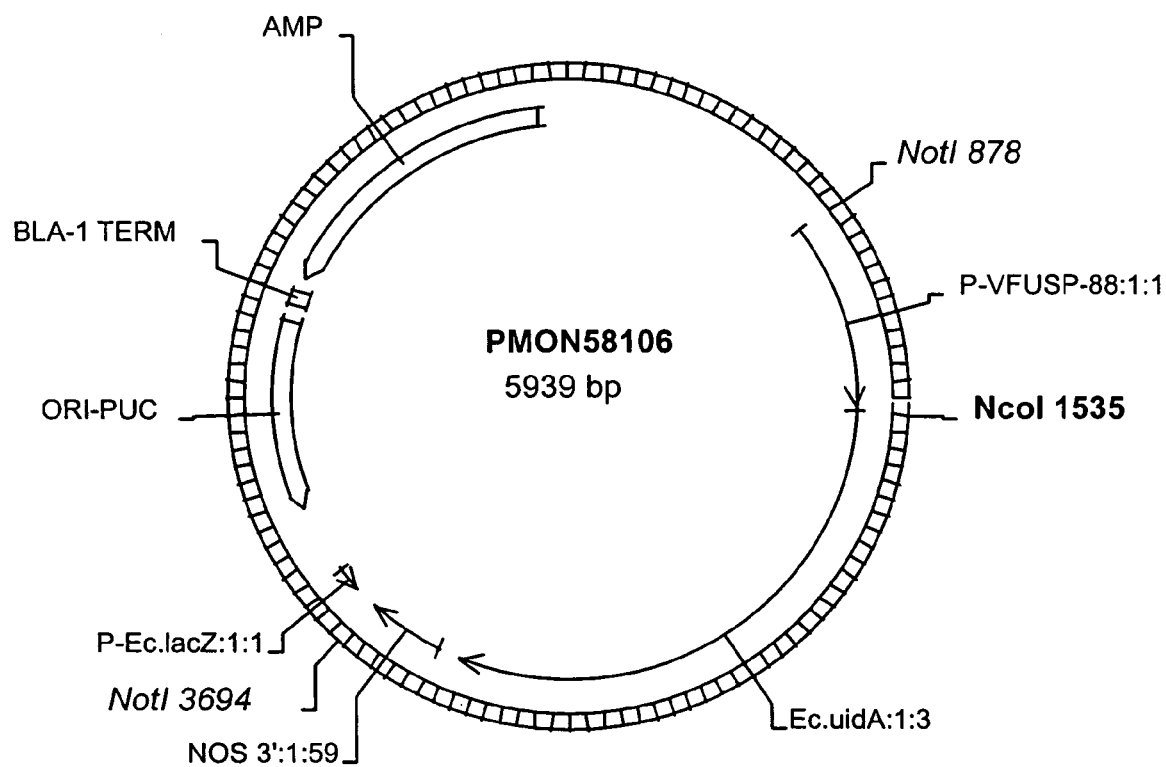
FIG. 4 is a schematic of vector pMON58106.

The isolated amplification products are then subcloned into the vector pMON13773 (FIG. 1) producing clones pMON58101 (USP99) (FIG. 2), pMON58102 (USP91) (FIG. 3), and pMON58106 (USP88) (FIG. 4).

Example 2

Generation of a Chimeric eUSP88 Promoter

A PCR reaction is performed using pMON58106 as a template (Expand High Fidelity PRC System, Catalog number 1 732 641, Roche Molecular Biochemicals, Indianapolis, Ind.). The following primers are used for amplification:

```
5'-AAACTGCAGCAAATTTACACATTG-3';    (SEQ ID NO:6)
and

5'-AAACTGCAGGACTACATGCATAAC-3'.    (SEQ ID NO:8)
```

Figure 5:
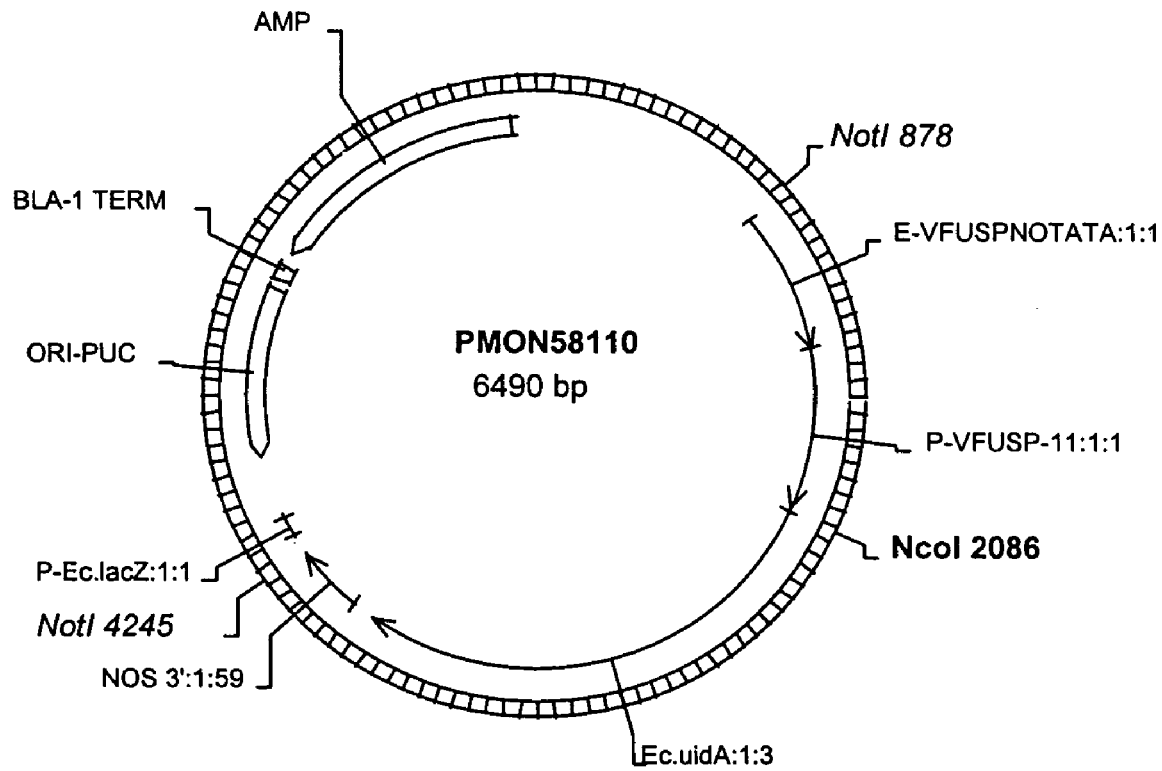
FIG. 5 is a schematic of vector pMON58110.
Figure 6:
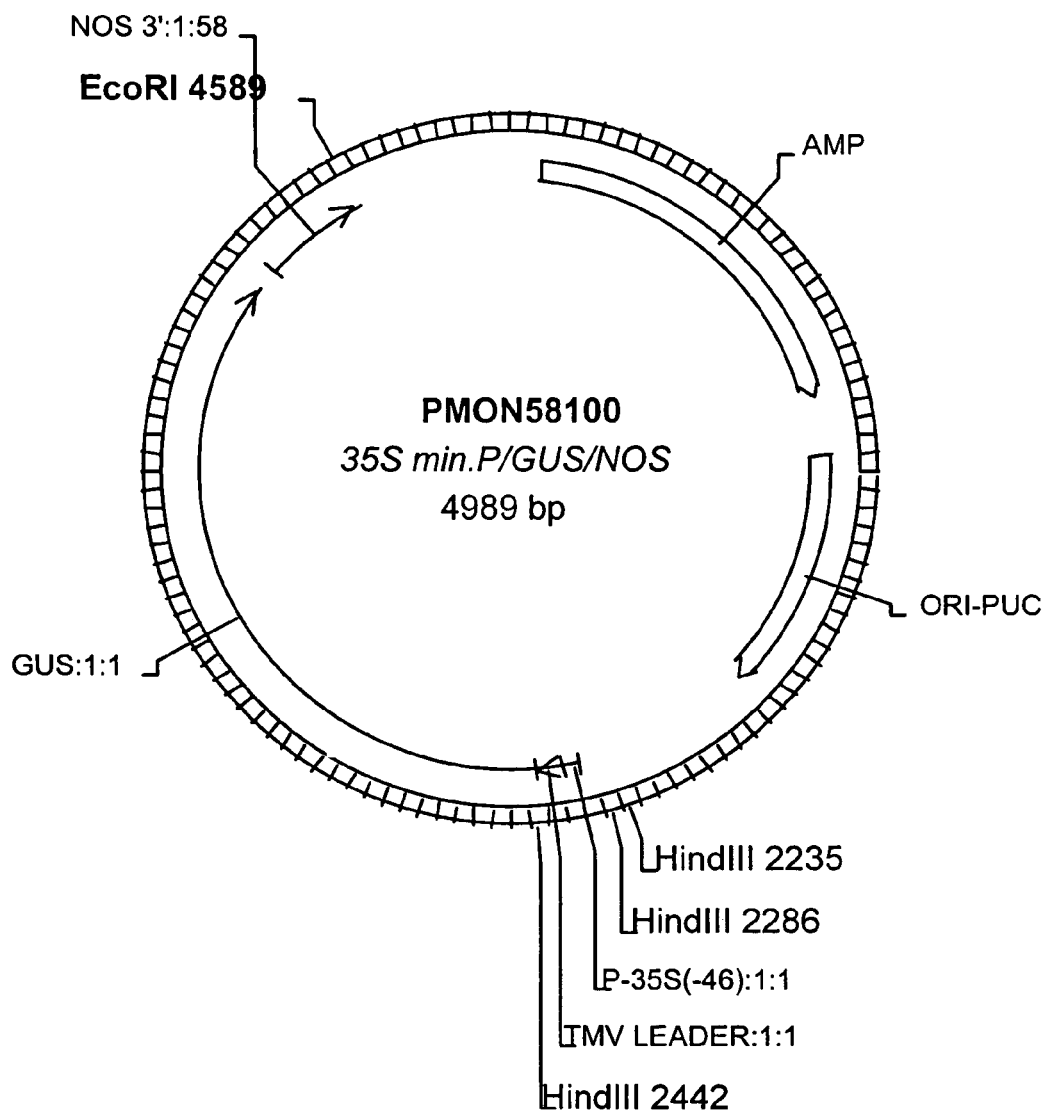
FIG. 6 is a schematic of vector pMON58100.
Figure 7:
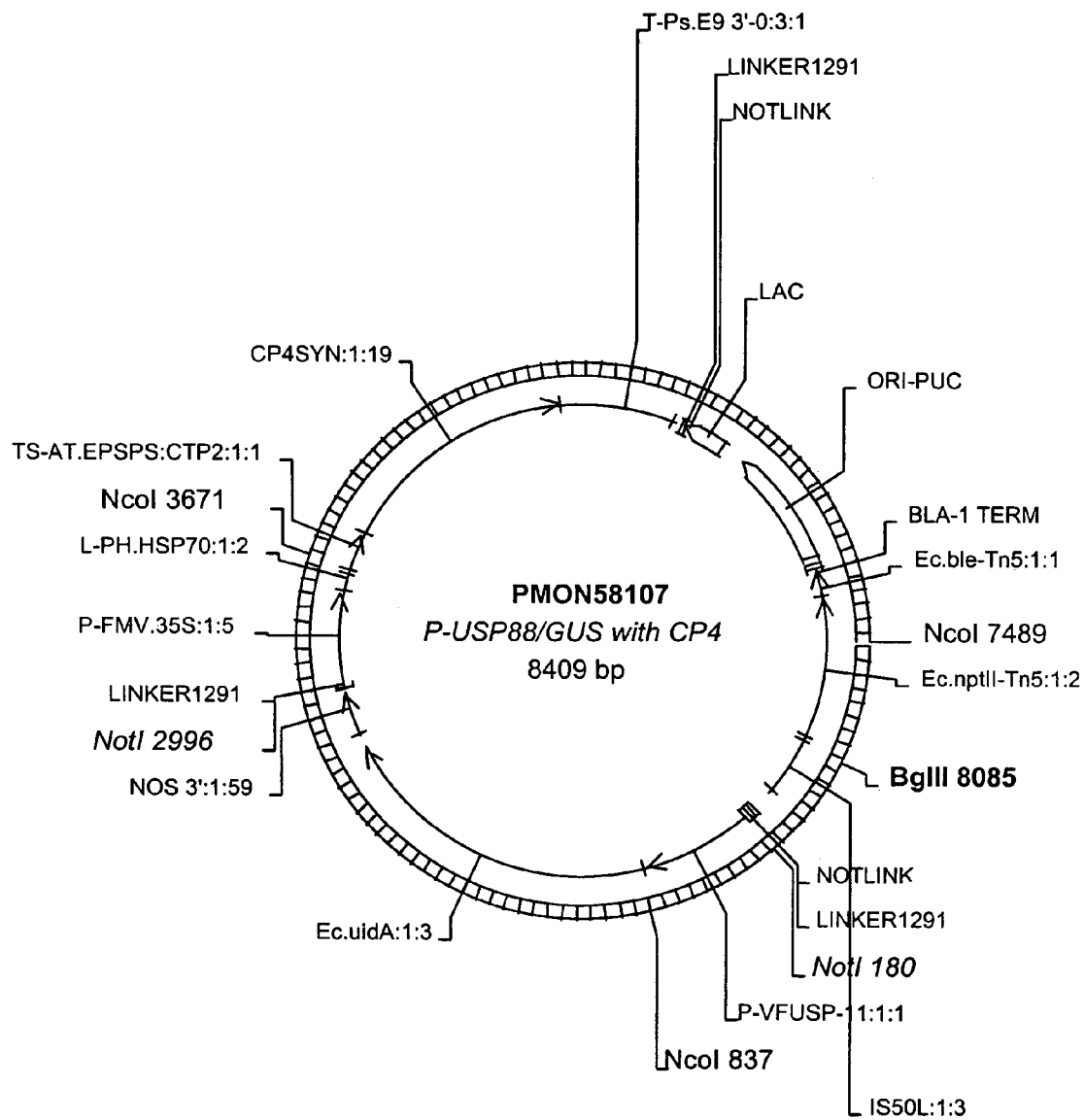
FIG. 7 is a schematic of vector pMON58107.

The amplified promoter fragments are digested using Pst I restriction enzyme and are ligated to pMON58106 DNA which are linearized by Pst I digestion and treated with CIP alkaline phosphatase. A plasmid with the desired orientation is selected and designated as pMON58110 (eUSP88) (FIG. 5).

Example 3

Evaluation of USP Promoters Using Soybean Cotyledon Transient Transformation

Seeds from soybean plants (Asgrow A3244) are harvested 25-28 days after flowering and osmotically treated overnight at 25° C. in dark on GAMBORG's medium (G5893, Sigma Company, St. Louis, Mo.) supplemented with of 50 mM glutamine, 111 mM maltose, 125 mM raffinose, 125 mM mannitol and 3 g/l purified agar, pH 5.6. The resulting 125 cotyledons are cut in half and bombarded with purified supercoiled DNA of pMON13773 (7Sα'), pMON58101 (USP99), pMON58102 (USP91), pMON58106 (USP88), and pMON58110. (Minimum 35S) using particle gun technology (Maliga et al., 1995, "Methods in Plant Molecular Biology, A Laboratory Course Manual," Cold Spring Harbor Laboratory Press, page 47). A separate e35S driven luciferase construct is included in a 1:1 molar ratio with each of the promoter constructs as a low expression control. Bombarded tissues are incubated for 48 hours at 25° C.

Figure 14:
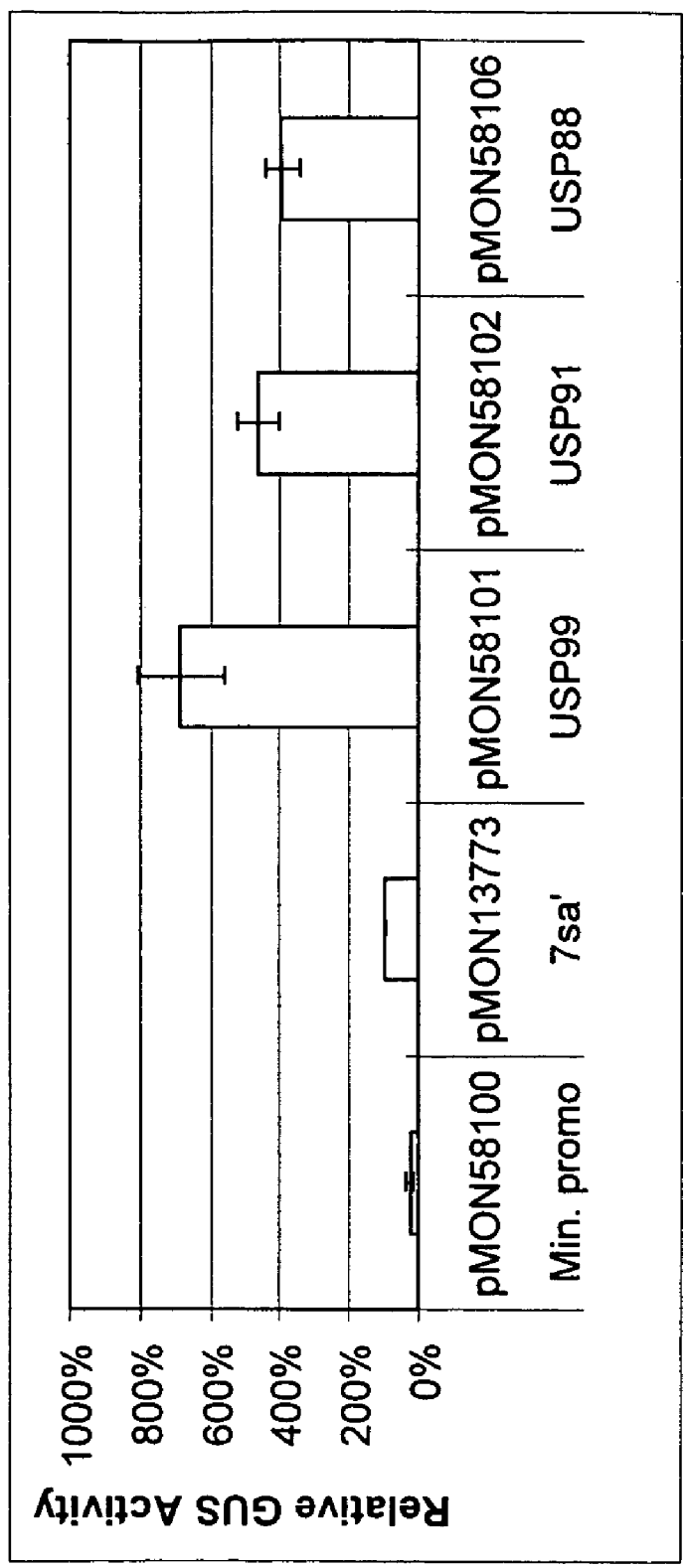
FIG. 14 is a graph representing the relative GUS activity of various constructs.
Figure 15:
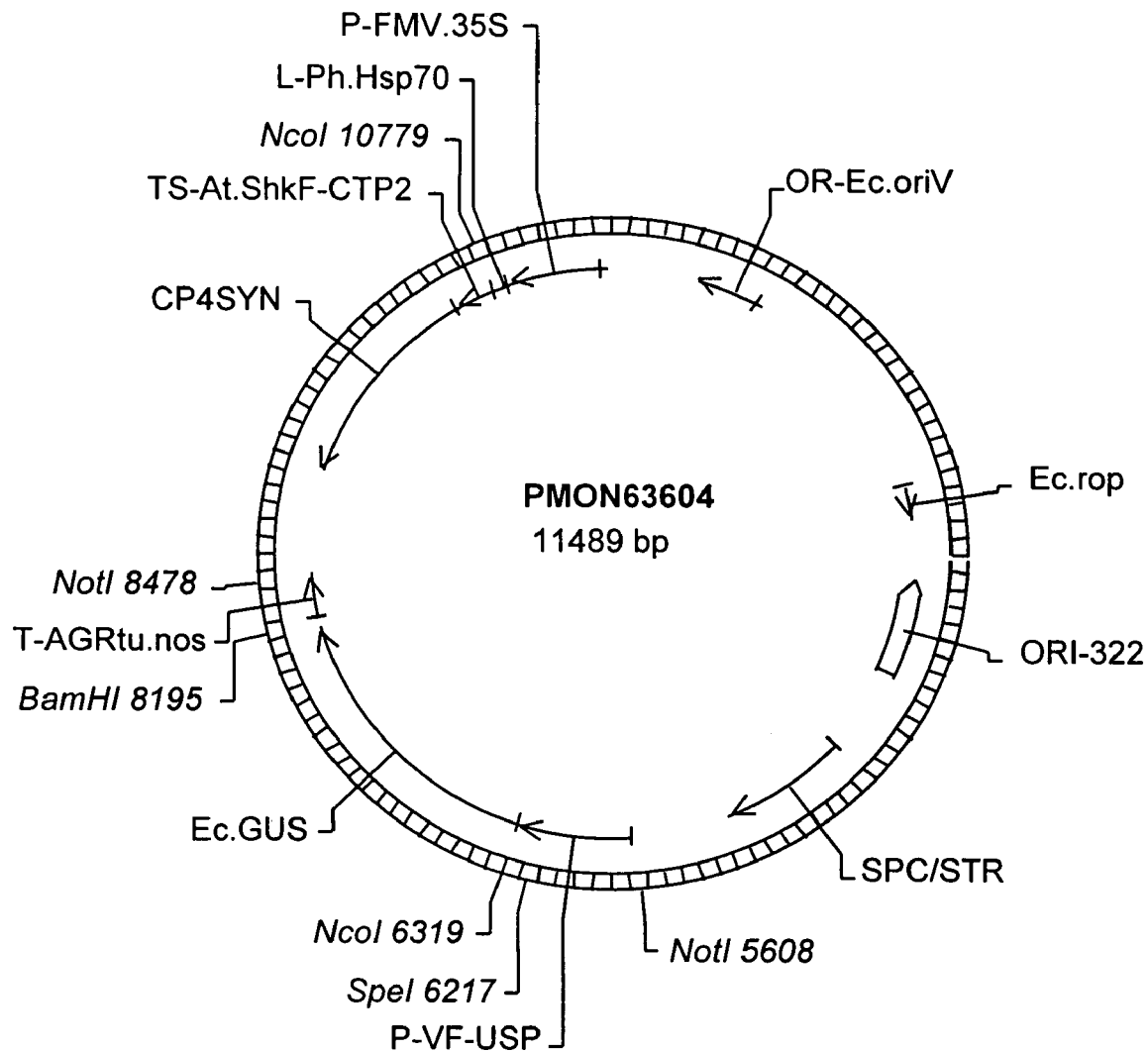
FIG. 15 is a schematic of vector pMON63604.
Figure 16:
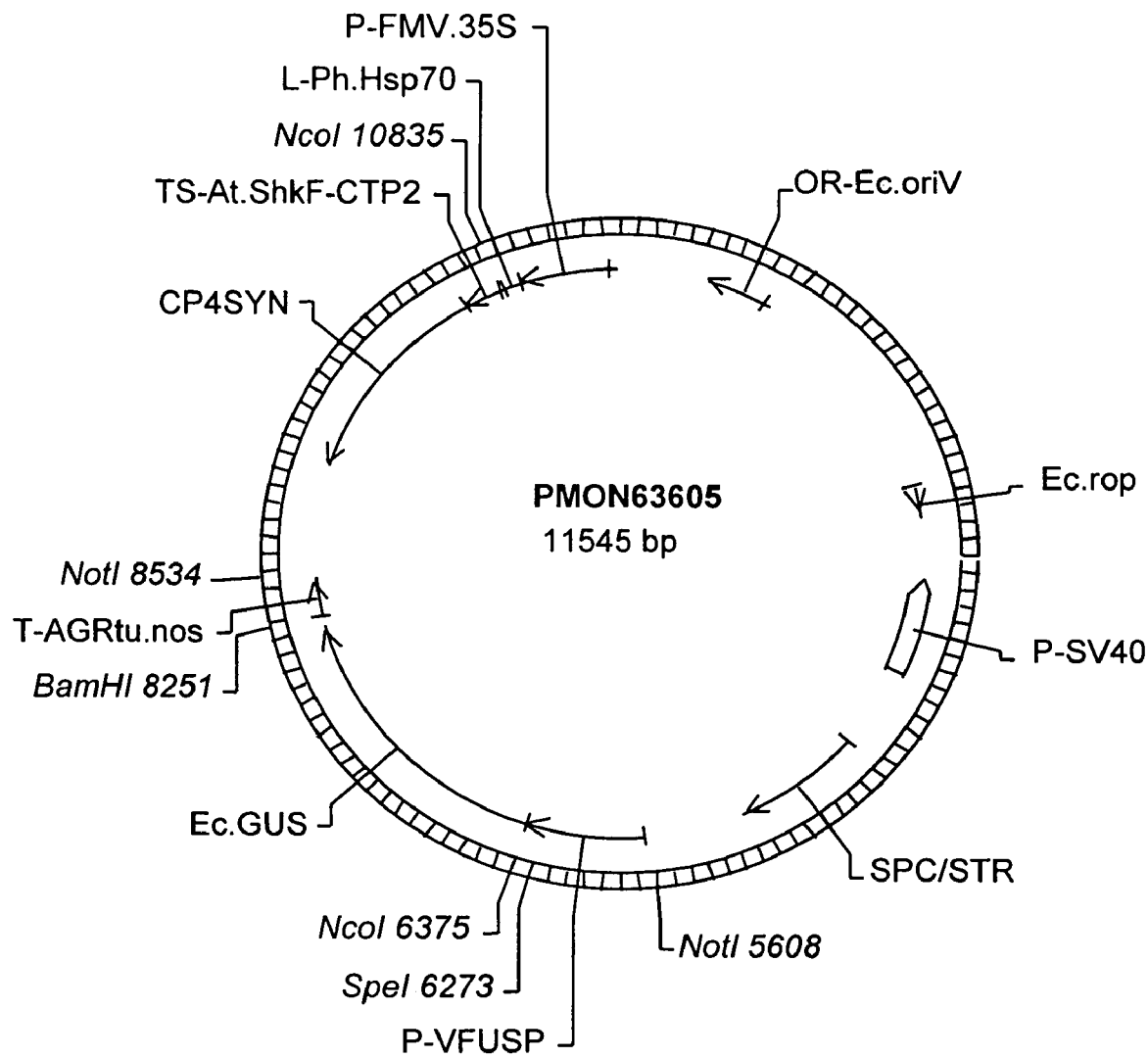
FIG. 16 is a schematic of vector pMON63605.
Figure 17:
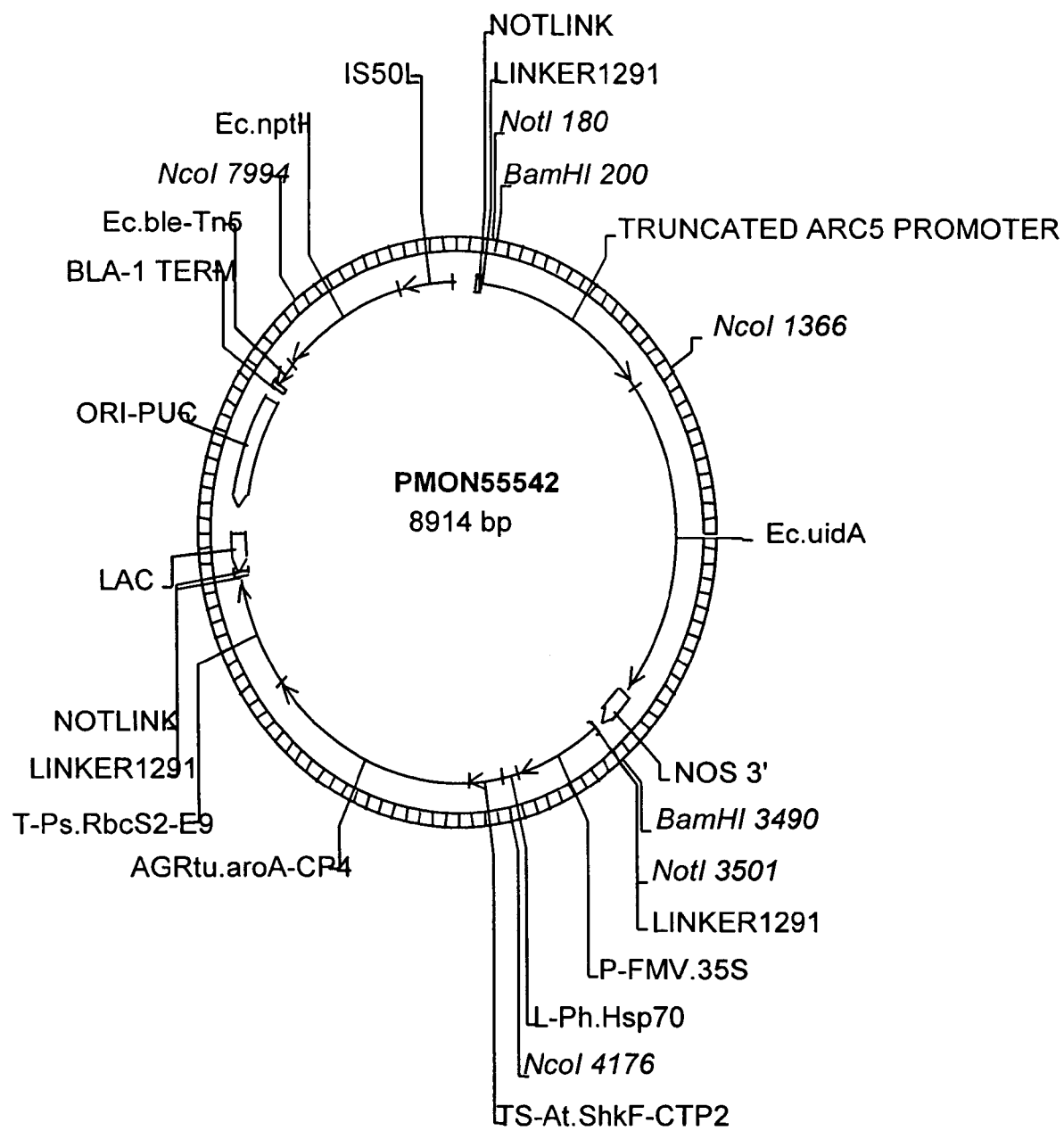
FIG. 17 is a schematic of vector pMON55542.

Proteins are extracted from six bombarded soybean cotyledons using 1 ml extraction buffer containing 0.1 M potassium phosphate (pH 7.8), 10 mM DTT, 1 mM EDTA, 5% glycerol, and proteinase inhibitor (1 tablet/50 ml, Roche Molecular Biochemicals, Catalog number 1 697 498, Indianapolis, Ind.). A 100 μl aliquot of the protein extract is used for Luciferase assay following a "Steady-Glo" procedure by Promega (Catalog number E2510, Promega Corporation, Madison, Wis.). A 50 μl aliquot of the protein extract is used for a standard GUS assay protocol with minor modifications (Maliga et al., 1995, "Methods in Plant Molecular Biology, A Laboratory Course Manual", Cold Spring Harbor Laboratory Press, page 29). Each sample is assayed twice and the average value is used for data analysis. GUS activity is normalized using luciferase activity and the relative promoter strength is expressed by setting the benchmark promoter 7Sα' (pMON13773) (FIG. 1) arbitrarily at 100%. The experiment is repeated independently three times. The results (FIG. 14) indicate that the USP promoters significantly increase expression of GUS when compared to the 7Sα' promoter, a benchmark promoter traditionally used for high level expression in soybean seeds. The minimal promoter/GUS construct (pMON58100), which is a low expression control using a 35 minimum promoter driving GUS) is expressed at a level of approximately 20% of that of a 7Sα' construct (pMON13773) (FIG. 1).

Example 4

Production of Transgenic Soybean Plants Containing USP Promoters

To test the strength of USP promoters in transgenic soybean, pMON55526 (Arc5/GUS/NOS), pMON55542 (T-Arc5/GUS/NOS), pMON63605 (USP91/GUS/NOS), pMON58107 (USP88/GUS/NOS), pMON63604 (USP99/GUS/NOS), and pMON58113 (eUSP88/GUS/NOS) are constructed by following standard molecular cloning protocols with minor modification (Sambrook et al., Molecular Cloning: A laboratory manual, 1989, Cold Spring Harbor Laboratory Press; Maliga et al., Methods in Plant Molecular Biology: A laboratory course manual, 1995, Cold Spring Harbor Laboratory Press). An expression cassette consisting of an FMV promoter, transit peptide sequence, CP4 coding gene and E9 3' UTR is included as selectable marker in all transformation vectors.

For the particle bombardment transformation method, soybean seeds (Asgrow A3244, A4922) are germinated overnight (18-24 hours) and the meristem explants are excised. The primary leaves are removed to expose the meristems. Prepared explants are stored for up to two days at 4° C. in the dark in OR media (see, U.S. Pat. No. 5,914,451 for description of OR media) and at 15° C. in the dark for one day. Immediately prior to bombardment, the prepared explants are placed in targeting media (see, U.S. Pat. No. 5,914,451 for description of targeting media) with the meristems positioned perpendicular to the direction of the particle delivery. DNA containing, pMON55526, pMON58107, or pMON55542 is precipitated onto microscopic gold particles with $CaCl_2$ and spermidine and subsequently resuspended in ethanol. The suspension is coated onto a mylar sheet which is then placed onto the electric discharge device. The particles are accelerated into the plant tissue by electric discharge at approximately 60% capacitance. Typically, targets are bombarded once. Following bombardment, explants are placed in selection media (WPM+75 µM glyphosate, see, U.S. Pat. No. 5,914,451 for description) for 5-7 weeks to allow selection and growth of transgenic shoots. Phenotype positive shoots are harvested approximately 5-7 weeks post bombardment and placed into selective rooting media (BRM +25 microM glyphosate, see, U.S. Pat. No. 5,914,451 for description) for 2-3 weeks. Shoots producing roots are transferred to a greenhouse and potted in soil. Shoots that remain healthy on selection, but do not produce roots, are transferred to non-selective rooting media (BRM, as above) for an additional two weeks. Roots from any shoots that produce roots off selection are tested for expression of the plant selectable marker before they are transferred to the green house and potted in soil. Plants are maintained under standard green house conditions until RI seed harvest.

Figure 8:
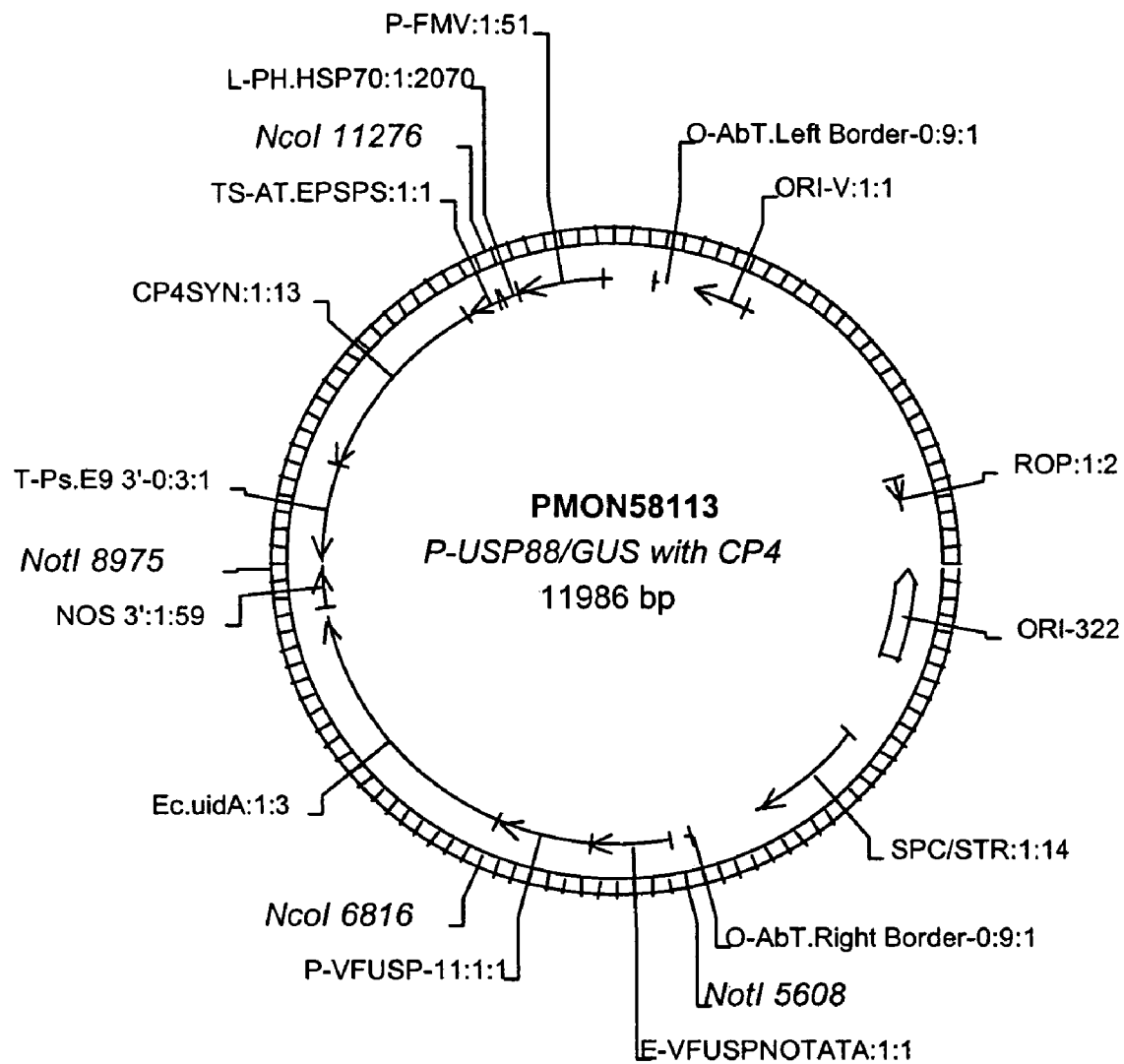
FIG. 8 is a schematic of vector pMON58113.
Figure 9:
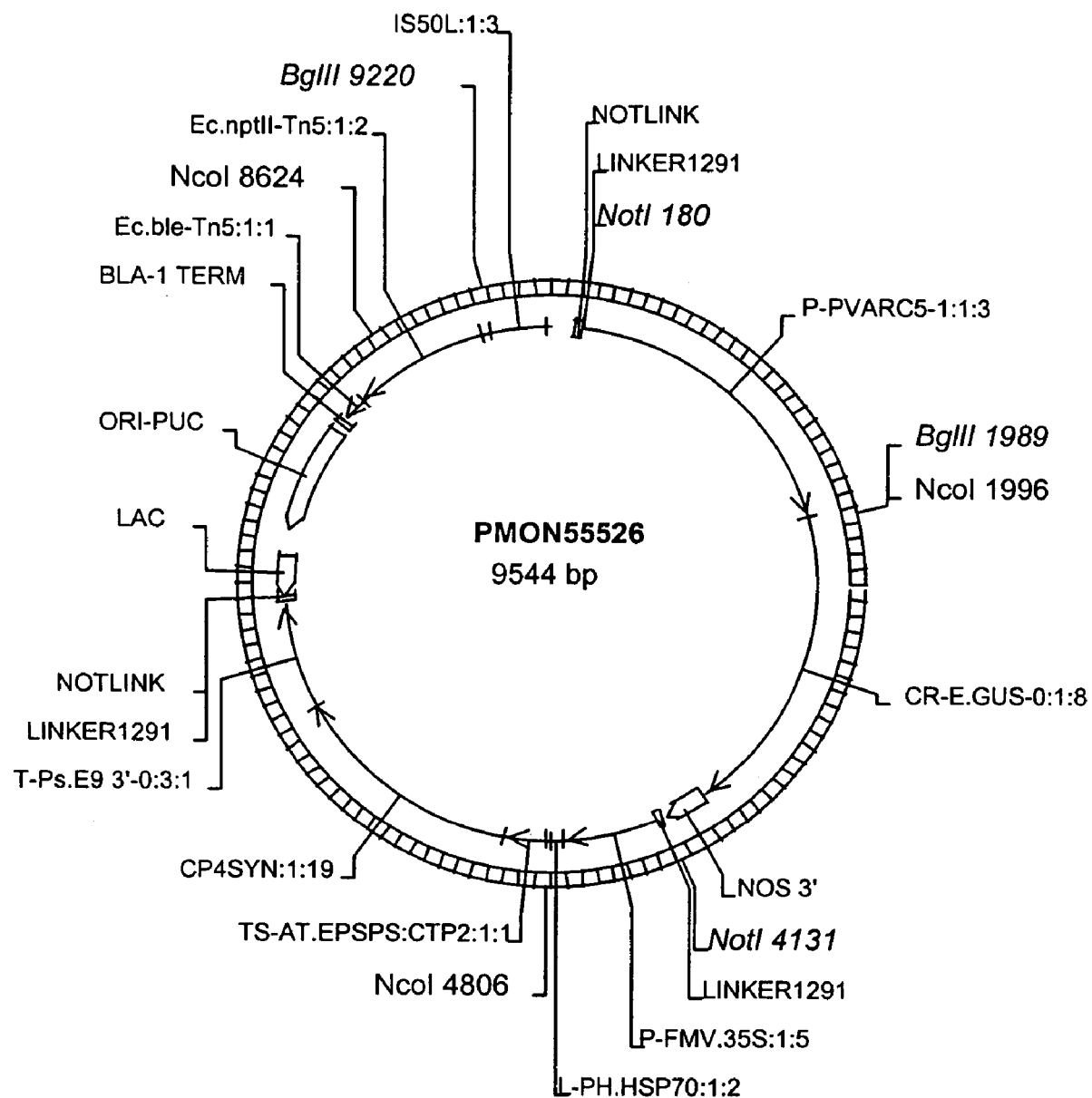
FIG. 9 is a schematic of vector pMON55526.
Figure 10:
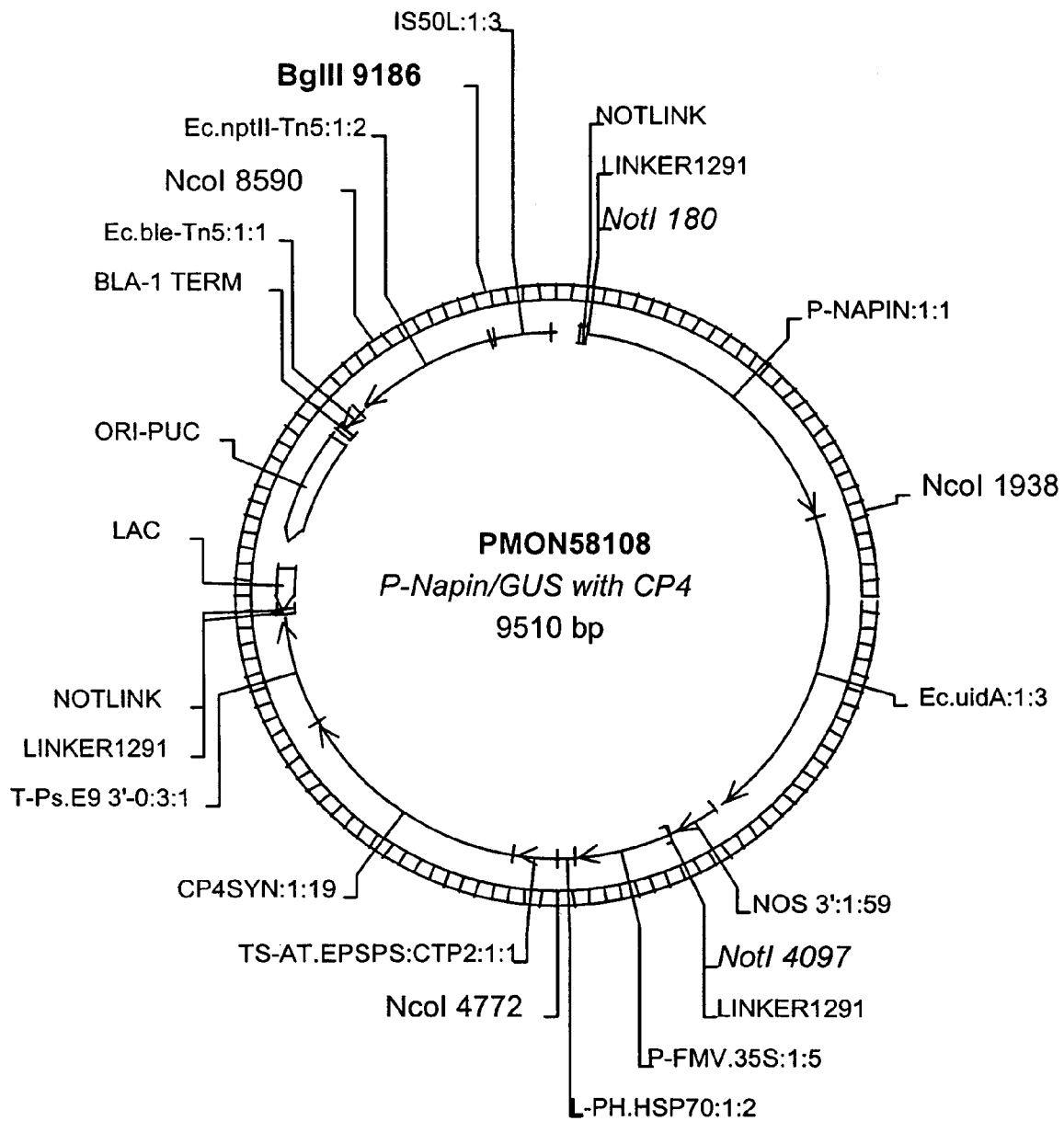
FIG. 10 is a schematic of vector pMON58108.
Figure 11:
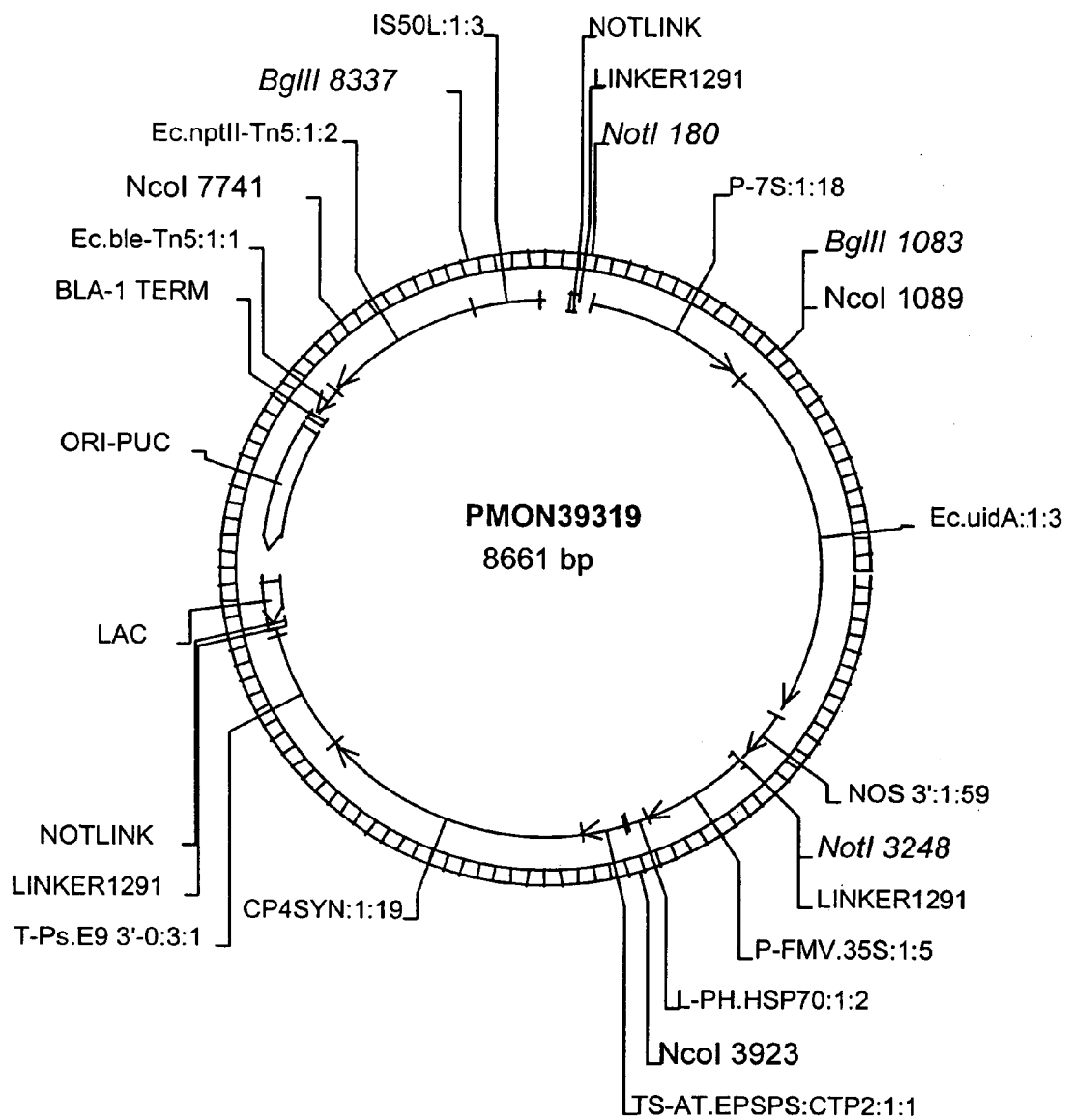
FIG. 11 is a schematic of vector pMON39319.

For the *Agrobacterium* transformation method, commercially available soybean seeds (Asgrow A3244, A4922) are germinated overnight (approximately 10-12 hours) and the meristem explants are excised. The primary leaves may or may not be removed to expose the meristems and the explants are placed in a wounding vessel. *Agrobacterium* strain ABI containing pMON58113 (FIG. 8), pMON63605, or pMON63604 is grown to log phase. Cells are harvested by centrifugation and resuspended in inoculation media containing inducers. Soybean explants and the induced *Agrobacterium* culture are mixed no later than 14 hours from the time of initiation of seed germination and wounded using sonication.

Following wounding, explants are incubated in *Agrobacterium* for a period of approximately one hour. Following this inoculation step, the *Agrobacterium* is removed by pipetting and the explants are placed in co-culture for 2-4 days. They are transferred to selection media (WPM+0.075 mM glyphosate +antibiotics to control *Agrobacterium* overgrowth) for 5-7 weeks to allow selection and growth of transgenic shoots. Phenotype positive shoots are harvested approximately 5-7 weeks post-bombardment and placed into selective rooting media (BRM+0.025 mM glyphosate) for 2-3 weeks. Shoots producing roots are transferred to the greenhouse and potted in soil. Shoots that remained healthy on selection, but did not produce roots were transferred to non-selective rooting media (BRM without glyphosate) for an additional 2 weeks. The roots from any shoots that produced roots off the selection are tested for expression of the plant selectable marker glyphosate resistance before transferring to the greenhouse and potting in soil. Plants are maintained under standard greenhouse conditions until R1 seed harvest.

Mature seeds from the selected plants are analyzed for GUS activity. To assay for GUS activity, eight seeds from each transgenic event (line) are ground individually. About 20 mg ground seed tissue is extracted using 200 µl extraction buffer containing 0.1 M potassium phosphate (pH 7.8), 10 mM DTT, 1 mM EDTA, 5% glycerol, and proteinase inhibitor (1 tablet/50 ml, Catalog number 1 697 498, Roche Molecular Biochemicals, Indianapolis, Ind.). The protein content of the extract is determined using Bio-Rad Protein Assay (Catalog number 61234A, Bio-Rad Laboratories, Hercules, Calif.) and the GUS activity is measured using a standard GUS assay protocol with minor modifications (Maliga et al., 1995, "Methods in Plant Molecular Biology, A Laboratory Course Manual", Cold Spring Harbor Laboratory Press, p. 29). The GUS activity is normalized against the protein concentration. Each sample is assayed twice and the average value is used for data analysis.

Figure 12:
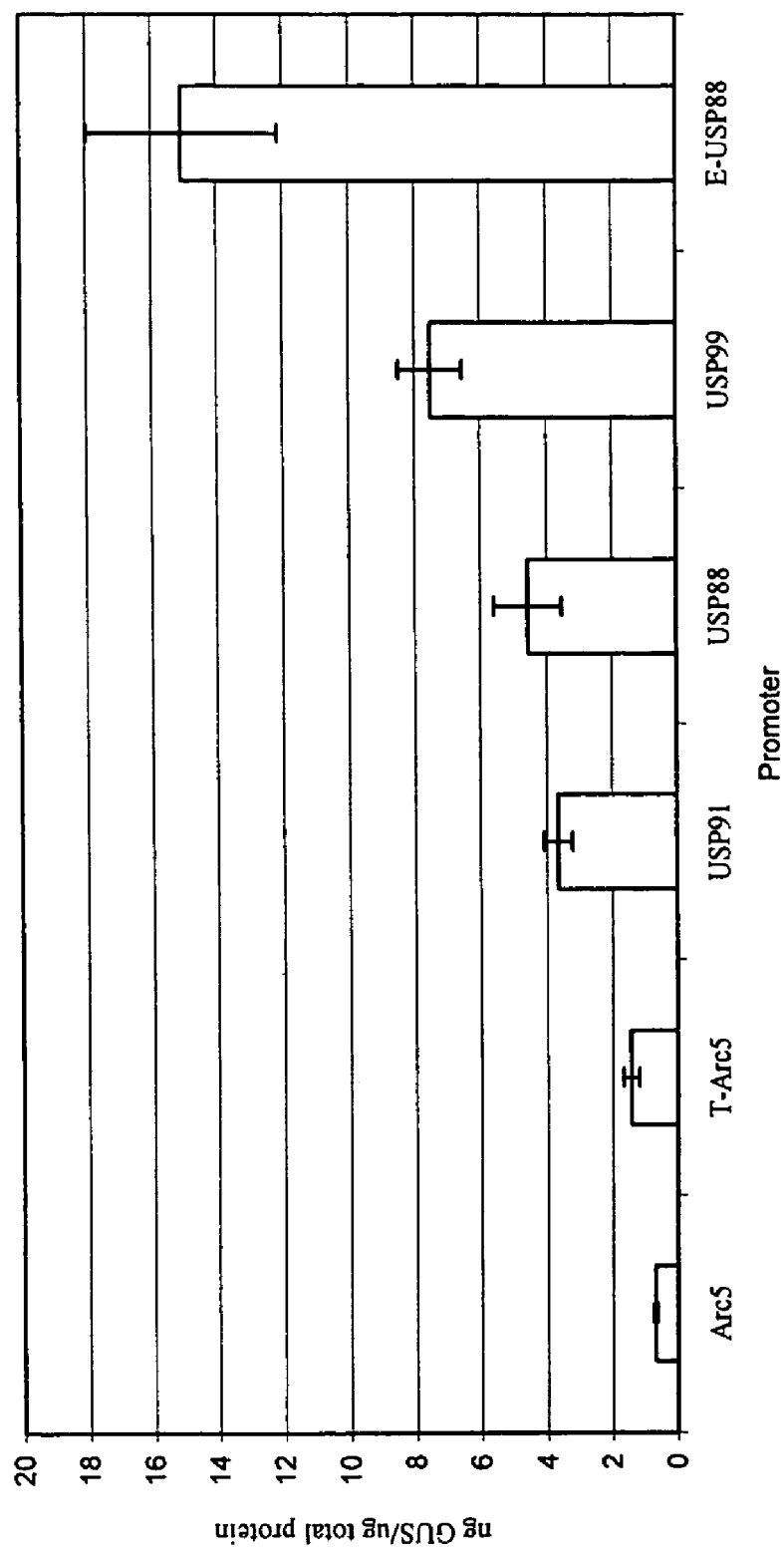
FIG. 12 is a graph representing the relative GUS activity expressed in transgenic soybean under the control of multiple promoters.

An event (line) is rejected if none of the 8 seeds had detectable GUS activity. If at least one seed of a particular event has detectable GUS, the event is considered a positive transgenic event. The seed sample with highest GUS activity within the event is chosen as the representative of the event because it is more likely to reflect GUS activity in homozygous seeds. Between 10-20 positive events are typically identified for each of the constructs. The average of the positive events are compared to demonstrate the relative strength of the promoter as shown in FIG. 12. The data show that the USP88 is about 3 times stronger than the T-Arc5 promoter, and about 6 times stronger than the Arc5 promoter in transgenic soybean seeds (FIG. 12). The result also shows that the eUSP88 promoter is about 10 times stronger than the T-Arc5 promoter in transgenic soybean seeds (FIG. 12).

Example 5

Figure 13:
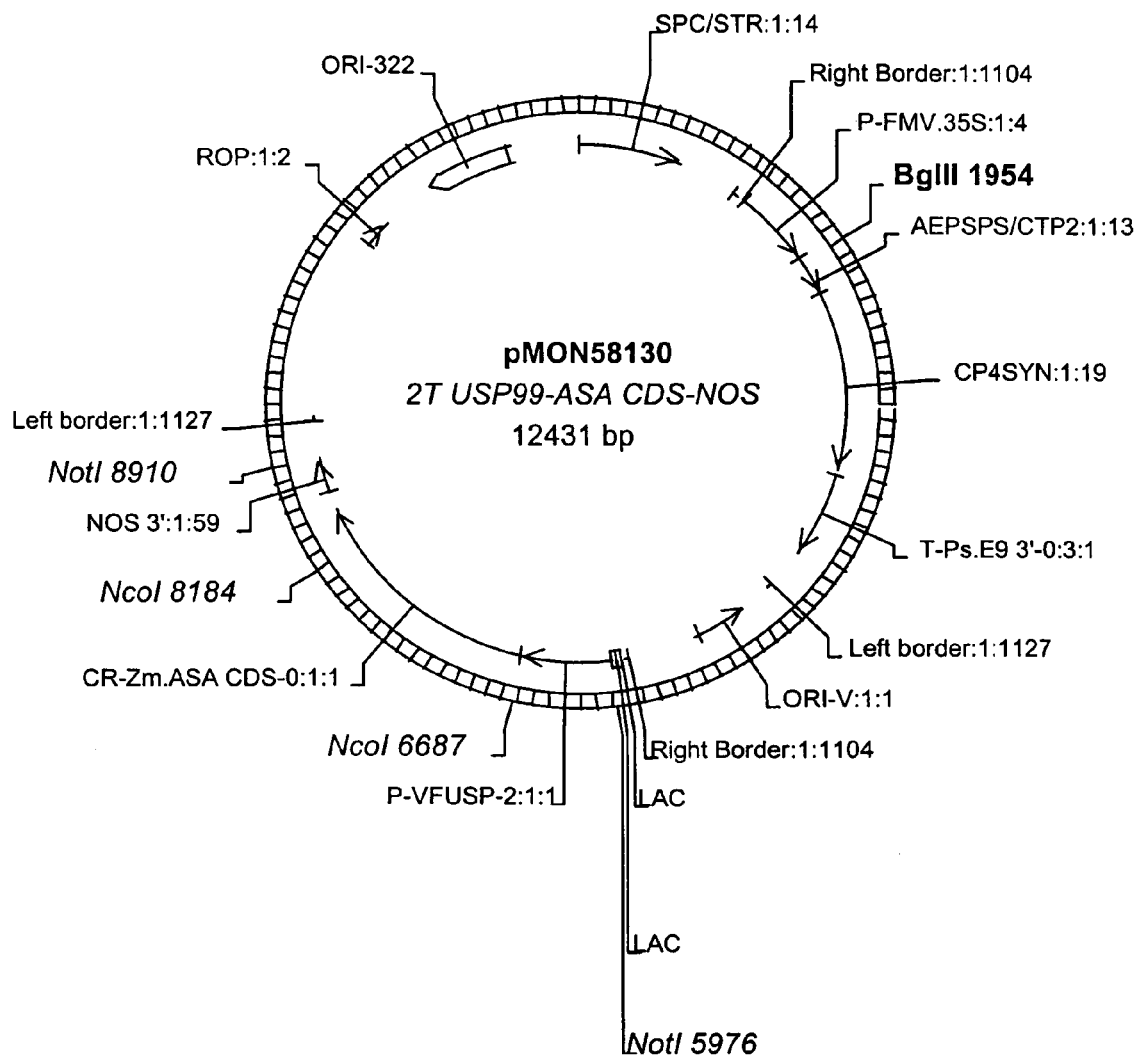
FIG. 13 is a schematic of vector pMON58130.

Production of Transgenic Soybean Plants Containing Elevated Level of Free Tryptophan in Seeds An *Agrobacterium* transformation vector pMON58130 (FIG. 13) is created to demonstrate the effectiveness of the USP99 promoter at driving a tryptophan-insensitive α-subunit of anthranilate synthase from C28 maize (U.S. Pat. No. 6,118,047) in transgenic soybean. Construction of vector pMON58130 (FIG. 13) is done by following standard molecular cloning protocols with minor modification (Sambrook et al., Molecular Cloning: A laboratory manual, 1989, Cold Spring Harbor Laboratory Press; Maliga et al., Methods in Plant Molecular Biology: A laboratory course manual, 1995, Cold Spring Harbor Laboratory Press). An expression cassette consisting of an FMV promoter, a transit peptide sequence, a CP4 coding gene, and an E9 3' UTR is included as a selectable marker in the transformation vector.

Figure 21:
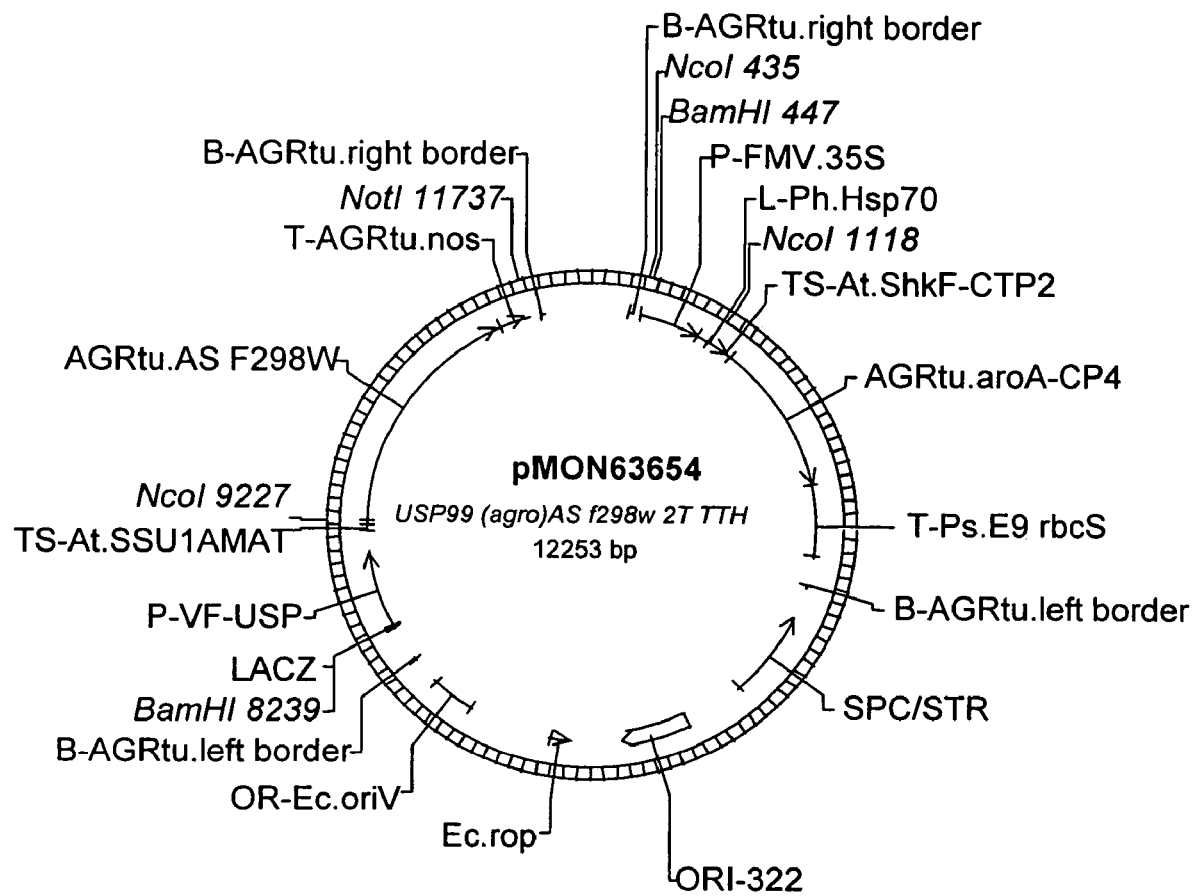
FIG. 21 is a schematic of vector pMON63654.

An additional Agrobacterium vector pMON63654 is created to demonstrate the effectiveness of the USP99 promoter at driving a tryptophan feedback insensitive mutant (F298W) of anthranilate synthase from Agrobacterium tumefaciens (U.S. Patent Application 60/288,904) in transgenic soybean. Construction of vector pMON63654 (FIG. 21) is done by following standard molecular cloning protocols with minor modification (Sambrook et al., Molecular Cloning: A laboratory manual, 1989, Cold Spring Harbor Laboratory Press; Maliga et al., Methods in Plant Molecular Biology: A laboratory course manual, 1995, Cold Spring Harbor Laboratory Press). An expression cassette consisting of the FMV promoter with the HSP70 5' UTR, CTP2 and CP4 coding gene and E9 3' UTR is included as selectable marker in this vector. In pMON63654 (FIG. 21), the USP99 promoter is ligated upstream of a gene consisting of a chloroplast transit peptide sequence CTP1 and an Agrobacterium anthranilate synthase (F298W) mutant. A NOS 3' UTR is used to signal transcription termination and polyadenylation.

For the Agrobacterium transformation method, commercially available soybean seeds (Asgrow A3244, A4922) are germinated overnight (approximately 10-12 hours) and the meristem explants are excised. The primary leaves may or may not be removed to expose the meristems and the explants are placed in a wounding vessel. Agrobacterium strain ABI containing pMON58130 or pMON63654 is grown to log phase. Cells are harvested by centrifugation and resuspended in inoculation media containing inducers. Soybean explants and the induced Agrobacterium culture are mixed no later than 14 hours from the time of initiation of seed germination and wounded using sonication.

Following wounding, explants are incubated in Agrobacterium for a period of approximately one hour. Following this inoculation step, the Agrobacterium is removed by pipetting and the explants are placed in co-culture for 2-4 days. At this point, they are transferred to selection media (WPM+0.075 mM glyphosate+antibiotics to control Agrobacterium overgrowth) for 5-7 weeks to allow selection and growth of transgenic shoots. Phenotype positive shoots are harvested approximately 5-7 weeks post-bombardment and placed into selective rooting media (BRM+0.025 mM glyphosate) for 2-3 weeks. Shoots producing roots are transferred to the greenhouse and potted in soil. Shoots that remained healthy on selection, but did not produce roots are transferred to non-selective rooting media (BRM without glyphosate) for an additional 2 weeks. The roots from any shoots that produced roots off the selection are tested for expression of the plant selectable marker glyphosate resistance before transferring to the greenhouse and potting in soil. Plants are maintained under standard greenhouse conditions until R1 seed harvest.

To assay for free tryptophan, ten mature R1 seeds from each transgenic event (line) are crushed individually. About 50 mg of crushed material from individual seed is placed in each centrifuge vial and weighed. One milliliter of 5% trichloroacetic acid is added to each sample. The samples are vortexed, and mixed at room temperature for 15 min. They are then microcentrifuged for 15 min at 14,000 rpm. Some of the supernatant is then removed, placed in a HPLC vial, and sealed. Extracted samples are analyzed for free amino acid using Zorbax Eclipse-AAA Columns and the Agilent 1100 HPLC (Agilent Technical Publication, "Amino Acid Analysis Using Zorbax Eclipse-AAA Columns and the Agilent 1100 HPLC." Mar. 17, 2000). Because the R1 seeds of each event most likely consist of a population of segregating seeds, the seed with the highest tryptophan reading among the 10 seeds of each event is chosen as the representative of the group for its high probability of being homozygous. The data is summarized in Tables 3 and 4 below.

Ten randomly selected non-transgenic Asgrow A3244 seeds are also analyzed and the one with the highest tryptophan level is included in the table as a negative control. pMON58130-1 through pMON58130-23 represent different events generated using vector pMON58130. Compared with non-transgenic A3244, most of the transgenic events have high level Trp accumulation. Elevated Trp accumulation is detected in multiple transgenic events using pMON58130 and pMON63654.

TABLE 3

Tryptophan Concentration in pMON58130 Events

| Event number | Trp (ppm) |
| --- | --- |
| A3244 | 306 |
| pMON58130-1 | 484 |
| pMON58130-2 | 3104 |
| pMON58130-3 | 8237 |
| pMON58130-4 | 7734 |
| pMON58130-5 | 432 |
| pMON58130-6 | 4540 |
| pMON58130-7 | 4698 |
| pMON58130-8 | 361 |
| pMON58130-9 | 344 |
| pMON58130-10 | 6435 |
| pMON58130-11 | 5310 |
| pMON58130-12 | 283 |
| pMON58130-13 | 200 |
| pMON58130-14 | 90 |
| pMON58130-15 | 5479 |
| pMON58130-16 | 6316 |
| pMON58130-17 | 1516 |
| pMON58130-18 | 3714 |
| pMON58130-19 | 4480 |
| pMON58130-20 | 636 |
| pMON58130-21 | 534 |
| pMON58130-22 | 872 |
| pMON58130-23 | 4986 |

TABLE 4

Tryptophan Concentration in pMON63654 Events

| pMON number | Description | Event number | Average of TRP (ppm) | Max of TRP (ppm) |
| --- | --- | --- | --- | --- |
| 63654 | USP99-F298W-AS | 27581 | 10,591 | 19,630 |
| 63654 | USP99-F298W-AS | 27654 | 1,802 | 17,796 |
| 63654 | USP99-F298W-AS | 28034 | 7,186 | 21,278 |

Example 6

Generation of Clones of USP Promoters from *Vicia Faba*

Extended sequence USP promoters are obtained from *Vicia faba* genomic DNA via PCR amplification (Expand High Fidelity PCR System, Catalog number 1 732 641, Roche Molecular Biochemicals, Indianapolis, Ind.) and the Universal Genome Walker® kit (catalog number K1807-1 BD Biosciences, Palo Alto, Calif.) using a 3' primer designed according to the published sequence (GenBank Accession X56240). 5' primers are designed according to the Genome Walker protocol. Primers used for the first amplification of the USP promoters are: GATAAAACAGT-GAGATGTGCAAACTCC (uspGW-P-down) (SEQ ID NO: 12) and GTAATACGACTCACTATAGGGC (AP1, Adaptor Primer 1, supplied with kit) (SEQ ID NO: 13).

From these primary PCR products the promoters are amplified using nested primers CCATGGAGATCT-GACTGGCTATGAAGAAATTATAATCG (uspGW-N-down Bgl2Nco1) (SEQ ID NO: 14) and ACTAT-AGGGCACGCGTGGT (AP2, Nested Adaptor Primer 2) (SEQ ID NO: 15).

Figure 18:
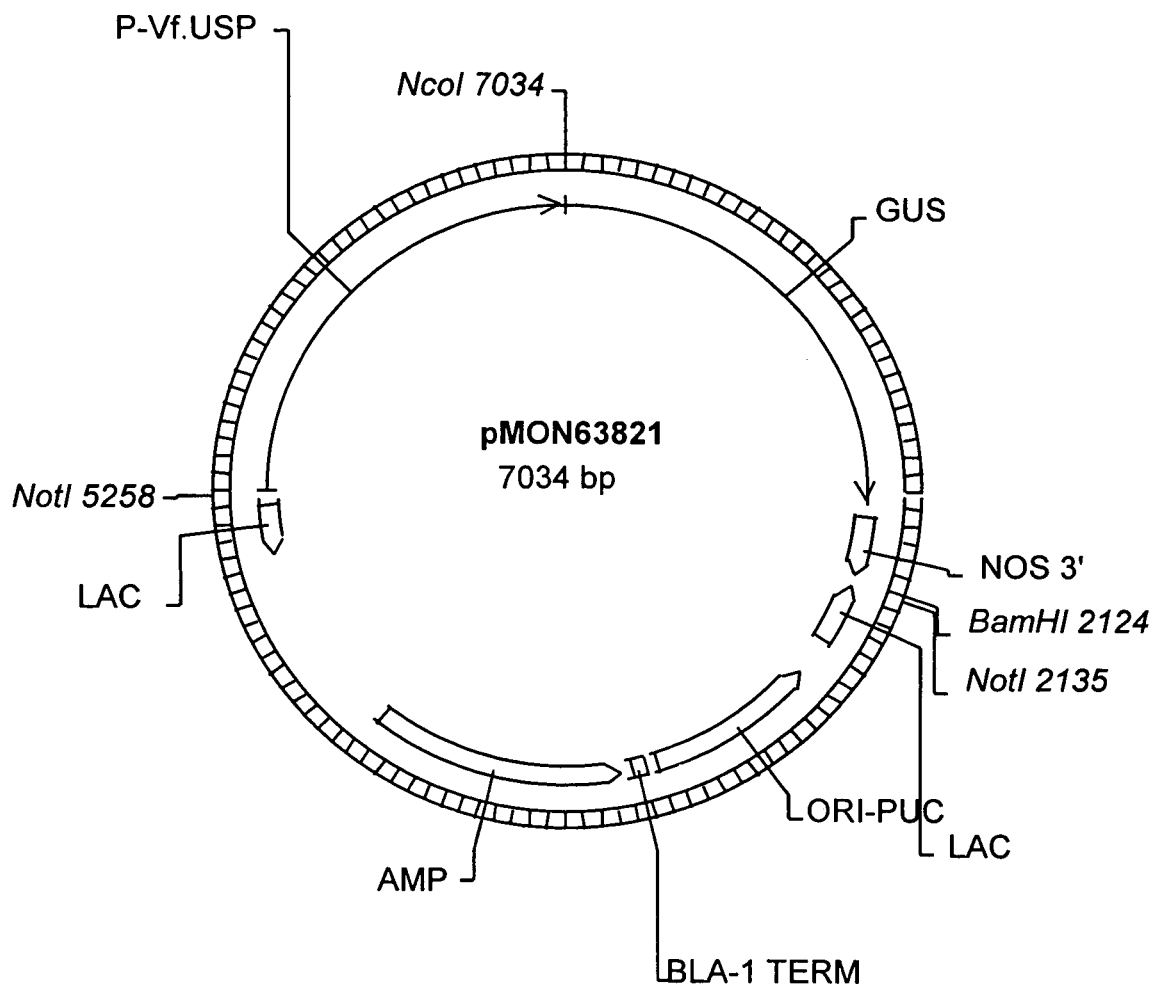
FIG. 18 is a schematic of vector pMON63821.
Figure 19:
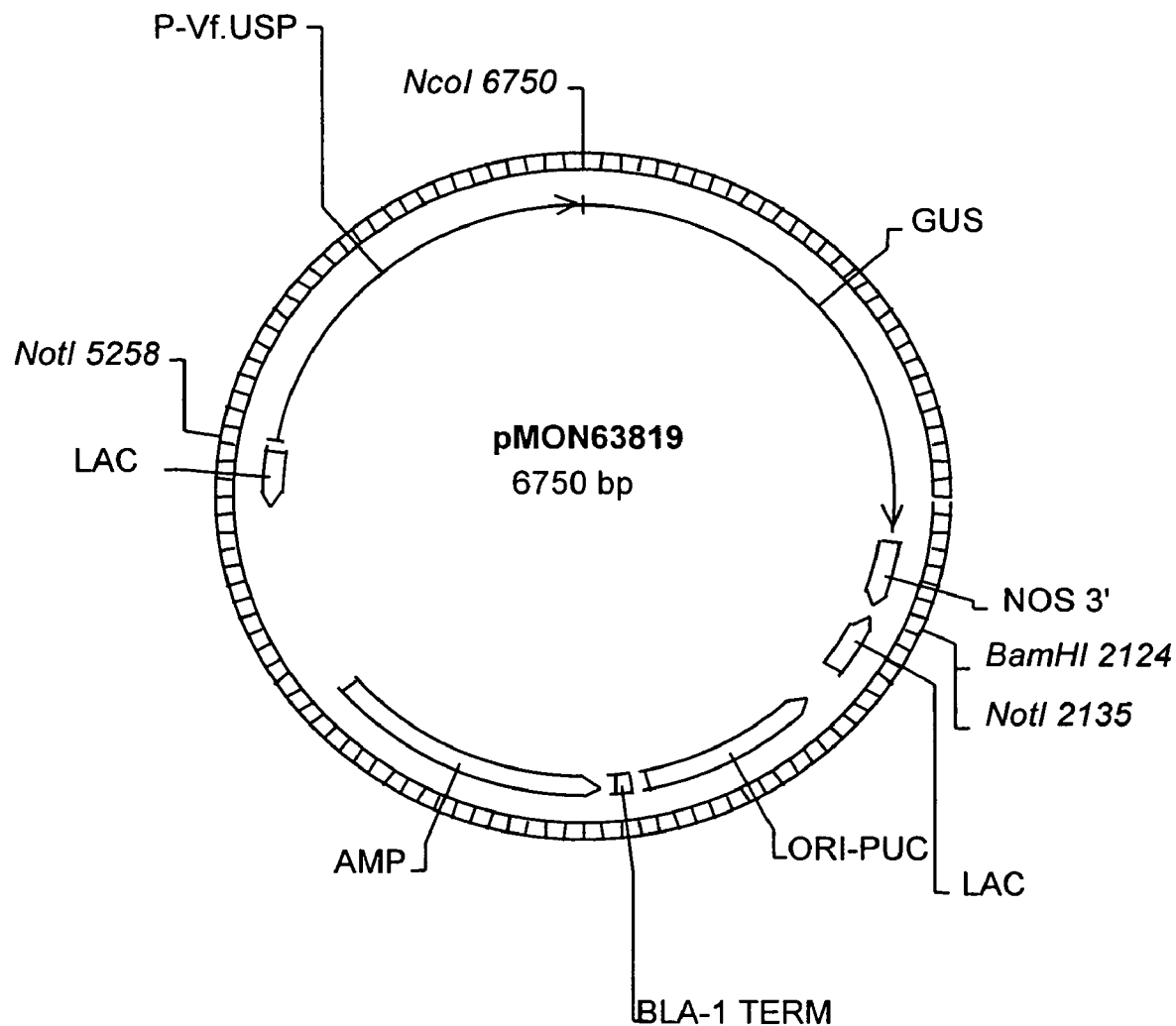
FIG. 19 is a schematic of vector pMON63819.
Figure 20:
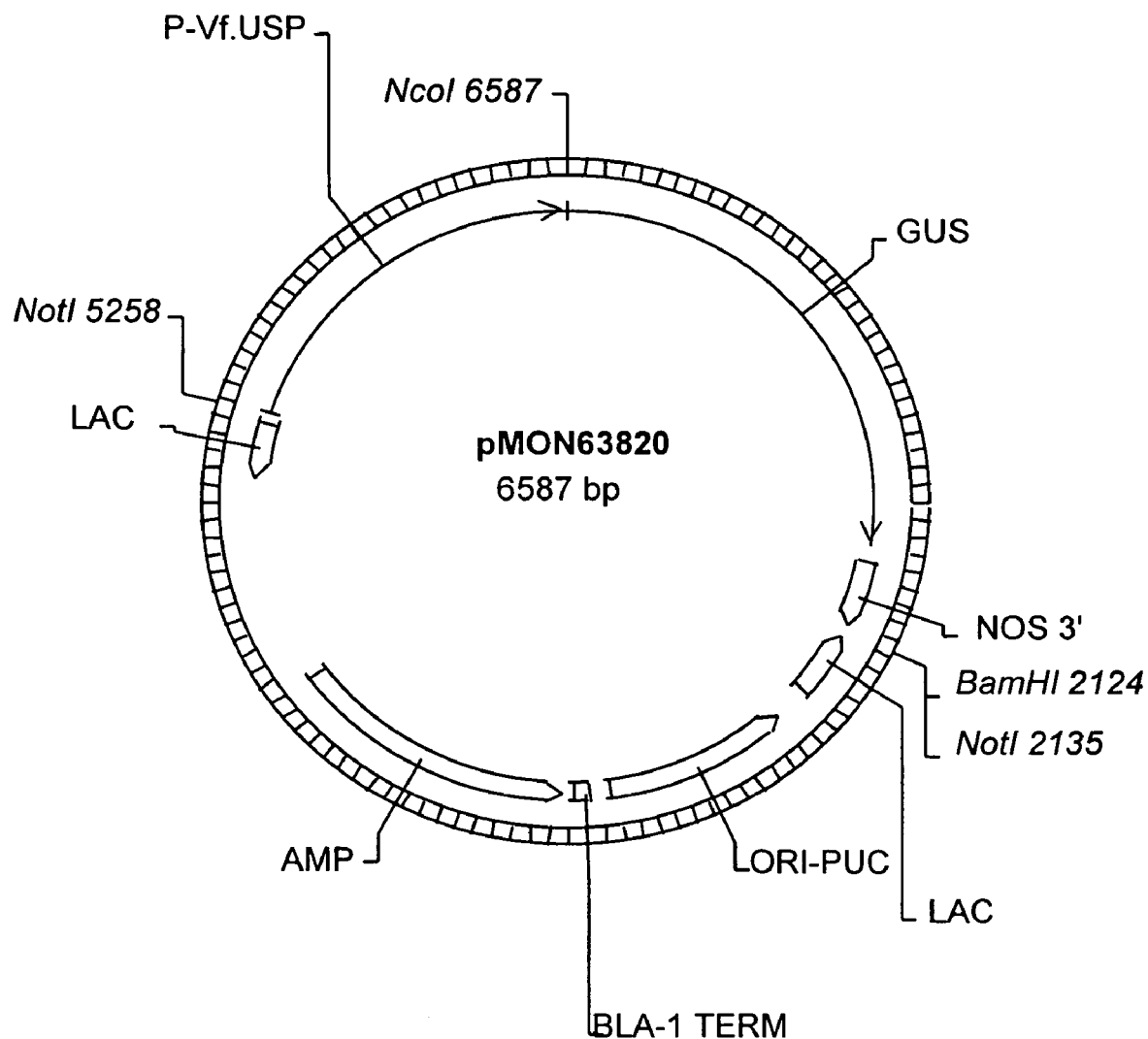
FIG. 20 is a schematic of vector pMON63820.

One microliter of the PCR fragment elution is used as template for a third round of PCR using uspGW-N-down Bgl2Nco1 and CTGCAGGTCGACGGCCCGGGCTGGT (AP6-Pst1/Srf1) (SEQ ID. NO: 16) in order to add convenient 5' restriction sites to the putative promoter fragments. The isolated amplification products are then subcloned into the vector pMON8677 producing clones pMON63821. (USP99.5) (FIG. 18), pMON63819 (USP95) (FIG. 19), and pMON63820 (USP68) (FIG. 20).

Example 7

Evaluation of USP Promoters Using Soybean Cotyledon Transient Transformation Seeds from soybean plants (Asgrow A3244) are harvested 25-28 days after flowering and osmotically treated overnight at 25° C. in dark on GAMBORG's medium (G5893, Sigma Company, St. Louis, Mo.) supplemented with of 50 mM glutamine, 111 mM maltose, 125 mM raffinose, 125 mM mannitol and 3 g/l purified agar, pH 5.6. The resulting 125 cotyledons are cut in half and bombarded with purified supercoiled DNA of pMON63819 (USP95), pMON63820 (USP68), pMON63621 (USP99.5), and pMON58101 (USP99) using particle gun technology (Maliga et al., 1995, "Methods in Plant Molecular Biology, A Laboratory Course Manual," Cold Spring Harbor Laboratory Press, p. 47). A separate e35S driven luciferase construct is included in a 1:1 molar ratio with each of the promoter constructs as an internal standard for expression. Bombarded tissues are incubated for 48 hours at 25° C.

Proteins are extracted from 6 bombarded soybean cotyledons using 1 ml extraction buffer containing 0.1 M potassium phosphate (pH 7.8), 10 mM DTT, 1 mM EDTA, 5% glycerol, and proteinase inhibitor (1 tablet/50 ml, Roche Molecular Biochemicals, Catalog number 1 697 498, Indianapolis, Ind.). A 100 µl aliquot of the protein extract is used for luciferase assay following a "Steady-Glo" procedure by Promega (Catalog number E2510, Promega Corporation Madison, Wis.). A 50 µl aliquot of the protein extract is used for a standard GUS assay protocol with minor modifications (Maliga et al., 1995, "Methods in Plant Molecular Biology, A Laboratory Course Manual", Cold Spring Harbor Laboratory Press, p. 29). Each sample is assayed twice and the average value is used for data analysis. GUS activity is normalized using luciferase activity and the relative promoter strength is expressed by comparing the expression of pMON58101 (USP99) with that of pMON63819 (USP95), pMON63820 (USP68), pMON63621 (USP99.5) (Table 5). pMON63621 (USP99.5) shows significantly higher expression than USP99, pMON63820 (USP68) shows significantly lower expression than USP99, and pMON63819 (USP95) shows similar expression to that of USP99. All three constructs were confirmed to contain active promoters in this transient expression system.

TABLE 5

Promoter Activity in a Transient Expression System

| Construct | Promoter | Relative GUS activity | Standard Error | Promoter Size (bp) |
|---|---|---|---|---|
| pMON58101 | USP99 | 1.59 | 0.10 | 682 |
| pMON63819 | USP95 | 1.47 | 0.21 | 1464 |
| pMON63820 | USP68 | 0.52 | 0.17 | 1301 |
| pMON63821 | USP99.5 | 2.81 | 0.82 | 1748 |

REFERENCES

Ainley et al., *Plant Mol. Biol.*, 14:949, 1990.
Ausubel et al., *Current Protocols in Molecular Biology*, John Wiley and Sons, Inc., 1995.
Bartley and Scolnik, *Plant Physiol.*, 104:1469-1470, 1994.
Back et al., *Plant Mol. Biol.*, 17:9, 1991.
Bauer et al., *Gene*, 37:73, 1985.
Becker and Guarente, In: Abelson and Simon (eds.), *Guide to Yeast Genetics and Molecular Biology, Methods Enzymol.*, 194:182-187, Academic Press, Inc., New York.
Bennett and LaSure (eds.), *More Gene Manipulations in Fungi*, Academic Press, California, 1991.
Bergeron et al., *TIBS*, 19:124-128, 1994.
Bustos et al., *EMBO J.*, 10:1469-1479, 1991.
Castresana et al., *EMBO J.*, 7:1929-1936, 1988.
Capecchi, *Cell*, 22(2):479-488, 1980.
Cerda-Olmedo et al., *J. Mol. Biol.*, 33:705-719, 1968.
Chau et al., *Science*, 244:174-181. 1989.
Christensen et al., *Plant Mol. Biol.*, 18:675-689, 1992.
Clapp, *Clin. Perinatol.*, 20(1):155-168, 1993.
Costa et al., *Methods Mol. Biol.*, 57:31-44, 1996.
Craik, *BioTechniques*, 3:12-19, 1985.
Craig, *Science*, 260:1902-1903, 1993.
Curiel et al., *Hum. Gen. Ther.*, 3(2):147-154, 1992.
Cyanobase, www.kazusa.orjp/cyanobase.
Dellaporta et al., *Stadler Symposium*, 11:263-282, 1988.
Demolder et al., *J. Biotechnology*, 32:179-189, 1994.
Deng and Nickloff, *Anal. Biochem.*, 200:81, 1992.
D'Halluin et al., *Bio/Technology*, 10:309-314, 1992.
Doyle et al., *J. Biol. Chem.*, 261:9228-9238, 1986.
Eglitis and Anderson, *Biotechniques*, 6(7):608-614, 1988.
Enderlin and Ogrydziak, *Yeast*, 10:67-79, 1994.
Feinbaum et al., *Mol. Gen. Genet.*, 226:449-456, 1991.
Fraley et al., *Proc. Natl. Acad. Sci. (U.S.A.)*, 80:4803, 1983.
Frits Eckstein et al., *Nucleic Acids Research*, 10:6487-6497, 1982.
Fromm et al., *Proc. Natl. Acad. Sci. (U.S.A.)*, 82(17):5824-5828, 1985.
Fromm et al., *Bio/Technology*, 8:833, 1990.
Fuller et al., *Proc. Natl. Acad. Sci. (U.S.A.)*, 86:1434-1438, 1989.

Fynan et al., *Proc. Natl. Acad. Sci. (U.S.A.)*, 90(24): 11478-11482, 1993.
Gething and Sambrook, *Nature*, 355:33-45, 1992.
Glick et al., Methods in Plant Molecular Biology and Biotechnology, CRC Press, Boca Raton, Fla., 1993.
Graham and Van der Eb, *Virology*, 54(2):536-539, 1973.
Greener et al., *Mol. Biotechnol.*, 7:189-195, 1997.
Hartl et al., *TIBS*, 19:20-25, 1994.
Hershey and Stoner, *Plant Mol. Biol.*, 17:679-690, 1991.
Hess, *Intern Rev. Cytol.*, 107:367, 1987.
Hinchee et al., *Bio/Technology*, 6:915-922, 1988.
Hinnen et al., *Proc. Natl. Acad Sci. (U.S.A.)*, 75:1920, 1978.
Horsch et al., *Science*, 227:1229-1231, 1985.
Ikatu et al., *Bio/Technol.*, 8:241-242, 1990.
Jarai and Buxton, *Current Genetics*, 26:2238-2244, 1994.
Jefferson (I), *Plant Mol. Biol, Rep.*, 5:387-405, 1987.
Jefferson (II) et al., *EMBO J*, 6:3901-3907, 1987.
Johnston and Tang, *Methods Cell Biol.*, 43(A):353-365, 1994.
Jones et al., *Science*, 266:789-793, 1994.
Jones et al., *Mol. Gen. Genet.*, 1987.
Julius et al., *Cell*, 32:839-852, 1983.
Julius et al., *Cell*, 37:1075-1089, 1984.
Kares et al., *Plant Mol. Biol.*, 15:905, 1990.
Katz et al., *J. Gen. Microbiol.*, 129:2703-2714, 1983.
Keegstra, *Cell*, 56(2):247-253, 1989.
Keller et al., *EMBO L.*, 8:1309-1314, 1989.
Knutzon et al., *Proc. Natl. Acad. Sci (U.S.A.)*, 89:2624-2628, 1992.
Kridl et al., *Seed Sci. Res.*, 1:209, 1991.
Kudla et al., *EMBO*, 9:1355-1364, 1990.
Kuhlemeier et al., *Seeds*, 1:471, 1989.
Kunkel, *Proc. Natl. Acad. Sci. (U.S.A.)*, 82:488-492, 1985.
Kyte and Doolittle, *J. Mol. Biol.*, 157:105-132, 1982.
Larn and Chua, *J. Biol. Chem.*, 266:17131-17135, 1990.
Lam and Chua, *Science*, 248:471, 1991.
Lipman and Pearson, *Science*, 227:1435-1441, 1985.
Lindstrom et al., *Developmental Genetics*, 11:160, 1990.
Lois et al., *Proc. Natl. Acad. Sci. (U.S.A.)*, 95(5):2105-2110, 1998.
Lu et al., *J. Exp. Med.*, 178(6):2089-2096, 1993.
Luo et al., *Plant Mol Biol. Reporter*, 6:165, 1988.
MacKenzie et al., *Journal of Gen. Microbiol.*, 139:2295-2307, 1993.
Malardier et al., *Gene*, 78:147-156, 1989.
Mandel et al., *Plant Mol. Biol.*, 29:995-1004, 1995.
McElroy et al., *Seeds*, 2:163-171, 1990.
Nawrath et al., *Proc. Natl. Acad. Sci. (U.S.A.)*, 91:12760-12764, 1994.
Needleman and Wunsch, *Journal of Molecular Biology*, 48:443-453, 1970.
Neuhaus et al., *Theor. Appl. Genet.*, 75:30, 1987.
Odell et al., *Nature*, 313:810, 1985.
Osuna et al., *Critical Reviews In Microbiology*, 20:107-116, 1994.
Ou-Lee et al., *Proc. Natl. Acad. Sci (U.S.A.)*, 83:6815, 1986.
Ow et al., *Science*, 234:856-859, 1986.
Pearson and Lipman, *Proc. Natl. Acad. Sci. (U.S.A.)*, 85:2444-2448, 1988.
Pearson, "Rapid and Sensitive Sequence Comparison with FAST? and FASTA." In *Methods in Enzymology*, (R. Doolittle, ed.), 183:63-98, Academic Press, San Diego, Calif., 1990.
Pearson, *Protein Science*, 4:1145-1160, 1995.
Pena et al., *Nature*, 325:274, 1987.
Poszkowski et al., *EMBO J.*, 3:2719, 1989.
Potrykus et al., *Ann. Rev. Plant Physiol. Plant Mol. Biol.*, 42:205, 1991.
Potrykus et al., *Mol. Gen. Genet.*, 199:183-188, 1985.
Puig and Gilbert, *J. Biol. Chem.*, 269:7764-7771, 1994.
Pyee et al., *Plant J.*, 7:49-59, 1995.
Reynaerts et al., Selectable and Screenable Markers. In Gelvin and Schilperoort. Plant Molecular Biology Manual, Kluwer, Dordrecht, 1988.
Richins et al., *Nucleic Acids Res.*, 20:8451, 1987.
Robinson et al., *Bio/Technology*, 1:381-384, 1994.
Rodriguez et al. Vectors: A Survey of Molecular Cloning Vectors and Their Uses, Butterworths, Boston, 1988.
Rogan and Bessman, *J. Bacteriol.*, 103:622-633, 1970.
Rogers et al., *Meth. In Enzymol.*, 153:253-277, 1987.
Saint Guily et al., *Plant Physiol.*, 100(2):1069-1071, 1992.
Samac et al., *Seeds*, 3:1063-1072, 1991.
Sambrook et al., *Molecular Cloning: A Laboratory Manual*, Second Edition, Cold Spring Harbor Laboratory Press, Cold Spring Harbor, N.Y., 1989.
Sato et al., *J. DNA Res.*, 7(1):31-63, 2000.
Schulze-Lefert et al., *EMBO J.*, 8:651, 1989.
Simpson, *Science*, 233:34, 1986.
Singer and Kusmierek, *Ann. Rev. Biochem.*, 52:655-693, 1982.
Slighton and Beachy, *Planta*, 172:356, 1987.
Smith et al., In: *Genetic Engineering: Principles and Methods*, Setlow et al., Eds., Plenum Press, NY, 1-32, 1981.
Smith and Waterman, *Advances in Applied Mathematics*, 2:482-489, 1981.
Smith et al., *Nucleic Acids Research*, 11:2205-2220, 1983.
Smith et al., *Plant J.*, 11:83-92, 1997.
Stalker et al., *J. Biol. Chem.*, 263:6310-6314, 1988.
Sutcliffe et al., *Proc. Natl. Acad. Sci. (U.S.A.)*, 75:3737-3741, 1978.
Takahashi et al., *Proc. Natl. Acad. Sci. (U.S.A.)*, 951(17):9879-9884, 1998.
Thillet et al., *J. Biol. Chem.*, 263:12500-12508, 1988.
Vandeyar et al. *Gene*, 65:129-133, 1988
Van Tunen et al., *EMBO J.*, 7:1257, 1988.
Verdier, *Yeast*, 6:271-297, 1990.
Vodkin et al., *Cell*, 34:1023, 1983.
Vogel et al., *J. Cell Biochem.*, (Suppl) 13D:312, 1989.
Wagner et al., *Proc. Natl. Acad. Sci. (U.S.A.)*, 89(13):6099-6103, 1992.
Wang and Tsou, *FASEB Journal*, 7:1515-1517, 1993.
Weissbach and Weissbach, *Methods for Plant Molecular Biology*, (Eds.), Academic Press, Inc., San Diego, Calif., 1988.
Weisshaar et al., *EMBO J.*, 10:1777-1786, 1991.
Wenzler et al., *Plant Mol. Biol.*, 12:41-50, 1989.
Williams, et al., *Biotechnology*, 10:540-543, 1992.
Wong and Neumann, *Biochim. Biophys. Res. Commun.*, 107(2):584-587, 1982.
Xia et al., *J. Gen. Microbiol.*, 138:1309-1316, 1992.
Yang et al., *Proc. Natl. Acad. Sci. (U.S.A.)*, 87:4144-48, 1990.
Yamaguchi-Shinozaki et al., *Plant Mol. Biol.*, 15:905, 1990.
Yelton et al., *Proc. Natl. Acad. Sci. (U.S.A.)*, 81:1470-1474, 1984.
Zhou et al., *Methods in Enzymology*, 101:433, 1983.
Zukowsky et al., *Proc. Natl. Acad. Sci. (U.S.A.)*, 80:1101-1105, 1983.
U.S. Pat. Nos. 4,683,195; 4,683,202; 4,757,011; 4,769,061; 4,885,357, 4,886,878, 4,940,835; 4,957,748; 4,971,908; 5,057,419; 5,093,249; 5,100,679; 5,147,792; 5,215,912; 5,219,596; 5,270,200; 5,298,421; 5,304,481; 5,344,771; 5,362,865; 5,576,203; 5,508,468; 5,003,045; 5,955,329;

5,367,110; 5,858,749; 6,040,160; 5,610,041; 5,618,988; 6,107,060; 5,811,636; 4,766,072; 5,003,045; 5,576,203; 5,384,253; 5,443,974; 5,512,482; 5,530,186; 5,534,421; 5,552,306; 5,589,616; 5,508,468; 5,614,393; 5,663,068; 5,663,068; 5,633,436; 5,639,790; 5,654,402; 5,659,645; 5,689,050; 5,689,050; 5,689,052; 5,705,391; 5,760,206; 5,759,829; 5,789,220; 5,807,893; 5,850,024; 5,856,157; 5,866,789; 5,885,802; 5,885,801; 5,914,450; 5,942,660; 5,945,585; 5,952,544; 5,955,650; 5,965,727; 5,995,329; 5,990,384; 5,990,389; 5,936,069; 5,939,599; 6,005,076; 6,051,754; 6,075,183; 6,043,411; 6,100,091; 6,107,051; 6,110,891; 6,117,677; 6,194,167; 6,146,669; 6,147,279; 6,156,227; 6,172,106; and 6,232,122.

European Patent: 0 154 204; 0 238 023; and 0 255 378.

Patent Applications: WO 90/01869, WO 91/13993, WO 92/14822, WO 93/08682, WO 94/20628, WO 95/19442, WO 97/26366, WO 97/28247, WO 97/22703, WO 98/55601, WO 98/26064, WO 96/17064, WO 97/35023, WO 00/19839, WO 99/06581, WO 99/02656, WO 99/40209, WO 99/11800, WO 99/49058, WO 00/32757, WO 00/10380.

What is claimed is:

1. An isolated nucleic acid molecule comprising a promoter operably linked to a second nucleic acid, wherein the promoter is selected from the group consisting of
   (a) SEQ ID NO:9 or the complement thereof; and
   (b) a fragment of SEQ ID NO:9 having promoter activity.

2. A transformed plant containing the nucleic acid molecule of claim 1.

3. The transformed plant of claim 2, wherein said second nucleic acid is a structural nucleic acid.

4. The transformed plant of claim 3, wherein said structural nucleic acid encodes a protein selected from the group consisting of a seed storage protein, a fatty acid pathway enzyme, a tocopherol biosynthetic enzyme, an amino acid biosynthetic enzyme, a steroid pathway enzyme, and a starch branching enzyme.

5. The transformed plant of claim 3, wherein said structural nucleic acid encodes a protein selected from the group consisting of anthranilate synthase, tryptophan decarboxylase, threonine deaminase and aspartate kinase.

6. The transformed plant of claim 4, wherein said structural nucleic acid encodes a starch branching enzyme.

7. The transformed plant of claim 3, wherein said structural nucleic acid is oriented to express an antisense RNA molecule.

8. The transformed plant of claim 3, wherein said transformed plant is selected from the group consisting of canola, crambe, mustard, castor bean, sesame, cottonseed, linseed, maize, soybean, *Arabidopsis* phaseolus, peanut, alfalfa, wheat, rice, oat, sorghum, rapeseed, rye, tritordeum, millet, fescue, perennial ryegrass, sugarcane, cranberry, papaya, banana, safflower, oil palms, flax, muskmelon, apple, cucumber, dendrobium, gladiolus, chrysanthemum, liliacea, cotton, eucalyptus, sunflower, *Brassica campestris, Brassica napus*, turfgrass, sugarbeet, coffee, and dioscorea.

9. The transformed plant of claim 3, wherein said transformed plant is soybean.

10. The transformed plant of claim 3, wherein said structural nucleic acid is expressed in an organ specific manner.

11. The transformed plant of claim 10, wherein said structural nucleic acid is expressed in a seed.

12. A method of producing a transformed plant comprising:
   (a) providing the nucleic acid molecule of claim 1; and,
   (b) transforming a plant with said nucleic acid molecule.

13. A method of obtaining a seed enhanced in a product of a structural nucleic acid comprising:
   (a) growing a transformed plant containing the nucleic acid molecule of claim 1, wherein said transformed plant produces said seed and said second nucleic acid is transcribed in said seed; and,
   (b) isolating said seed from said transformed plant.

14. A cell containing the nucleic acid molecule of claim 1.

15. The cell according to claim 14, wherein said cell is selected from the group consisting of a bacterial cell, a mammalian cell, an insect cell, a plant cell and a fungal cell.

16. The cell according to claim 15, wherein said cell is *Agrobacterium tumefaciens*.

17. A seed generated by a transformed plant containing the nucleic acid molecule of claim 1, wherein the seed comprises the nucleic acid molecule of claim 1.

18. A transformed soybean plant containing the nucleic acid molecule of claim 1.

19. The transformed plant of claim 18, wherein said second nucleic acid encodes a protein selected from the group consisting of a seed storage protein, a fatty acid pathway enzyme, a tocopherol biosynthetic enzyme, an amino acid biosynthetic enzyme, a steroid pathway enzyme, and a starch branching enzyme.

20. The transformed soybean plant of claim 18, wherein said second nucleic acid encodes a protein selected from the group consisting of anthranilate synthase, tryptophan decarboxylase, threonine deaminase and aspartate kinase.

21. The transformed soybean plant of claim 18, wherein said second nucleic acid encodes a starch branching enzyme.

22. The transformed soybean plant of claim 18, wherein said second nucleic acid is oriented to express an antisense RNA molecule.

23. The isolated nucleic acid molecule of claim 1, comprising SEQ ID NO:9.

24. The isolated nucleic acid molecule of claim 1, comprising a fragment of SEQ ID NO:9 having promoter activity.

* * * * *

SEQUENCE LISTING

```
<160> NUMBER OF SEQ ID NOS: 16

<210> SEQ ID NO 1
<211> LENGTH: 634
<212> TYPE: DNA
<213> ORGANISM: Vicia faba

<400> SEQUENCE: 1
ctgcagcaaa tttacacatt gtcactaaac gtctaaatca ttgtaatttg tttttgtttt      60
aatatgtgtg ttatgaactt gattttcaat aatttttaaa tttggtacca gtattataac     120
atcttttgtg ctaacggttg ccaacactta gcaatttgta agttgattaa ttgattctaa     180 actttattg tcttcttaat tcatgctgat aaatatatgc tgataaaaat taaagtgaat      240
atggtaccac aagttttttgg agactgttgc catatacacc aaacattcaa taattcttga    300
ggataataat ggtaccacac aagctttgag gtgcatgaac gtcacgtgga caaaaggttt     360
agtaattttt caagacaaca atgttaccac acacaagttt tgaggtgcat gcatggatgc     420
cctgtggaaa gtttaaaaat attttggaaa tgatttgcat ggaagccatg tgtaaaacca     480
tgacatccac ttggaggaag caataatgaa gaaaactaca aatttacatg caactagtta     540
tgcatgtagt ctatataatg aggattttgc aatactttca ttcataaaca ctcactaagt     600
tttacacgat tatcatttct tcatagccag tcaa                                 634

<210> SEQ ID NO 2
<211> LENGTH: 1185
<212> TYPE: DNA
<213> ORGANISM: Vicia faba

<400> SEQUENCE: 2
ctgcagcaaa tttacacatt gtcactaaac gtctaaatca ttgtaatttg tttttgtttt      60
aatatgtgtg ttatgaactt gattttcaat aatttttaaa tttggtacca gtattataac     120
atcttttgtg ctaacggttg ccaacactta gcaatttgta agttgattaa ttgattctaa     180 actttattg tcttcttaat tcatgctgat aaatatatgc tgataaaaat taaagtgaat      240
atggtaccac aagttttttgg agactgttgc catatacacc aaacattcaa taattcttga    300
ggataataat ggtaccacac aagctttgag gtgcatgaac gtcacgtgga caaaaggttt     360
agtaattttt caagacaaca atgttaccac acacaagttt tgaggtgcat gcatggatgc     420
cctgtggaaa gtttaaaaat attttggaaa tgatttgcat ggaagccatg tgtaaaacca     480
tgacatccac ttggaggaag caataatgaa gaaaactaca aatttacatg caactagtta     540
tgcatgtagt cctgcagcaa atttacacat tgtcactaaa cgtctaaatc attgtaattt     600 gttttttgttt taatatgtgt gttatgaact tgattttcaa taatttttaa atttggtacc    660
```

```
agtattataa catctttgt gctaacggtt gccaacactt agcaatttgt aagttgatta         720
attgattcta aacttttatt gtcttcttaa ttcatgctga taaatatatg ctgataaaaa         780
ttaaagtgaa tatggtacca caagttttg gagactgttg ccatatacac caaacattca         840
ataattcttg aggataataa tggtaccaca caagctttga ggtgcatgaa cgtcacgtgg         900
acaaaaggtt tagtaatttt tcaagacaac aatgttacca cacacaagtt ttgaggtgca         960
tgcatggatg ccctgtggaa agtttaaaaa tattttggaa atgatttgca tggaagccat        1020
gtgtaaaacc atgacatcca cttggaggaa gcaataatga agaaaactac aaatttacat        1080
gcaactagtt atgcatgtag tctatataat gaggattttg caatactttc attcataaac        1140
actcactaag ttttacacga ttatcatttc ttcatagcca gtcaa                        1185

<210> SEQ ID NO 3
<211> LENGTH: 688
<212> TYPE: DNA
<213> ORGANISM: Vicia faba

<400> SEQUENCE: 3
ctgcagcaaa tttacacatt gccactaaac gtctaaaccc ttgtaatttg ttttatttc          60 gctatgtgtg ttatgtattt aatttgcgat aaattttat atttggtact aaatttataa         120
caccttttat gctaacgttt gccaacactt agcaatttgc aagttgatta atcgattcta        180
aattattttt gtcttctaaa tacatatact aatcaactgg aaatgtaaat atttgctaat        240
atttctacta taggagaatt aaagtgagtg aatatggtac cacaaggttt ggagatttaa        300
ttgttgcaat gcttgcatgg atggcatata caccaaacat tcaataattc ttgaggataa        360
taatggtacc acacaagctt tgaggtgcat gaacgtcacg tggacaaaag gtttagtaat        420
ttttcaagac aacaatgtta ccacacacaa gttttgaggt gcatgcatgg atgccctgtg        480
gaaagtttaa aaatatttg gaaatgatt gcatggaagc catgtgtaaa accatgacat         540
ccacttggag gaagcaataa tgaagaaaac tacaaattta catgcaacta gttatgcatg        600
tagtctatat aatgaggatt ttgcaatact ttcattcata aacactcact aagttttaca        660
cgattatcat ttcttcatag ccagtcaa                                          688

<210> SEQ ID NO 4
<211> LENGTH: 744
<212> TYPE: DNA
<213> ORGANISM: Vicia faba

<400> SEQUENCE: 4
ctgcagcaaa tttacacatt gccactaaac gtctaaaccc ttgtaatttg ttttatttc          60 actatgtgtg ttacgtattt aatttgcgat aaattttat atttggtact aaatttataa         120
caccttttat gctaacgttt gccaacactt agcaatttgc aagttgaaat ttataacacc        180
ttttatgcta acgtttgcca acacttagca atttgcaagt tgattaatcg attctaaatt        240 attttgtct ctaaataca tatactaatc aactggaaat gtaaatattt gctaatatt          300 ctactatagg agaattaaag tgagtgaata tggtaccaca aggtttggag atttaattgt        360
tgcaatgctt gcatggatgg catatacacc aaacattcaa taattcttga ggataataat        420
ggtaccacac aagctttgag gtgcatgaac gtcacgtgga caaaaggttt agtaattttt        480
caagacaaca atgttaccac acacaagttt gaggtgcat gcatggatgc cctgtggaaa        540
gtttaaaaat attttggaaa tgatttgcat ggaagccatg tgtaaaacca tgacatccac        600
```

-continued

```
ttggaggaag caataatgaa gaaaactaca aatttacatg caactagtta tgcatgtagt         660
ctatataatg aggattttgc aatactttca ttcataaaca ctcactaagt tttacacgat         720
tatcatttct tcatagccag tcaa                                                744

<210> SEQ ID NO 5
<211> LENGTH: 688
<212> TYPE: DNA
<213> ORGANISM: Vicia faba

<400> SEQUENCE: 5
ctgcagcaaa tttacacatt gccactaaac gtctaaaccc ttgtaatttg ttttttgtttt         60 actatgtgtg ttatgtattt gatttgcgat aaattttttat atttggtact aaatttataa        120 cacctttat gctaacgttt gccaacactt agcaatttgc aagttgatta attgattcta         180
aattattttt gtcttctaaa tacatatact aatcaactgg aaatgtaaat atttgctaat         240
atttctacta taggagaatt aaagtgagtg aatatggtac cacaaggttt ggagatttaa         300
ttgttgcaat gctgcatgga tggcatatac accaaacatt caataattct tgaggataat         360
aatggtacca cacaagattt gaggtgcatg aacgtcacgt ggacaaaagg tttagtaatt         420
tttcaagaca acaatgttac cacacacaag ttttgaggtg catgcatgga tgcccctgtg         480
gaaagtttaa aaatattttg gaatgatttt gcatggaagc catgtgtaaa accatgacat         540
ccacttggag gatgcaataa tgaagaaaac tacaaattta catgcaacta gttatgcatg         600
tagtctatat aatgaggatt ttgcaatact tcattcata cacactcact aagttttaca         660
cgattataat ttcttcatag ccagtcaa                                             688

<210> SEQ ID NO 6
<211> LENGTH: 24
<212> TYPE: DNA
<213> ORGANISM: Vicia faba

<400> SEQUENCE: 6
aaactgcagc aaatttacac attg                                                 24

<210> SEQ ID NO 7
<211> LENGTH: 22
<212> TYPE: DNA
<213> ORGANISM: Vicia faba

<400> SEQUENCE: 7
aaaccatggt tgactggcta tg                                                   22

<210> SEQ ID NO 8
<211> LENGTH: 24
<212> TYPE: DNA
<213> ORGANISM: Vicia faba

<400> SEQUENCE: 8
aaactgcagg actacatgca taac                                                 24

<210> SEQ ID NO 9
<211> LENGTH: 1749
<212> TYPE: DNA
<213> ORGANISM: Vicia faba

<400> SEQUENCE: 9
acttcgacca actagagttc gatccaaaat cccacatacg caataccaaa cattaactga         60
agtttttcaa ggaggctcaa aactatcgag aatgtctcat catcattgac atcatcgtct        120
```

-continued

```
cgaagctccg tgaaagaaca aacacattat gccaaacatt atctttatga atatattacc      180
acagaccatc actccgacct tgcaatcaag aatggtgtca ttgtcgttac cctaatggta      240
gggtggatca aacaagaggt ctatgttagt tttatcggac ccctaaaaag tacaatgaga      300
taaccctatg tttttagtgt tgttttatgt atttagaggg tttgctcatg catgcgtagt      360
ggttagaagt aaggttgtct agatcaaaat tttacataag atccggagag aataacaaga      420
ttgtaaaata taaaatcgta gttaagatta aagattttta ctcaattatt tttgtaagat      480
tgacagcgaa taacatcgta aaacataaga taataaaaaa aaagtaagat cctactaaaa      540
tgaaaaaaaa atagtatata tttaaagtat ttttacatga tataatgatg tatgtaagta      600
ggcaagtgta tttgtgagaa aaaaatattc tttttcatat tctttaaaca tttacgattg      660
aggttttatt aaatatttgt taatgtttag acattagaga catatatagt caattactaa      720
gattatcata agtctactta aaacaaatct tatatgttaa agtttattc tctaaatcct       780 aaatctaaaa tttcatttca aaaggtgaaa attcatctcc gctgaaccat attgtgcttc      840
cacatcttgt catcattctc acattttaat ggtggtggtc gtaaaacggt gaatcatagt      900
caaagctggc aaagatcgca caaatcaat aattttaaaa gaattttat tcaatttagc       960 tacaattcgc gattctactt gaaatctgac aaccatacat atttatatac cgataaaata     1020
taggctatat tatacatttg cctttaaaaa aaactgaaaa actcctgcag caaatttaca     1080
cattgccact aaacgtctaa acccttgtaa tttgtttttg ttttactatg tgtgttatgt     1140
atttgatttg cgataaattt ttatatttgg tactaaattt ataacaccttt ttatgctaac    1200 gtttgccaac acttagcaat ttgcaagttg attaattgat tctaaattat ttttgtcttc    1260
taaatacata tactaatcaa ctggaaatgt aaatatttgc taatatttct actataggag    1320
aattaaagtg agtgaatatg gtaccacaag gtttggagat ttaattgttg caatgctgca    1380
tggatggcat atacaccaaa cattcaataa ttccttgagga aataatggt accacacaag    1440 atttgaggtg catgaacgtc acgtggacaa aaggtttagt aatttttcaa gacagcaatg    1500
ttaccacaca caagttttga ggtgcatgca tggatgccct gtggaaagtt taaaatatt     1560 ttggaaatga tttgcatgga agccatgtgt aaaaccatga catccacttg gaggatgcaa    1620
taatgaagaa aactcaaaat ttacatgcaa ctagttatgc atgtagtcta tataatgagg    1680
attttgcaat actttcattc atacacactc actaagtttt acacgattat aatttcttca    1740
tagccagtc                                                            1749
```

<210> SEQ ID NO 10
<211> LENGTH: 1465
<212> TYPE: DNA
<213> ORGANISM: Vicia faba

<400> SEQUENCE: 10

```
cctatgttag ttttatcgga cacctaaaaa gtacaatgag ataaccttat gttttagtg       60 ttgttttatg tgtttagagt gtttgctcat gcatagtggt tagaagtaag gttgtcaaga     120
tcgaaacttt acataagatc tggagagaat aataagattg taaatataa aattttagtt     180 aagataagaa gattactc aattatttt gtaagattga cagggaataa cataatcgta       240
aatcataaga tagtaacaaa aaaagtaaga tcctactaaa ataaaaaaat taatagtata    300
tatttaaagt attttacat gatataatga tgtatgtaag tatgcaagtg tatttgtgag     360
aaaaaaaata ctcttttttca tattctttaa acatttatga ttgagatttt attaaatatt    420
```

```
tgttaatgtt tagacattag agacatatat ggtcaattat taggattatc ataagtttag      480
ttaaaacaaa tcttatatgt taaaagttta ttctctaaac cttaaatcta aaactttatt      540
tcacaaagcg aaaattcatc cccgctgaat cgtaaatatt gtgcttccac atcttgtcat      600
cattctcaca ttttaatagt ggtggtcgta aaacggtgaa tcatggccaa agctgacaaa      660
gatcgcacaa atcaataat ttatagattt tttattcaat ttagctacaa tacacgagtc      720
tacttgaaat cgagattttg acaaccatat atattcatat acagataaaa tgtaggctat      780
gttatacatt tgcctttaaa aaactgaaa aactcctgca gcaaatttac acattgccac       840
taaacgtcta aacccttgta aattattttt gttttactat gtgtgttatg aacttgattt     900
tcaataattt ttaaatttgg taccagtatt ataacatctt tgtgctaac ggttgccaac      960 acagcaattt gtaagttgat taattgattc tatactttta ttgtctcctt aattcatgct    1020
gataaatata tgctgataaa aattaaagtg aatatggtac cacaaggttt ggagatttaa    1080
ttgttgcaat gctgcatgga tggcatatac accaaacatt caataattct tgaggataat    1140
aatggtacca cacaagcttt gaggtgcatg aacatcgcgt ggacaaaagg tttagtaatt    1200
tttcaagaca caatgttac cacacacaag ttttgaggtg catgcatgga tgccctgtgg     1260
aaagtttaaa aatattttgg aaatgatttg catggaagcc atgtgtaaaa ccatgacatc    1320
cacttggagg aagcaataat gaagaaaact acaaatttac atgcaactag ttatgcatgt    1380
agtctatata atgaggattt tgcaatactt tcattcataa acactcacta agttttacac    1440
gattataatt tcttcatagc cagtc                                          1465

<210> SEQ ID NO 11
<211> LENGTH: 1302
<212> TYPE: DNA
<213> ORGANISM: Vicia faba

<400> SEQUENCE: 11
cctatgttag ttttatcgga cccctaaaaa gtacaatgag ataaccttat gttttagtg       60 ttgttatatg tgtttagagg gtttgctcat gcatagtgga tagaagtaag gttgccaaga    120
tcaaaatttt acataagatc aggagagaat aacaagattg taaaatataa aattctagtt    180
aagataagaa gattttactc aattattttt gtaagattga cagggaataa cataatagta    240
aattataata tagtaacaaa aaaagtaaga tcctactaaa ataaaaaaa taatagtata    300 tatttaaagt attttaacat gatataatga tgtatgtaag tatgcaagtg tatttgtgag    360 aaaaaaaaa aactctttt catattcttt aaacatttat gattgaggtt ttattaaata    420
tttgttaatg tttagacatt agagacatat atggtcaatt attaggatta tcataagttt    480
agttaaaata atcttatat gttaaaagtt tattctctaa accttatatc taaaatttca    540
tttcaaaagg ccaaaattta tctccgctga accgtaatta ttgtgcttcc gcatcttgtc    600
atcattctca tattttaata gtggtggtcg taaaacggtg aatcatggtc aaagctgaca    660
aagatcgcac aaaatccata attttataga ttttttattc aatttagcta caatacgcga    720
ttctacttga aatcgagatt ttgacaacta tacatattca tatacagata aaatataggc    780
tatgttatac atttgccttt aaaaaaaaaa actgaaaaac tcctgcagca aatttacaca    840
ttgccactaa acgtctaaac ccttgtaatt tgttttttgtt ttaatatgtg tgttatgaac    900
ttgatttgca ataattttta aatttggtac tagtattata acaccttttg tgctaacggt    960
tgccaacact tagtaatttg taagttgatt aattgattct aaactattat tgtcttctta   1020
aatcatatcc taaataatcg aaaatgtaaa tatatgctga taaaaattaa agtgaatatg   1080
```

-continued

```
gtaccacaag tttttggaaa gtttaaaaat attttggaaa tgatttgcat ggaagccatg    1140
tgtaaaacca tgacatccac ttggaggaag caataatgaa gaaaactaca aatttacatg    1200
caactagtta tgcatgtagt ctatataatg aggattttgc aatactttca ttcatacaca    1260
ctcactaagt tttacacgat tataatttct tcatagccag tc                       1302
```

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Artificial
      polynucleotide

<400> SEQUENCE: 12

```
gataaaacag tgagatgtgc aaactcc                                          27
```

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Artificial
      polynucleotide

<400> SEQUENCE: 13

```
gtaatacgac tcactatagg gc                                               22
```

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: Artificial
      polynucleotide

<400> SEQUENCE: 14

```
ccatggagat ctgactggct atgaagaaat tataatcg                              38
```

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Artificial
      polynucleotide

<400> SEQUENCE: 15

```
actatagggc acgcgtggt                                                   19
```

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Artificial
      polynucleotide

<400> SEQUENCE: 16

```
ctgcaggtcg acggcccggg ctggt                                            25
```